(12) United States Patent
Labrie

(10) Patent No.: US 10,342,805 B2
(45) Date of Patent: Jul. 9, 2019

(54) TREATMENT OF ALZHEIMER'S DISEASE, LOSS OF COGNITION, MEMORY LOSS AND DEMENTIA WITH SEX STEROID PRECURSORS IN COMBINATION WITH SELECTIVE ESTROGEN RECEPTOR MODULATORS

(71) Applicant: Fernand Labrie, Québec (CA)

(72) Inventor: Fernand Labrie, Québec (CA)

(73) Assignee: ENDORECHERCHE, INC. (CA)

( * ) Notice: Subject to any disclaimer, the term of this patent is extended or adjusted under 35 U.S.C. 154(b) by 0 days.

(21) Appl. No.: 13/875,027

(22) Filed: May 1, 2013

(65) Prior Publication Data

US 2013/0244989 A1    Sep. 19, 2013

Related U.S. Application Data

(62) Division of application No. 12/791,174, filed on Jun. 1, 2010.

(Continued)

(51) Int. Cl.
  *A61K 31/453* (2006.01)
  *A61K 31/568* (2006.01)
  *A61K 31/5685* (2006.01)

(52) U.S. Cl.
  CPC ........ *A61K 31/5685* (2013.01); *A61K 31/453* (2013.01); *A61K 31/568* (2013.01)

(58) Field of Classification Search
  None
  See application file for complete search history.

(56) References Cited

U.S. PATENT DOCUMENTS 3,742,951 A  7/1973 Zaffaroni ............ 128/268
3,797,444 A  3/1974 Stubbs ............... 114/235
(Continued)

FOREIGN PATENT DOCUMENTS

AU    2012204083 C1   8/2012
CA    2 395 730 A1    8/2001
(Continued)

OTHER PUBLICATIONS

Gauthier et al. "Alzheimer's disease: Current knowledge, management and research." Can. Med. Assoc. J. 1997; 157(8): 1047-1052.*

(Continued)

*Primary Examiner* — Anna Pagonakis
(74) *Attorney, Agent, or Firm* — Ostrolenk Faber LLP

(57) ABSTRACT

Novel methods for reduction or elimination the incidence of hot flushes, vasomotor symptoms, and night sweats while decreasing the risk of acquiring breast, uterine or endometrial cancer and furthermore having beneficial effect by inhibiting the development of osteoporosis, hypercholesterolemia, hyperlipidemia, atherosclerosis, hypertension, insulin resistance, diabetes type 2, loss of muscle mass, adiposity, Alzheimer's disease, loss of cognition, loss of memory, or vaginal dryness in susceptible warm-blooded animals including humans involving administration of an amount of a sex steroid precursor, particularly dehydroepiandrosterone (DHEA) and an antiestrogen or a selective estrogen receptor modulator, particularly compounds having the general structure:

(Continued)

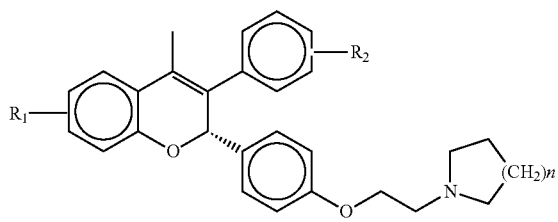

Pharmaceutical compositions for delivery of active ingredient(s) and kit(s) useful to the invention are also disclosed.

9 Claims, 28 Drawing Sheets

Related U.S. Application Data

(60) Provisional application No. 61/187,549, filed on Jun. 16, 2009.

(56) References Cited

U.S. PATENT DOCUMENTS

| | | | | |
|---|---|---|---|---|
| 4,568,343 | A | 2/1986 | Leeper et al. | 604/896 |
| 4,624,665 | A | 11/1986 | Nuwayser | 604/307 |
| 4,666,441 | A | 5/1987 | Andriola et al. | 604/897 |
| 5,064,654 | A | 11/1991 | Berner et al. | 424/448 |
| 5,071,644 | A | 12/1991 | Viegas et al. | 514/772 |
| 5,071,657 | A | 12/1991 | Oloff et al. | 424/486 |
| 5,135,480 | A | 8/1992 | Bannon et al. | 604/20 |
| 5,154,922 | A | 10/1992 | Govil et al. | 424/448 |
| 5,162,037 | A | 11/1992 | Whitson-Fischman | 60/12 |
| 5,292,730 | A * | 3/1994 | Lardy | A61K 31/565 514/169 |
| 5,707,983 | A | 1/1998 | Lardy | |
| 5,776,923 | A | 7/1998 | Labrie | 514/176 |
| 6,465,445 | B1 | 10/2002 | Labrie | 514/171 |
| 6,670,346 | B1 | 12/2003 | Labrie | 514/171 |
| 6,710,059 | B1 | 3/2004 | Labrie et al. | 514/320 |
| 8,268,806 | B2 | 9/2012 | Labrie | |
| 8,629,129 | B2 | 1/2014 | Labrie | |
| 8,957,054 | B2 | 2/2015 | Labrie et al. | |
| 9,744,177 | B2 | 8/2017 | Labrie et al. | |
| 2002/0198179 | A1 | 12/2002 | Labrie | 514/102 |
| 2003/0040510 | A1 | 2/2003 | Labrie | 514/177 |
| 2003/0065008 | A1 | 4/2003 | Labrie | 514/311 |
| 2004/0121991 | A1 | 6/2004 | Araneo et al. | |
| 2007/0270394 | A1 | 11/2007 | El-Alfy et al. | 514/178 |
| 2009/0054383 | A1 | 2/2009 | Labrie | |
| 2012/0322778 | A1 | 12/2012 | Labrie | |

FOREIGN PATENT DOCUMENTS

| | | |
|---|---|---|
| CA | 2 574 766 A1 | 1/2006 |
| CA | 2 696 127 | 2/2009 |
| EP | 0 167 057 A2 | 1/1986 |
| EP | 0 279 982 A1 | 11/1987 |
| EP | 0 746 322 B1 | 12/1996 |
| EP | 0 802 183 A1 | 10/1997 |
| EP | 1559707 A1 | 8/2005 |
| EP | 1 623 712 A2 | 2/2006 |
| EP | 1 196 163 B1 | 11/2009 |
| GB | 2 185 187 | 6/1986 |
| JP | S62-99328 A | 5/1987 |
| JP | 10-036347 | 2/1998 |
| JP | 2006-514694 A | 5/2006 |
| JP | 2007-191484 A | 8/2007 |
| KR | 10-2006-0098399 | 9/2006 |
| WO | WO 94/16709 | 8/1994 |
| WO | WO 97/32837 | 3/1996 |
| WO | WO 97/25034 | 1/1997 |
| WO | WO 97/25035 | 1/1997 |
| WO | WO 97/25036 | 1/1997 |
| WO | WO 97/25037 | 1/1997 |
| WO | WO 97/25038 | 1/1997 |
| WO | WO 99/63973 | 12/1999 |
| WO | WO 99/63974 | 12/1999 |
| WO | WO 99/63978 A2 | 12/1999 |
| WO | WO 01/01969 | 1/2001 |
| WO | WO 01/51056 | 7/2001 |
| WO | WO 01/54699 A1 | 8/2001 |
| WO | WO 03/092588 * | 11/2003 |
| WO | WO 2004/031125 A1 | 4/2004 |
| WO | WO 2004/058048 A2 | 7/2004 |
| WO | WO 2004/080413 A2 | 9/2004 |
| WO | WO 2005/052005 A1 | 6/2005 |
| WO | WO 2005/073204 A1 | 8/2005 |
| WO | WO 2006/042409 | 4/2006 |
| WO | WO 2007/102861 A2 | 9/2007 |
| WO | WO 2008/003432 A1 | 1/2008 |
| WO | WO 2009/021323 A1 | 2/2009 |

OTHER PUBLICATIONS

Greicius et al. Presenile dementia syndromes: an update on taxonomy and diagnosis. Journal of Neurol. Neurosurg. Psychiatry, 2002; 72: 691-700.*

Gasparini et al. Peripheral markers in treating pathophysiological hypotheses and diagnosing Alzheimer's disease. FASEB. J. 12, 1998: 17-34.*

Nakawatase et al. "Alzheimer's disease and related dementias." Cecil's Textbook of Medicine. Twenty-First Edition, vol. 1, W.B. Saunders Company, 2000, pp. 2042-2045.*

Berger et al. Effects of dehydroepiandrosterone, permarin and acolbifene on histomorphology and sex steroid receptors in the rat vagina. Jorunal of Steroid Biochemistry & Molecular Biology, 96, 2005, 201-215.*

Labrie et al. The combination of a novel selective estrogen receptor modulator with an estrogen protects the mammary gland and uterus in a rodent model: the future of postmenopausal women's health? Endocrinology, 144(11): 4700-4706.*

Cummings, S.R., Evaluating the benefits and risks of postmenopausal hormone therapy, The American Journal of Medicine, 1991, 91(5B), 14S-18S.

Judd, H.L. et al., Estrogen replacement therapy: indications and complications. Annals of Internal Medicine, 1983, 98, 195-205.

Bélanger, A. et al., Changes in serum concentrations of conjugated and unconjugated steroids in 40- to 80-year-old men, Journal of Clinical Endocrinology and Metabolism, 1994, 79(4), 1086-1090.

Hackbert and Heiman, Acute dehydroepiandrosterone (DHEA) effects on sexual arousal in postmenopausal women, Journal of Women's Health & Gender-Based Medicine, Mar. 2002; 11(2):155-62.

Huang et al., Estrogen regulates neprilysin activity in rat brain, Neuroscience Letter, 2004, 367, 85-87.

Villareal, D.T. et al., Effects of DHEA replacement on bone mineral density and body composition in elderly women and men, Clinical Endocrinology, 2000, 53, 561-568.

Stephanie R. Land, PhD, et al., "Patient-Reported Symptoms and Quality of Life During Treatment With Tamoxifen or Raloxifene for Breast Cancer Prevention—The NSABP Study of Tamoxifen and Raloxifene (STAR) P-2 Trial," JAMA, vol. 295, No. 23, pp. 2742-2751, Jun. 21, 2006.

Silvana Martino, et al., "Safety Assessment of Raloxifene Over Eight Years in a Clinical Trial Setting," Current Medical Research and Opinions, vol. 21, No. 9, pp. 1441-1452, 2005.

Stefano Lello, et al., "Bazedoxifene: Literature Data and Clinical Evidence," Clinical Cases in Mineral and Bone Metabolism, 8(3): pp. 29-32, 2011.

Charles L. Vogel, et al., "Multicenter Phase II Efficacy Trial of Toremifene in Tamoxifen-Refractory Patients With Advanced Breast Cancer," Journal of Clinical Oncology, vol. 11, No. 2, pp. 345-350, Feb. 1993.

E. Michael Lewiecki, "Lasofoxifene for the Prevention and Treatment of Postmenopausal Osteoporosis," Therapeutics and Clinical Risk Management, 5, pp. 817-827, 2009.

(56) References Cited

OTHER PUBLICATIONS

Céline Bouchard, MD, FRCSC, Editorial—"Selective Estrogen Receptor Modulators and Their Effects on Hot Flashes: A Dilemma," Menopause: The Journal of the North American Menopause Society, vol. 18, No. 5, pp. 477-479, 2011.
Jens Hoffmann, et al., "Characterization of New Estrogen Receptor Destabilizing Compounds: Effects on Estrogen-Sensitive and Tamoxifen-Resistant Breast Cancer," Journal of the National Cancer Institute, vol. 96, No. 3, pp. 210-218, Feb. 4, 2004.
Nareshkumar Jain, et al., "Novel Chrome-Derived Selective Estrogen Receptor Modulators Useful for Alleviating Hot Flushes and Vaginal Dryness," J. Med. Chem., 2006, 49, pp. 3056-3059.
O.E. Young et al, "Effects of Fulvestrant 750 mg in Premenopausal Women With Oestrogen-Receptor-Positive Primary Breast Cancer," European Journal of Cancer 44, pp. 391-399, 2008.
Monique Curran, "Fulvestrant," ADIS New Drug Profile, Drugs 2001: 61(6), pp. 807-813.
Richard B. Silverman, "The Organic Chemistry of Drug Design and Drug Action," Academic Press, Inc., Harcourt Brace Jovanovich, Publishers, Chapter 8, Prodrugs and Drug Delivery Systems, pp. 352-357 (1992).
Nareshkumar Jain, et al., "Novel Chromene-Derived Selective Estrogen Receptor Modulators Useful for Alleviating Hot Flushes and Vaginal Dryness," Journal of the Medicinal Chemistry, Jun. 1, 2006, 49 (11), pp. 3056-3059.
Nareshkumar Jain, et al., Supporting Information—"Novel Chromene-Derived Selective Estrogen Receptor Modulators Useful for Alleviating Hot Flush and Vaginal Dryness," Johnson & Johnson Pharmaceutical Research & Development LLC, Raritan, New Jersey, pp. S1-S38 for Nareshkumar Jain, et al., "Novel Chromene-Derived Selective Estrogen Receptor Modulators Useful for Alleviating Hot Flushes and Vaginal Dryness," Journal of the Medicinal Chemistry, Jun. 1, 2006, 49 (11), pp. 3056-3059.
Nareshkumar Jain, et al., "Identification and Structure—Activity Relationships of Chromene-Derived Selective Estrogen Receptor Modulators for Treatment of Postmenopausal Symptoms," Journal of the Medicinal Chemistry, 2009, 52(23), pp. 7544-7569.
Wuhong Chen, et al., "Aza Analogues of Equol: Novel Ligands for Estrogen Receptor β," Bioorganic & Medicinal Chemistry, 2007, 15, pp. 5828-5836.
Sonsoles Martín-Santamaría, et al., "New Scaffolds for the Design of Selective Estrogen Receptor Modulators," Organic & Biomolecular Chemistry, 2008, 6, pp. 3486-3496.
Jie Shen, et al., "Discovery of Potent Ligands for Estrogen Receptor β by Structure-Based Virtual Screening," Journal of the Medicinal Chemistry, 2010, 53, pp. 5361-5365.
Dale C. Leitman et al., "MF101: A Multi-Component Botanical Selective Estrogen Receptor Beta Modulator for the Treatment of Menopausal Vasomotor Symptoms," Expert Opinion in Investigational Drugs, 2012, 21(7), pp. 1031-1042.
Xiao-Ning Wang, MD, et al., "Lasofoxifene Enhances Vaginal Mucus Formation Without Causing Hypertrophy and Increases Estrogen Receptor β and Androgen Receptor in Rats," Menopause: The Journal of the North American Menopause Society, 2006, 13(4), pp. 669-620.
Notification Concerning Transmittal of International Preliminary Report on Patentability (Chapter I of the Patent Cooperation Treaty) dated Dec. 29, 2011, International Preliminary Report on Patentability, and Written Opinion of the International Searching Authority in corresponding International Application No. PCT/CA2010/000898.
Written Opinion of the International Searching Authority and International Search Report dated Oct. 26, 2010 in corresponding International Application No. PCT/CA2010/000898.
Fernand Labrie, "Drug Insight: breast cancer prevention and tissue-targeted hormone replacement therapy," Endocrinology & Metabolism, vol. 3, No. 8, Aug. 2007, pp. 584-593.
DL Barton, et al., "Dehydroepiandrosterone for the treatment of hot flashes: a pilot study," Supportive Cancer Therapy, vol. 3, No. 2, Jan. 1, 2006, pp. 91-97 (abstract).

"Effect of Dehydroepiandrosterone (DHEA) on Hot Flashes in Postmenopausal Women," Website address: http://clinicaltrials.gov/ct2/show/NCT00317148, ClinicalTrials.gov, Sep. 6, 2006, pp. 1-4.
Almeida et al., Arch. Gen. Psychiatry, 65(3):283-289, (Mar. 2008).
Archer, D.F., Ostetrics & Gynecology, vol. 94, No. 4, pp. 498-503, (Oct. 1999).
Arlt, W., et al., N. Engl. J. Med., 341(14):1013-1020, (Sep. 30, 1999).
Arlt W., et al., Journal of Clinical Endocrinology & Metabolism, 86(10):4686-4692, (Oct. 2001).
Azad et al., Journal of Clinical Endocrinology & Metabolism, 88(7):3064-3068, (Jul. 2003).
Bachmann, G., et al., Fertility and Sterility, 77(4):660-5, (Apr. 2002).
Bardon, S., et al., Journal of Clinical Endocrinology & Metabolism, 60(4):692-697, (1985).
Basson, R., "A new Model of Female Sexual Desire". The Endocrine Society: Endocrine News: 2004, http://www.endo-society.org/news/endocrine_news/2004/AndrogenTherapyAudiocinferenceReport.cfm.
Baulieu, E.E., Acta Paediatr Suppl, 1999. 433:78-80 (1999).
Bélanger, A., M. Brochu, and J. Cliche, J. Clin. Endocrinol. Metab., vol. 62, No. 5, pp. 812-815 (1986).
Benz, D.J., et al., Endocrinology, vol. 128, No. 6, pp. 2723-2730, (1991).
Berger, L., et al., "Effects of dehydroepiandrosterone, Premarin and Acolbifene on histomorphology and sex steroid receptors in the rat vagina", J Steroid Biochem Mol Biol, 96, pp. 201-215, (2005).
Burger, H.G., et al., Maturitas, 6,, pp. 351-358, (1984).
Casson, P.R., et al., Am. J. Obstet. Gynecol., vol. 169, No. 6, pp. 1536-1539, (Dec. 1993).
Cefalu, W.T., et al., Metabolism, vol. 44, No. 7), pp. 954-959, (Jul. 1995).
Chen et al., Endocrinology, 147, pp. 5303-5313, (Aug. 17, 2006).
Clarke, C.L. and R.L. Sutherland, Endocrine Reviews, 11, p. 266-301, (May 1990).
Cleary, M.P. and J. Zisk, International Journal of Obesity, 10, pp. 193-204 (1986).
Colditz, G.A., et al., N. Engl. J. Med., vol. 332, No. 24, pp. 1589-1593, (Jun. 15, 1995).
Coleman, D.L., E.H. Leiter, and R.W. Schwizer, Diabetes, vol. 31, pp. 830-833 (Sep. 1982).
Couillard, S., et al., J. Natl. Cancer Inst., vol. 90 No. 10, Reports, pp. 772-778 (1998).
Dauvois, S., et al., Breast Cancer Res. Treat., 14: 299-306, (1989).
Dauvois, S., et al., Eur. J. Cancer Clin. Oncol., vol. 25, No. 5, pp. 891-897, (1989).
Dauvois, S., et al., Cancer Res., 51, pp. 3131-3135 (Jun. 15, 1991).
Davis, S.R., et al., Maturitas, 21, pp. 227-236 (1995).
De Fazio, J., et al., Maturitas, 6, pp. 3-8 (1984).
Dennerstein, L., et al., Maturitas, 26, pp. 83-93 (1997).
Diamond, P., et al., J. Endocrinol., 150, pp. S43-S50 (1996).
Ferrannini E., et al., Hypertension, vol. 30, No. 5, pp. 1144-1149 (Nov. 1997).
Gallagher, A., et al., Endocrinology, vol. 133, No. 6, pp. 2787-2791 (1993).
Gelfand, M.M., Menopause, vol. 11, No. 5, pp. 505-507, (2004).
Gibbs, R.B. and Aggarwal, P., Hormones and Behavior, 34, pp. 98-111 (1998).
Goldstat, R., et al., Menopause, vol. 10, No. 5, pp. 390-398 (2003).
Gordon, G.B., L.M. Shantz, and P. Talalay, Adv. Enzyme Regul., 26, p. 355-382 (1987).
Hajszan, T., et al., Endocrinology, 148(5):1963-1967 (2007).
Han, D.H., et al., Journal of Gerontology: Biological Sciences, vol. 53A, No. 1, pp. B19-B24 (1998).
Hansen, P.A., et al., Am J Physiol Integrative Comp Physiol, 273:R1704-R1708 (1997).
Henderson, E., et al., Aids Res. Hum. Retroviruses, vol. 8, No. 5, pp. 625-631 (1992).
Henneman, P.M. and Wallach, S., AMA, Arch. Int. Med., 100, p. 715-723 (1957).
Hogervorst, E., et al., Neuroscience, vol. 101, No. 3, pp. 485-512 (2000).

(56) References Cited

OTHER PUBLICATIONS

Horwitz, K.B., *Endocr. Rev.*, vol. 13, No. 2, pp. 146-163 (1992).
Huang, J., et al., *Neuroscience Letters*, 367, 85-87, (2004).
Jordan, V.C., et al., *Breast Cancer Res. Treat.* 10:31-35, (1987).
Kapur, S.P. and A.H. Reddi, *Calcif. Tissue Int.*, 44:108-113 (1989).
Kawano, H., et al., *J Clin Endocrinol Metab*, 88(7):3190-3195, (2003).
Kopelman, P.G., *Nature*, vol. 404, p. 635-643, (Apr. 6, 2000).
Kramer, C.Y., *Biometrics*, vol. 12, No. 3, pp. 307-310, (Sep. 1956).
Kleerekoper, M. et al., *Calcif Tissue Int*, 37:594-597, (1985).
Labrie et al., *Annals of the New York Academy of Sciences*, vol. 774: 16-28, (1995).
Labrie et al., *Breast Cancer Research and Treatment*, 33:237-244, (1995).
Labrie et al., *Baillière's Clinical Endocrinology and Metabolism*, vol. 8, No. 2, pp. 451-474, Copyright 1994 by Baillière Tindall Ltd., Apr. 1994.
Labrie et al., *Proc. 9th European Testis Workshop*, "In: Signal Transduction in Testicular Cells: Basic and Clinical Aspects", Ernst Schering Research Foundation Workshop. Hansson, V., Levy, F.O. and Taskén, K. (eds.), Springer-Verlag, vol. Suppl. 2, pp. 185-218, (1996).
Labrie et al., "Physiological Changes in Dehydroepiandrosterone Are Not Reflected by Serum Levels of Active Androgens and Estrogens but of Their Metabolites: Intracrinology", *J Clin. Endocrinol. Metab.*, vol. 82, No. 8, pp. 2403-2409, (1997).
Labrie et al.,"Marked Decline in Serum Concentrations of Adrenal C19 Sex Steroid Precursors and Conjugated Androgen Metabolites During Aging", *J. Clin. Endocrinol. Metab.*, vol. 82, No. 8, p. 2396-2402 (1997).
Labrie et al., "EM-652 (SCH 57068), a third generation SERM acting as pure antiestrogen in the mammory gland and endometrium", *J. Steroid Biochem. and Mol. Bio.*,69, pp. 51-84, (1999).
Labrie et al., *J. Steroid Biochem. Mol. Biol.*, vol. 41, No. 3-8, pp. 421-435, (1992).
Labrie et al., "Science behind total androgen blockade: from gene to combination therapy", *Clin. Invest. Med.*, vol. 16:6, pp. 475-492 (1993).
Labrie et al., *Steroids*, 62:148-158, (1997).
Labrie et al., *J. Clin. Endocrinol. Metab.*, vol. 82, No. 10, pp. 3498-3505, (1997).
Labrie, C., A. Bélanger, and F. Labrie, *Endocrinology*, vol. 123, No. 3, pp. 1412-1417 (1988).
Labrie, F., "At the Cutting Edge Intracrinology",*Mol. Cell. Endocrinol.*, 78, pp. C113-C118, (1991).
Labrie, F., A. Dupont, and A. Bélanger, "Complete Androgen Blockage for the Treatment of Prostate Cancer 10", In: Important Advances in Oncology, V.T. de Vita, S. Hellman, and S.A. Rosenberg, Editors, J.B. Lippincott, Philadelphia, pp. 193-217, (1985).
Labrie, F., et al., *J. Steroid Biochem. Molec. Biol.*, vol. 43, No. 8, pp. 805-826, (1992).
Lauffenburger, T., et al., *Metabolism*, vol. 26, No. 6, pp. 589-606, (Jun. 1977).
Laumann, E.O., A. Paik, and R.C. Rosen, "Sexual Dysfunction in the United States" *JAMA*, vol. 281, No. 6, pp. 537-544, (Feb. 10, 1999).
Leblanc et al., *JAMA*, 285(11): 1489-1499, (2001).
Li et al., Breast Cancer Research and Treatment, 29, pp. 203-217, (1993).
Lobo, R.A., et al., *Fertility and Sterility*, vol. 79, No. 6, pp. 1341-1352, (Jun. 2003).
Luo, S., et al., *Endocrinology*, vol. 138, No. 10, pp. 4435-4444, (1997).
Luu-The, V. et al., *DNA and Cell Biology*, vol. 14, No. 6, pp. 511-518, (1995).
MacEwen, E.G. and I.D. Kurzman, "Obesity in the Dog: Role of the Adrenal Steroid Dehydroepiandrosterone (DHEA)", *In: The Journal of Nutrition*, 121, pp. S51-S55 ,(1991).
McEwen, B.S. and Alves, S.E., *Endocrine Reviews*, vol. 20, No. 3, pp. 279-307, (1999).

Manson et al., *Menopause*, vol. 13, No. 1, pp. 139-147 (2006).
Martel, C., et al., *J. Endocrinol.*, 157(3), pp. 433-442 (1998).
Melsen et al., *Acta Pathologica & Microbiologica Scandinavia Sect. A*, 86, pp. 70-81, (1978).
Migeon, C.J., et al., *J. Clin. Endocrinol. Metab.*, vol. 17, pp. 1051-1062, (1957).
Mohan, P.F., et al., *J. Nutr.*, 120, pp. 1103-1114, (1990).
Monk and Brodaty, "Use of estrogens for the prevention and treatment of Alzheimer's disease", *Dement. Geriatr. Cogn. Disord.*, 11, pp. 1-10, (Jan./Feb. 2000).
Morrison, et al., *J. Neurosci.*, 26 (41), pp. 10332-10348, (Oct. 11, 2006).
Musgrove, E.S., et al., *Mol. Cell. Biol.*, vol. 11, No. 10, pp. 5032-5043, (Oct. 1991).
Nathorst-Boos, J., et al., *Gynecol Obstet Invest*, 34, pp. 97-101, (1992).
Need, A.G., et al., *Arch. Intern. Med.*, vol. 149, pp. 57-60, (Jan. 1989).
Nestler, J.E., et al., J. Clin. Endocrinol. Metab., vol. 66, No. 1, pp. 57-61, (1988).
Notelovitz, M., et al. "Effect of Long-Term Treatment with Oral Esterified Estrogens (Estrone Sulfate + Equilin Sulfated on Cholesterol and Lipoprotein Levels in Postmenopausal Women", *North Am. Menopause Soc.*, Poster Presentations, p. 122, (1991).
Orentreich, N., et al., *J. Clin. Endocrinol. Metab.*, vol. 59, No. 3, pp. 551-555, (1984).
Overlie, et al., *Maturitas* 41, (2002) pp. 69-77.
Parfitt, A.M., *Calcified Tissue International*, 36 Suppl. 1, pp. S37-S45, (1984).
Poulin, R. and F. Labrie, *Cancer Res.*, 46, pp. 4933-4937 (Oct. 1986).
Poulin, R. et al., *Breast Cancer Res. Treat.*, 12, pp. 213-225 (1988).
Preston-Martin, S., et al., *Cancer. Res.* 50, pp. 7415-7421 (1990).
Pye, J.K., et al., *The Lancet*, 2, pp. 373-377, (Aug. 17, 1985).
Raisz, L.G., et al., *J Clin Endocrinol Metab*, vol. 81, No. 1, pp. 37-43, (1996).
Rasmussen, K.R., et al., *Antimicrob. Agents Chemother.*, 36, pp. 220-222, (Jan. 1992).
Rocca W.A., et al., "Survival patterns after oophorectomy in premenopausal women: a population-based cohort study", *The Lancet Oncol.*, vol. 7, pp. 821-828 (Oct. 2006).
Rocca W.A., et al., *Neurology*, 69, pp. 1074-1083, (2007).
Savvas, M., et al., Br. Med. J., vol. 297, pp. 331-333, (Jul. 30, 1988).
Schriock, E.D., et al., *J. Clin. Endocrinol. Metab.*, vol. 66, No. 6, pp. 1329-1331 (1988).
Schwartz, A.G., *Toxicol. Pathol.*, vol. 14, No. 3, pp. 357-362, ISSN:0192-6233, (1986).
Sherwin, B.B. et al., *Am. J. Obstet. Gynecol.*, vol. 148, No. 5, pp. 552-557, Mar. 1, 1984).
Sherwin, B.B. et al., *Am. J. Obstet. Gynecol.*, vol. 151, No. 2, p. 153-160, (Jan. 15, 1985).
Sherwin, B.B. and M.M. Gelfand, *Psychosom Med.*, 49, pp. 397-409 (1987).
Sherwin, B.B., *J. Affect. Disord.*, 14, pp. 177-187, (1988).
Shifren, J.L., et al., *The New England Journal of Medicine*, vol. 343, No. 10, pp. 682-688, (Sep. 7, 2000).
Shimokata, H., et al., *J Gerontol*, vol. 44, No. 2, pp. M66-M73, (1989).
Sibonga, J.D., et al., *Breast Cancer Research and Treatment*, 41, pp. 71-79, (1996).
Simard, J., et al., *Int. J. Cancer*, 73, pp. 104-112, (1997).
Sourla, A., et al., *J. Steroid Biochem. Mol. Biol.*, vol. 66, No. 3, pp. 137-149, (1998).
Stomati, M., et al., *Gynecol. Endocrinol.*, 14(5), pp. 342-363, (2000).
Studd, J.W., et al.,. *Br. J. Obstet. Gynecol.*, vol. 84, pp. 314-315, (1977).
Suzuki, T., et al., . *Clin. Immunol. Immunopathol.*, 61, pp. 202-211, (1991).
Tchernof, A., et al., *Metabolism*, vol. 44, No. 4, pp. 513-519, (Apr. 1995).
Tchernof, A., Labrie, F., Bélanger, A., and Després, J.P.,*J. Endocrinol.*, 150, pp. S155-S164, (1996).

(56) References Cited

OTHER PUBLICATIONS

Vermeulen, A. and L. Verdonck, *J. Steroid Biochem.*, vol. 7, pp. 1-10, (1976).
Vermuelen, A., et al., *J. Clin. Endocrinol. Metab.*, vol. 54, No. 1, pp. 187-191, (1982).
Villareal, D.T. and J.O. Holloszy,*JAMA*, vol. 292, No. 18, pp. 2243-2248, (Nov. 10, 2004).
Wakeling, A.E. *Breast Cancer Res. Treat.*, 25, pp. 1-9, (1993).
Weinstein and Hutson, *Bone*, 8, pp. 137-142, (1987).
Willson at al., *Endocrinology*, vol. 138, No. 9, pp. 3901-3911, (1997).
Writing Group for the Women's Health Initiative Investigators, *JAMA*, vol. 288, No. 3, pp. 321-333, (2002).
Xu et al., *Nat. Med.*, vol. 4, No. 4, pp. 447-451, (Apr. 1998).
Yen, T.T., et al., *Lipids*, vol. 12, No. 5, pp. 409-413, (1977).
Yaffe, K., et al., *JAMA*, vol. 279, pp. 688-695, (Mar. 4, 1998).
Zumoff, B., et al., *Cancer Res.*, vol. 41, pp. 3360-3363 (1981).
Labrie et al., Third- and Fourth-Generation SERMs in Manni A., Verderame M., "Selective estrogen receptor modulators: research and clinical applications," Totowa, NJ, Humana Press Inc. (2002), p. 167-187.
Liu et al., Bioactivation of the selective estrogen receptor modulator acolbifene to quinone methides. Chem. Res. Toxicol. 2005, 18, pp. 174-182.
"Structure-Activity Relationship and Drug Design," Remington's Pharmaceutical Sciences (Sixteenth Edition). Mack Publishing, 1980, pp. 420-425.
Berge et al., "Pharmaceutical Salts," Journal of Pharmaceutical Sciences, 66(1); 1977, pp. 1-19.
Adelson et al., "Treatment of hot flushes in breast and prostate cancer," Expert Opin. Pharmacother. 2005, 6(7), pp. 1095-1106.
Extended European Search Report dated May 24, 2013 in corresponding European Application No. 10788551.9.
Martel, C., et al.: "Prevention of bone loss by EM-800 and raloxifene in the ovariectomized rat", *The Journal of Steroid Biochemistry and Molecular Biology*, vol. 74, No. 1-2, Sep. 2000, pp. 45-56, XP002695199, ISSN: 0960-0760.
Picard, F., et al.: "Effects of the estrogen antagonist EM-652.HC1 on energy balance and lipid metabolism in ovariectomized rats", *International Journal of Obesity and Related Metabolic Disorders: Journal of the International Association for the Study of Obesity*, vol. 24, No. 7, Jul. 2000, pp. 830-840, XP002695200, ISSN: 0307-0565.
Littleton-Kearney, M. et al.: "Selective Estrogen Receptor Modulators: Tissue Actions and Potential for CNS Protection", *CNS Drug Reviews*, vol. 8, No. 3, 2002, pp. 309-330, XP001145878, Branford, CT, US, ISSN: 1080-563X.
Elledge, et al: "1-43 Activity and Safety of the Antiestrogen EM-800, the Orally Active Precursor of Acolbifene, in Tamoxifen-Resistant Breast Cancer", *Breast Diseases: A Year Book Quarterly*, vol. 16, No. 1, Apr. 1, 2005, pp. 82-83, XP005210073, ISSN: 1043-321X, DOI: 10.1016/S1043-321X(05)80067-0.
Labrie, F.: "Future Perspectives of Selective Estrogen Receptor Modulators Used Alone and in Combination with DHEA", *Endocrine-Related Cancer*, (2006), 13, pp. 335-355, DOI:10.1677/erc.1.00883, 1351-0088/06/013-335 © 2006 Society for Endocrinology, Online version via http://www.endocrinology-journals.org.
"A Textbook of Drug Design and Development," Edited by Povl Krogsgaard-Larsen and Hans Bundgaard, Harwood Academic Publishers GmbH, pp. 114-190, 1991.
Sylvain Gauthier, et al., "(S)-(+)-4-[7-(2,2-Dimethyl-1-oxopropoxy)-4-methyl-2-[4-[2-(1-piperidinyl)-ethoxy]phenyl]-2H-1-benzopyran-3-yl]-phenyl 2,2-Dimethylpropanoate (EM-800): A Highly Potent, Specific, and Orally Active Nonsteroidal Antiestrogen," J. Med. Chem., 40, pp. 2117-2122, 1997.
Steven R. Goldstein, et al., "A Pharmacological Review of Selective Oestrogen Receptor Modulators," Human Reproduction Update, vol. 6, No. 3, pp. 212-224, 2000.
CK Osborne, et al., "Fulvestrant: An Oestrogen Receptor Antagonist With a Novel Mechanism of Action," British Journal of Cancer, 90 (Supp 1), pp. S2-S6, 2004.
F. Labrie, et al., Starling Review, "Is Dehydroepiandrosterone a Hormone?," Journal of Endocrinology, 187, pp. 169-196, 2005.
C. Labrie, et al., "High Bioavailability of Dehydroepiandrosterone Administered Percutaneously in the Rat," Journal of Endocrinology, 150, S107-S118, 1996.
Claude Labrie, et al., "Stimulation of Androgen-Dependent Gene Expression by the Adrenal Precursors Dehydroepiandrosterone and Androstenedione in the Rat Ventral Prostate," Endocrinology, vol. 124, No. 6, pp. 2745-2754, 1989.
Etienne-Emile Baulieu, et al., "Dehydroepiandrosterone (DHEA), DHEA Sulfate, and Aging: Contribution of the DHEAge Study to a Sociobiomedical Issue," PNAS, vol. 97, No. 8, pp. 4279-4284, Apr. 11, 2000.
Richard F. Spark, "Dehydroepiandrosterone: A Springboard Hormone for Female Sexuality," Fertility and Sterility, vol. 77, No. 4, Suppl. 4, pp. S19-S25, Apr. 2002.
Fernand Labrie, "DHEA, important source of sex steroids in men and even more in women," Progress in Brain Research, vol. 182, Chapter 4, pp. 97-148 (2010).
Philipp Y. Maximov, et al., "The Discovery and Development of Selective Estrogen Receptor Modulators (SERMs) for Clinical Practice,"Current Clinical Pharmacology, vol. 8, pp. 135-155 (2013).
Bauke Buwalda, et al., Is basic research providing answers if adjuvant anti-estrogen treatment of breast cancer can induce cognitive impairment?, Life Sciences, vol. 93, pp. 581-588 (2013).
Tibolone—Wikipedia—N:\wdox\CLIDOCS\001259\01202\01634562. MHT (4 pages).
Wulf H. Utian, "Recent Developments in Pharmacotherapy for Vasomotor Symptoms," Curr. Obstet. Gynecol. Rep. (2012), 1, pp. 43-49.
Peter D. Alfinito, et al., "ICI 182,780 Penetrates Brain and Hypothalamic Tissue and Has Functional Effects in the Brain After Systemic Dosing," Endocrinology, vol. 149, No. 10, 2008, pp. 5219-5226.
Olivier Barbier, et al., "Glucuronidation of the Nonsteroidal Antiestrogen EM-652 (SCH 57068), by Human and Monkey Steroid Conjugating UDP-Glucuronosyltransferase Enzymes," Molecular Pharmacology, vol. 59, No. 3, 2001, pp. 636-645.
Ernst A. Lien, et al., "Distribution of Tamoxifen and Metabolites Into Brain Tissue and Brain Metastases in Breast Cancer Patients," Br. J. Cancer, vol. 63, 1991, pp. 641-645.
Ernst A. Lien, et al., "Distribution of Tamoxifen and Its Metabolites in Rat and Human Tissues During Steady-State Treatment," Cancer Research, vol. 51, Sep. 15, 1991, pp. 4837-4844.
Zhaoyong Yang, et al., "The Determination of Raloxifene in Rat Tissue Using HPLC," Biomedical Chromatography, vol. 21, 2007, pp. 229-233.
Notice of Reasons for Rejection dated Jan. 26, 2015 in corresponding Japanese Patent Application No. 2014-025183 (with English language translation)(10 pages).
Rena Li, et al., "Brain Sex Matters: Estrogen in Cognition and Alzheimer's Disease," Molecular and Cellular Endocrinology, 389 (2014), pp. 13-21.
Carol J. Fabian, et al., "Clinical Trial of Acolbifene in Premenopausal Women at High Risk for Breast Cancer," Cancer Prevention Research, vol. 8, No. 12, pp. 1146-1155 (2015).
Fernand Labrie, et al., "Activity and Safety of the Antiestrogen EM-800, the Orally Active Precursor of Acolbifene, in Tamoxifen-Resistant Breast Cancer," Journal of Clinical Oncology, vol. 22, No. 5, pp. 864-871 (2004).
Délio M. Conde, MD, et al., "Menopause Symptoms and Quality of Life in Women Aged 45 to 65 Years With and Without Breast Cancer," Menopause: The Journal of the North American Menopause Society, vol. 12, No. 4, pp. 436-443 (2005).
Janet S. Carpenter, et al., "Hot Flashes in Postmenopausal Women Treated for Breast Carcinoma," Cancer, vol. 82, No. 9, pp. 1682-1691 (1998).
Deirdre R. Pachman, et al., "Management of Menopause-Associated Vasomotor Symptoms: Current Treatment Options, Chal-

(56) References Cited

OTHER PUBLICATIONS lenges and Future Directions," International Journal of Women's Health, vol. 2, pp. 123-135 (2010).
Juergen Drewe, et al., "A Systematic Review of Non-Hormonal Treatments of Vasomotor Symptoms in Climacteric and Cancer Patients," SpringerPlus, vol. 4, No. 65, pp. 1-29 (2015).
Gerrie-Cor M. Gast, Ph.D., et al., "Vasomotor Menopausal Symptoms are Associated With Increased Risk of Coronary Heart Disease," Menopause: The Journal of the North American Menopause Society, vol. 18, No. 2, p. 146-151 (2011).
Rebecca C. Thurston, et al., "Gains in Body Fat and Vasomotor Symptom Reporting Over the Menopausal Transition," American Journal of Epidemiology, vol. 170, No. 6, pp. 766-774 (2009).
Scheffers CS, et al., "Dehydroepiandrosterone for Women in the Peri- or Postmenopausal Phase (Review)," Cochrane Database of Systematic Reviews, Issue 1, Art. No. CD011066, DOI: 10.1002/14651858.CD011066.pub2, pp. 1-118 (2015).
Victor W. Henderson, et al., "Raloxifene for Women with Alzheimer Disease," Neurology, American Academy of Neurology, vol. 85, 2015, pp. 1937-1944.
Notice of Reasons for Rejection dated Oct. 7, 2016 in corresponding Japanese Patent Application No. 2015-20350 (with English language translation)(13 total pages).
Notice of Reasons for Rejection dated Oct. 17, 2016 in corresponding Japanese Patent Application No. 2015-223062 (with English language translation)(16 total pages).
D. F. Archer, et al., "Menopausal Hot Flushes and Night Sweats: Where Are We Now?," Climacteric, vol. 14, No. 5, 2011, pp. 515-528.
William R. Good, Ph.D., et al., "Double-Masked, Multicenter Study of an Estradiol Matrix Transdermal Delivery System (Alora™) Versus Placebo in Postmenopausal Women Experiencing Menopausal Symptoms," Clinical Therapeutics, vol. 18, No. 6, 1996, pp. 1093-1105.
H. Hassa, et al., "Is Placebo as Effective as Estrogen Regimens on Vasomotor Symptoms in Women With Surgical Menopause?," Clin. Exp. Obst. & Gyn., vol. 37, No. 2, 2010, pp. 135-137.
MacLennan A.H., et al., "Oral Oestrogen and Combined Oestrogen/Progestogen Therapy Versus Placebo for Hot Flushes (Review)," Cochrane Database Systematic Reviews, Issue 4, Art. No. CD002978, 2004, pp. 1-56.
Todd R. Marcy, et al., "Antidepressant-Induced Sweating," Ann. Pharmacother., vol. 39, No. 4, 2005, pp. 748-752.
J. A. Simon, et al., "Perimenopausal Women in Estrogen Vasomotor Trials: Contribution to Placebo Effect and Efficacy Outcome," Climacteric, 4, 2001, pp. 19-27.
M. Stomati, et al, "Six-Month Oral Dehydroepiandrosterone Supplementation in Early and Late Postmenopause," Gynecological Endocrinology, vol. 14, No. 5, 2000, pp. 342-363.
Danielle Murray, et al., "Mechanisms and Therapeutic Implications of the Placebo Effect in Neurological and Psychiatric Conditions," Pharmacology & Therapeutics, vol. 140, (2013), pp. 306-318.
Robert Lindsay, Ph.D., et al., "Efficacy of Tissue-Selective Estrogen Complex of Bazedoxifene/Conjugated Estrogens for Osteoporosis Prevention in At-Risk Postmenopausal Women," Fertility and Sterility, vol. 92, No. 3, Sep. 2009, pp. 1045-1052.
Nobuhide Watanabe, et al., "Discovery and Preclinical Characterization of (+)-3-[4-(1-Piperidinoethoxy)phenyl]spiro[indene-1,1'-indane]-5,5'-diol Hydrochloride: A Promising Nonsteroidal Estrogen Receptor Agonist for Hot Flush," J. Med. Chem. 2003, vol. 46, pp. 3961-3964.
Grimley Evans J. et al., "Dehydroepiandrosterone (DHEA) Supplementation for Cognitive Function in Healthy Elderly People (Review)," (2006) Cochrane Database of Systematic Reviews, Issue 4. Art. No. CD006221, 54 pages.
Karina Junqueira de Menezes, "Dehydroepiandrosterone, Its Sulfate and Cognitive Functions," Clinical Practice & Epidemiology in Mental Health, 2016, vol. 12, pp. 24-37.

Extended Search Report and Opinion dated Apr. 24, 2017 in corresponding European Patent Application No. 17151727.9 (22 total pages).
L C Swartzman, et al., "Impact of Stress on Objectively Recorded Menopausal Hot Flushes and on Flush Report Bias," Health Psychology: Official Journal of the Division of Health Psychology, American Psychological Association, 1990, vol. 9, No. 5, pp. 529-545: ISSN: 0278-6133 (Abstract).
Yasui Toshiyuki, et al., "Hormone Replacement Therapy in Postmenopausal Women," Journal of Medical Investigation, vol. 50, No. 3-4, Aug. 2003, pp. 136-145, ISSN: 1343-1420 (Abstract).
Ana Aranda, et al., Nuclear Hormone Receptors and Gene Expression, Jul. 2001, Physiological Reviews, vol. 81, No. 3, pp. 1269-1304.
Davis D.H.J., et al., "Montreal Cognitive Assessment for the Diagnosis of Alzheimer's Disease and Other Dementias (Review)," 2015, Cochrane Database of Systematic Reviews, 10, CD 010775, 42 total pages.
W. Vallen Graham, et al., "Update on Alzheimer's Disease Therapy and Prevention Strategies," 2017, Annu. Rev. Med., 68, pp. 413-430.
Marilyn M. Miller, et al., "Estrogen Replacement Therapy for the Potential Treatment or Prevention of Alzheimer's Disease," 2001, Ann. N.Y. Acad. Sci., 949, pp. 223-234.
Christian J. Pike, et al., "Androgens, Aging, and Alzheimer's Disease," 2006, Endocrine, vol. 29, No. 2, pp. 233-241.
Henrik Zetterberg, "Applying Fluid Biomarkers to Alzheimer's Disease," Apr. 19, 2017, Am J Physiol Cell Physiol, total 21 pages.
Mohan Giri, et al., "Genes Associated With Alzheimer's Disease: An Overview and Current Status," 2016, Clinical Interventions in Aging, vol. 11, pp. 665-681.
Mina Park, MD, et al., "Structural MR Imaging in the Diagnosis of Alzheimer's Disease and Other Neurodegenerative Dementia: Current Imaging Approach and Future Perspectives," 2016, Korean Journal of Radiology, vol. 17, No. 6, pp. 827-845.
O. M. Wolkowitz, et al., "DHEA Treatment of Alzheimer's Disease," 2003, Neurology, vol. 60, No. 7, pp. 1071-1076.
Lynnette Leidy Sievert, et al., "Determinants of Hot Flashes and Night Sweats," Annals of Human Biology, Jan.-Feb. 2006, vol. 33, No. 1, pp. 4-16.
Roslyn D. Taylor, M.D., "Common Causes of Night Sweats in Various Populations," Am. Fam. Physician, Oct. 1, 2003, vol. 68, No. 7, p. 1264.
Fernand Labrie, et al., "Metabolism of DHEA in Postmenopausal Women Following Percutaneous Administration," Journal of Steroid Biochemistry & Molecular Biology, 103, (2007), pp. 178-188.
Fernand Labrie, et al., "Effect of Intravaginal DHEA on Serum DHEA and Eleven of its Metabolites in Postmenopausal Women," Journal of Steroid Biochemistry & Molecular Biology, 111, (2008), pp. 178-194.
Fernand Labrie, et al., "Science of Intracrinology in Postmenopausal Women," Menopause: The Journal of the North American Menopause Society, vol. 24, No. 6, (2017) pp. 702-712.
Fernand Labrie, "At the Cutting Edge, Intracrinology," Molecular and Cellular Endocrinology, 78, (1991), pp. C113-C118.
Fernand Labrie, et al., "Bioavailability and Metabolism of Oral and Percutaneous Dehydroepiandrosterone in Postmenopausal Women," Journal of Steroid Biochemistry & Molecular Biology, 107, (2007), pp. 57-69.
Fernand Labrie, et al., "Changes in Serum DHEA and Eleven of its Metabolites During 12-Month Percutaneous Administration of DHEA," Journal of Steroid Biochemistry & Molecular Biology, 110, (2008), pp. 1-9.
Fernand Labrie, et al., Corrigendum to "Effect of Intravaginal DHEA on Serum DHEA and Eleven of its Metabolites in Postmenopausal Women" [Journal of Steroid Biochemistry and Molecular Biology (2008) 178-194], Journal of Steroid Biochemistry & Molecular Biology, 112, (2008), p. 169.
Decision of Rejection dated Jun. 4, 2018 in corresponding Japanese Patent Application No. 2015-223062 (13 total pages).
JoAnn V. Pinkerton, MD, et al., "Relief of Vasomotor Symptoms with the Tissue-Selective Estrogen Complex Containing Bazedoxifene/

(56) References Cited

OTHER PUBLICATIONS

Conjugated Estrogens: A Randomized, Controlled Trial," Menopause: The Journal of the North American Menopause Society, vol. 16, No. 6, 2009, pp. 1116-1124.

Owen B. Wallace, et al., "A Selective Estrogen Receptor Modulator for the Treatment of Hot Flushes," J. Med. Chem., 2006, vol. 49, pp. 843-846.

Ivanna V. Tataryn, et al., "LH, FSH and Skin Temperature During the Menopausal Hot Flash," (1979), Journal of Clinical Endocrinology and Metabolism, vol. 49, No. 1, pp. 152-154.

R. F. Casper, et al., "Menopausal Flushes: A Neuroendocrine Link With Pulsatile Luteinizing Hormone Secretion," (1979), Science, vol. 205, pp. 823-825.

Christian Lemieux, et al., "The Estrogen Antagonist EM-652 and Dehydroepiandrosterone Prevent Diet- and Ovariectomy-Induced Obesity," (2003), Obesity Research, vol. 11, No. 3, pp. 477-490.

Kentaro Takahashi, et al., "Efficacy and Safety of Oral Estriol for Managing Postmenopausal Symptoms," (2000), Maturitas, vol. 34, pp. 169-177.

Jennifer Shi, et al., "The Effect of 7-oxo-DHEA Acetate on Memory in Young and Old C57BL/6 Mice," (2000), Steroids, 65, pp. 124-129.

\* cited by examiner

FIG. 4
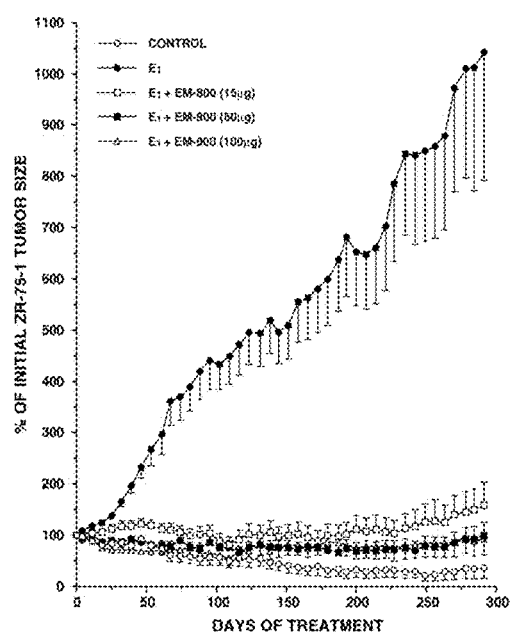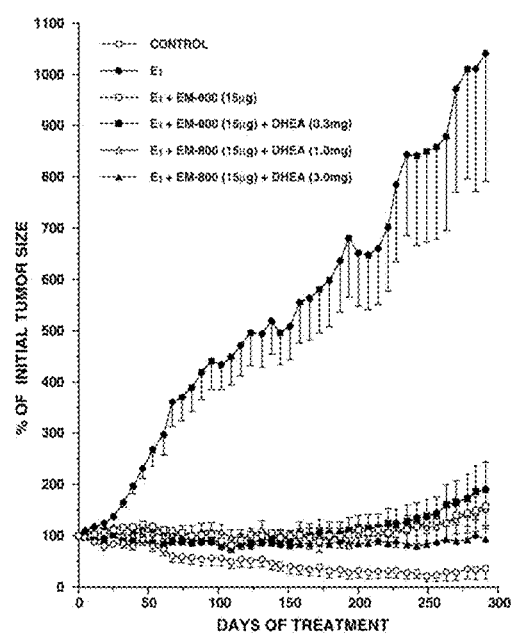

FIG. 10
A
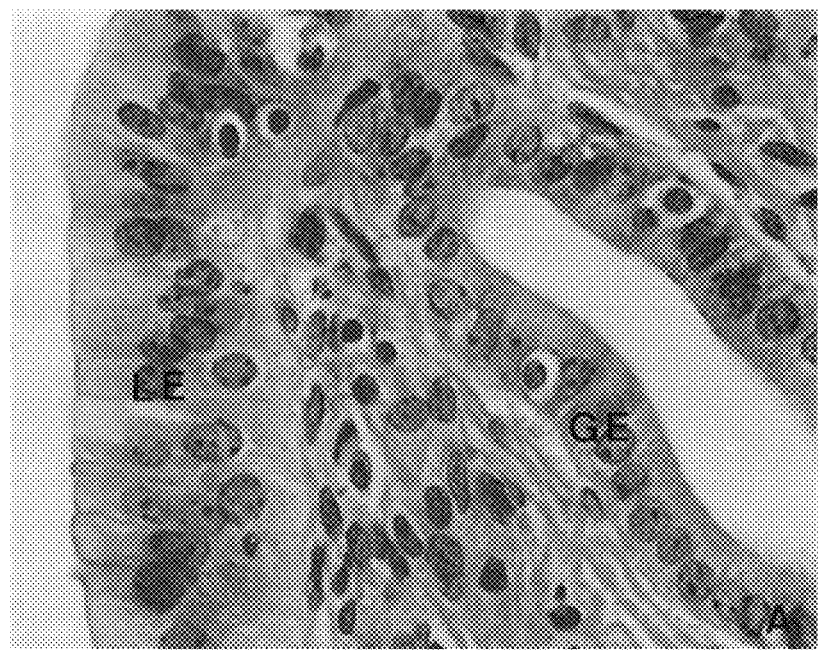
B
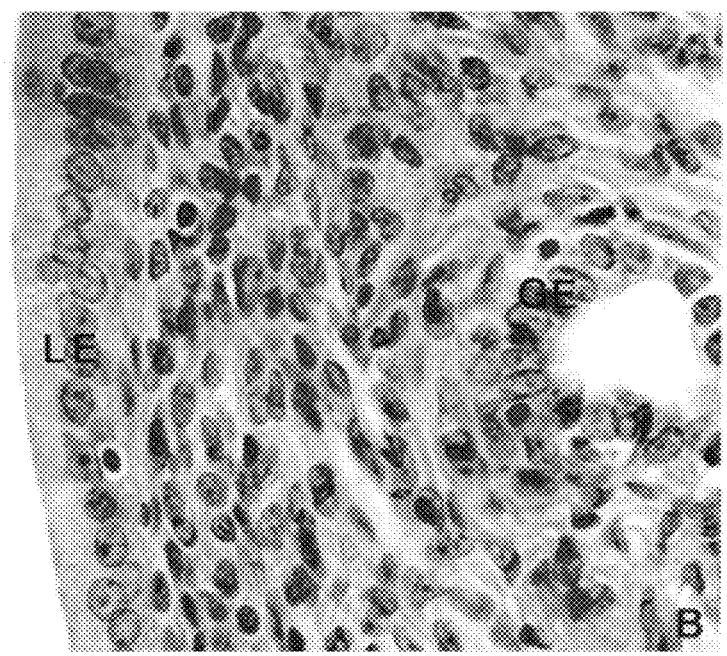

STUDY DESIGN DIAGRAM

[a] Informed consent must be obtained prior to the performance of any study related procedures.

TREATMENT OF ALZHEIMER'S DISEASE, LOSS OF COGNITION, MEMORY LOSS AND DEMENTIA WITH SEX STEROID PRECURSORS IN COMBINATION WITH SELECTIVE ESTROGEN RECEPTOR MODULATORS

CROSS REFERENCE TO RELATED APPLICATIONS

The present application is a divisional patent application of prior U.S. patent application Ser. No. 12/791,174, filed Jun. 1, 2010, which claims priority under 35 U.S.C. § 119 of U.S. Provisional Patent Application Ser. No. 61/187,549, filed Jun. 16, 2009, the contents of which are all incorporated herein by reference.

FIELD OF THE INVENTION

The present invention relates to a new treatment for hot flushes, vasomotor symptoms, and night sweats in women. In particular, the treatment includes the administration of a precursor of sex steroids in combination with a selective estrogen receptor modulator (SERM) for reducing the risk of acquiring breast or endometrial cancer. The invention also provides kits and pharmaceutical compositions for practicing the foregoing combination. Administration of the foregoing combination to patients reduces or eliminates the incidence of hot flushes, vasomotor symptoms, night sweats, and sleep disturbance. Moreover, the risk of acquiring breast cancer and/or endometrial cancer is believed to be reduced for patients receiving this combination therapy. Additional benefits such as reduction of the likelihood or risk of acquiring osteoporosis, hypercholesterolemia, hyperlipidemia, atherosclerosis, hypertension, Alzheimer's disease, loss of cognition, loss of memory, insomnia, cardiovascular diseases, insulin resistance, diabetes, and obesity (especially abdominal obesity) are also provided.

BACKGROUND

Related Art

Set forth below are full citations of references discussed infra herein using more abbreviated citation format.
Almeida et al., Arch. Gen. Psychiatry, 2008, 65, 283-289.
Arlt, W., et al., N. Engl. J. Med., 1999. 341(14): p. 1013-1020.
Arlt, W., et al., J Clin Endocrinol Metab, 2001. 86(10): p. 4686-92.
Azad et al., J., Clin. End. Metab., 2003, 88, 3064-3068.
Bachmann, G., et al., Fertil Steril, 2002. 77(4): p. 660-5.
Bardon, S., et al., J. Clin. Endocrinol. Metab., 1985. 60: p. 692-697.
Basson, R., Endocrine News, 2004. 29: p. 22.
Baulieu, E. E., Acta Paediatr Suppl, 1999. 88(433): p. 78-80.
Bélanger, A., M. Brochu, and J. Cliche, J. Clin. Endocrinol. Metab., 1986. 62: p. 812-815.
Benz, D. J., et al., Endocrinology, 1991. 128: p. 2723-2730.
Berger, L., et al., Effects of dehydroepiandrosterone, Premarin and Acolbifene on histomorphology and sex steroid receptors in the rat vagina. J Steroid Biochem Mol Biol, 2005. 96(2): p. 201-15.
Burger, H. G., et al., Maturitas, 1984. 6: p. 351-358.
Casson, P. R., et al., Am. J. Obstet. Gynecol., 1993. 169: p. 1536-1539.
Cefalu, W. T., et al., Metabolism, 1995. 44(7): p. 954-9.
Chen et al., Endocrinology, 2006, 147, 5303-5313
Clarke, C. L. and R. L. Sutherland, Endocr. Rev., 1990. 11: p. 266-301.
Cleary, M. P. and J. Zisk, Int. J. Obes., 1986. 10: p. 193-204.
Colditz, G. A., et al., N. Engl. J. Med., 1995. 332: p. 1589-1593.
Coleman, D. L., E. H. Leiter, and R. W. Schwizer, Diabetes, 1982. 31: p. 830-833.
Couillard, S., et al., J. Natl. Cancer Inst., 1998. 90(10): p. 772-778.
D. F. Archer, K. Furst, D. Tipping, M. P. Dain, C. Vandepol, Obstet. Gynecol. 94 (1999) 498-503.
Dauvois et al., Breast Cancer Res. Treat. 14: 299-306, 1989a.
Dauvois et al., Eur. J. Cancer Clin. Oncol. 25: 891-897, 1989b.
Dauvois, S., et al., Cancer Res., 1991. 51: p. 3131-3135.
Davis, S. R., et al., Maturitas, 1995. 21(3): p. 227-36.
De Fazio, J., et al., Maturitas, 1984. 6: p. 3-8.
Dennerstein, L., et al., Maturitas, 1997. 26(2): p. 83-93.
Diamond, P., et al., J. Endocrinol., 1996. 150: p. S43-550.
Ferrannini, E., et al., Hypertension, 1997. 30(5): p. 1144-9.
Gallagher et al., Endocrinology 133: 2787-2791, 1993.
Gelfand, M. M., Menopause, 2004. 11(5): p. 505-7.
Gibbs and Aggamal, 1998
Goldstat, R., et al., Menopause, 2003. 10(5): p. 390-8.
Gordon, G. B., L. M. Shantz, and P. Talalay, Adv. Enzyme Regul., 1987, 26: p. 355-382.
Hajszan et al., Endocrinology, 2007, 148 (5), 1963-1967.
Han, D. H., et al., J Gerontol A Biol Sci Med Sci, 1998. 53(1): p.
Hansen, P. A., et al., Am J Physiol, 1997. 273(5 Pt 2): p. R1704-8.
Henderson, E., J. Y. Yang, and A. Schwartz, Aids Res. Hum. Retroviruses, 1992. 8: p. 625-631.
Hennernan, P. M. and S. Wallach, AMA: Arch. Int. Med., 1957. 100: p. 715-723.
Hogovorst et al., Neuroscience, 2000, 101, 485-512.
Horwitz, K. B., Endocr. Rev., 1992. 13: p. 146-163.
Huang et al., Neurosci. Lett, 2004, 367, 85-87
Jordan et al., Breast Cancer Res. Treat. 10: 31-35, 1987.
Kapur, S. P. and A. H. Reddi, Calcif. Tissue Int., 1989. 44: p. 108-113.
Kawano, H., et al., J Clin Endocrinol Metab, 2003. 88(7): p. 3190-5.
Kopelman, P. G., Nature, 2000. 404(6778): p. 635-43.
Kramer C Y; Biometrics 1956; 12:307-310).
Labrie et al.: Intracrinology. Ann. N.Y. Acad. Sci., 774: 16-28, 1995a.
Labrie et al., Breast Cancer Res. Treat. 33: 237-244, 1995b.
Labrie et al., Enzymes and Receptors. Sheppard, M. C. and Stewart, P. M. (eds.), London, Baillière's Clinical Endocrinology and Metabolism, Bailliere Tindall Ltd.: pp. 451-474, 1994.
Labrie et al., In: Signal Transduction in Testicular Cells. Ernst Schering Research Foundation Workshop. Hansson, V., Levy, F. O. and Tasken, K. (eds.), Berlin, Heidelberg, New York, Springer-Verlag, Vol. Suppl. 2: pp. 185-218, 1996.
Labrie et al., J. Clin. Endocrinol. Metab., 1997a. 82(8): p. 2403-2409.
Labrie et al., J. Clin. Endocrinol. Metab., 1997b. 82: p. 2396-2402.
Labrie et al., J. Steroid Biochem. and Mol. Bio. 69, 51-84, 1999
Labrie et al., J. Steroid Biochem. Mol. Biol., 41: 421-435, 1992b.

Labrie et al., Science behind total androgen blockade: from gene to combination therapy. Clin. Invest. Med., 1993. 16: p. 475-492.
Labrie et al., Steroids, 62: 148-158, 1997d.
Labrie et al., J. Clin. Endocrinol. Metab., 82: 3498-3505, 1997c.
Labrie, C., A. Bélanger, and F. Labrie, Endocrinology, 1988. 123: p. 1412-1417.
Labrie, F. Intracrinology. Mol. Cell. Endocrinol., 78: C113-C118, 1991.
Labrie, F., A. Dupont, and A. Bélanger, V. T. de Vita, S. Hellman, and S. A. Rosenberg, Editors. 1985, J.B. Lippincott: Philadelphia. p. 193-217.
Labrie, F., Simard, J., Luu—The, V., Bélanger, A., and Pelletier, G. J. Steroid Biochem. Mol. Biol., 43: 805-826, 1992a.
Lauffenburger T et al., Metabolism. 1977 June; 26(6):589-606.
Laumann, E. O., A. Paik, and R. C. Rosen, Jama, 1999. 281(6): p. 537-44.
Leblanc et al., JAMA, 2001, 285, 1489-1499.
Li et al., Breast Cancer Res. Treat., 1993. 29: p. 203-217.
Lobo, R. A., et al., Fertil Steril, 2003. 79(6): p. 1341-52.
Luo, S., et al., Endocrinology, 1997. 138: p. 4435-4444.
Luu—The, V., Dufort, I., Paquet, N., Reimnitz, G., and Labrie, F., DNA Cell Biol., 14: 511-518, 1995a.
MacEwen, E. G. and I. D. Kurzman, J. Nutr., 1991. 121: p. S51-S55.
Mc Ewen B S and Alves S E, Endocr. Rev., 1999, 20, 279-307.
Manson et al., Menopause, 2006, 13, 139-147.
Martel, C., et al., J. Endocrinol., 1998. 157(3): p. 433-442.
Melsen et al., Acta Pathologica & Microbiologica Scandinavia 86: 70-81, 1978.
Migeon, C. J., et al., J. Clin. Endocrinol. Metab., 1957. 17: p. 1051-1062.
Mohan, P. F., et al., J. Nutr., 1990. 120: p. 1103-1114.
Monk and Brodatz, Dement. Geriatr. Cogn. Disord., 2000, 11, 1-10.
Morrison et al., J. Neurosci., 2006, 26 (41), 10332-10348.
Musgrove, E. S., C. S. Lee, and R. L. Sutherland, Mol. Cell. Biol., 1991. 11: p. 5032-5043.
Nathorst-Boos, J. and B. von Schoultz. Gynecol Obstet Invest, 1992. 34(2): p. 97-101.
Need, A. G., et al., Arch. Intern. Med., 1989. 149: p. 57-60.
Nestler, J. E., et al., J. Clin. Endocrinol. Metab., 1988. 66: p. 57-61.
Notelovitz, M., et al. in *North Am. Menopause Soc.* 1991. Montreal.
Orentreich, N., et al., J. Clin. Endocrinol. Metab., 1984. 59: p. 551-555.
Overlie, et al. Maturitas 41, (2002) 69-77.
Parfitt, Calcified Tissue International 36 Suppl. 1: S37-S45, 1984.
Poulin, R. and F. Labrie, Cancer Res., 1986. 46: p. 4933-4937.
Poulin, R., D. Baker, and F. Labrie, Breast Cancer Res. Treat., 1988. 12: p. 213-225.
Preston Martin et al., Cancer. Res. 50: 7415-21, 1990)
Pye, J. K., R. E. Mansel, and L. E. Hughes, Lancet, 1985. 2: p. 373-377.
Raisz, L. G., Wiita, B., Artis, A., Bowen, A., Schwartz, S., Trahiotis, M., Shoukri,
K., and Smith, J., J Clin Endocrinol Metab, 1996. 81: p. 37-43.
Rasmussen, K. R., M. J. Arrowood, and M. C. Healey. Antimicrob. Agents Chemother., 1992. 36: p. 220-222.
Rocca et al., Lancet Oncol., 2006, 7, 821-828.
Rocca et al., Neurology, 2007, 69, 1074-1083.
Savvas, M., et al., Br. Med. J., 1988. 297: p. 331-333.
Schriock, E. D., et al., J. Clin. Endocrinol. Metab., 1988. 66: p. 1329-1331.
Schwartz, A. G., L. Pashko, and J. M. Whitcomb, Toxicol. Pathol., 1986. 14: p. 357-362.
Sherwin, B. B. and M. M. Gelfand, Am. J. Obstet. Gynecol., 1984. 148: p. 552-557.
Sherwin, B. B. and M. M. Gelfand, Am. J. Obstet. Gynecol., 1985. 151: p. 153-160.
Sherwin, B. B. and M. M. Gelfand, Psychosom Med., 1987. 49: p. 397-409.
Sherwin, B. B., J. Affect. Disord., 1988. 14: p. 177-187.
Shifren, J. L., et al., N Engl J Med, 2000. 343(10): p. 682-8.
Shimokata, H., et al., J Gerontol, 1989. 44(2): p. M66-73.
Sibonga et al., Breast Cancer Res. Treatm. 41: 71-79, 1996.
Simard, J., et al., Int. J. Cancer, 1997. 73: p. 104-112.
Sourla, A., et al., J. Steroid Biochem. Mol. Biol., 1998. 66(3): p. 137-149.
Stomati, M., et al., Gynecol. Endocrinol., 2000. 14(5): p. 342-363.
Studd, J. W., et al., Br. J. Obstet. Gynecol., 1987. 84: p. 314-315.
Suzuki, T., et al., Clin. Immunol. Immunopathol., 1991. 61: p. 202-211.
Tchernof, A., et al., Metabolism, 1995. 44: p. 513-519.
Tchernof, A., Labrie, F., Bélanger, A., and Després, J. P., J. Endocrinol., 1996. 150: p. S155-S164
Vakamatsou et al., Calcified Tissue International 37: 594-597, 1985.
Vermeulen, A. and L. Verdonck, J. Steroid Biochem., 1976. 7: p. 1-10.
Vermeulen, A., et al., J. Clin. Endocrinol. Metab., 1982. 54: p. 187-191.
Villareal, D. T. and J. O. Holloszy, Jama, 2004. 292(18): p. 2243-8.
Wakeling, Breast Cancer Res. Treat. 25: 1-9, 1993
Weinstein and Hutson, Bone 8: 137-142, 1987.
Willson at al., Endocrinology, 138(9), 3901-3911, 1997
Women's Health Initiative, JAMA 288 (2002) 321-333.
Xu et al, 1998, Huang et al., 2004
Xu et al., Nat. Med., 1998, 4, 447-451.
Yen, T. T., et al., Lipids, 1977. 12: p. 409-413.
Yaffe et al., JAMA, 1998, 279, 688-695.
Zumoff, B., et al., Cancer Res., 1981. 41: p. 3360-3363.

It is known that a large number of diseases, conditions and undesirable symptoms respond favorably to administering exogenous sex steroids, or precursors thereof. For example, estrogens are believed to decrease the rate of bone loss while androgens have been shown to build bone mass by stimulating bone formation. Hormone replacement therapy (e.g., administration of estrogens) may be used for the treatment of menopausal symptoms. Progestins are frequently used to counteract the endometrial proliferation and the risk of endometrial cancer induced by estrogens. Use of estrogens, androgenic compounds and/or progestins for treatment, or for prophylactic purposes, for a wide variety of symptoms and disorders suffer from a number of weaknesses. Treatment of females with androgenic compounds may have the undesirable side effect of causing certain masculinising side effects. Also, administering sex steroids to patients may increase the patient's risk of acquiring certain diseases. Female breast cancer, for example, is exacerbated by estrogenic activity.

In addition, androgenic compounds have been found to be beneficial for the treatment of the mastalgia frequently caused by HRT (Pye et al., 1985). In fact, estrogen replacement therapy may result in severe breast pain which may lead to discontinuation of therapy.

More effective hormonal therapies and reduction of side effects and risk are needed. The combination therapies of the present invention, and the pharmaceutical compositions and kits that may be used in those therapies, are believed to address these needs.

SUMMARY OF THE INVENTION

It is an object of the present invention to provide a method of treating or reducing the incidence or risk of acquiring. hot flushes, vasomotor symptoms, night sweats, and sleep disturbance.

It is another object to provide methods of treating or reducing the risk of acquiring the above-indicated diseases, while minimizing the risk of acquiring breast cancer and/or endometrial cancer, osteoporosis, cardiovascular diseases, hypercholesterolemia, hyperlipidemia, atherosclerosis, hypertension, insulin resistance, diabetes, obesity (especially abdominal obesity), and vaginal dryness.

It is another object to provide kits and pharmaceutical compositions suitable for use in the above methods. Preferably, these products are packaged with directions for using the contents thereof for reducing or eliminating the incidence of symptoms selected from the group consisting of hot flushes, vasomotor symptoms, and night sweats.

In one embodiment, the invention provides a method of reducing or eliminating the incidence of hot flushes, vasomotor symptoms, night sweats, and sleep disturbance, said method comprising administering to patient in need of said elimination or reduction, a therapeutically effective amount of a precursor of sex steroids or prodrug thereof in association with administering to said patient a therapeutically effective amount of a selective estrogen receptor modulator or an antiestrogen or prodrug thereof.

It is preferred that the sex steroid precursor is selected from the group consisting of dehydroepiandrosterone, dehydroepiandrosterone-sulfate, androst-5-ene-3β,17β-diol, 4-androstene-3,17-dioneo, and a prodrug of any of the foregoing additional agents.

In another embodiment the invention provides additional beneficial effects or reduces the risk of acquiring a condition selected from the group consisting of osteoporosis, hypercholesterolemia, hyperlipidemia, atherosclerosis, hypertension, Alzheimer's disease, insulin resistance, diabetes, loss of muscle mass, obesity, said beneficial effects being obtained by administering to patient in need of said beneficial effects, a therapeutically effective amount of a precursor of sex steroids or prodrug thereof in association with administering to said patient a therapeutically effective amount of a selective estrogen receptor modulator or prodrug thereof.

In another embodiment the invention provides a pharmaceutical composition comprising:
  a) a pharmaceutically acceptable excipient, diluent or carrier;
  b) a therapeutically effective amount of at least one sex steroid precursor or prodrug thereof; and
  c) a therapeutically effective amount of at least one selective estrogen receptor modulator or an antiestrogen or prodrug.

In another embodiment the invention provides a pill, a tablet, a capsule, a gel, a cream, an ovule, or a suppository comprising:
  a) a pharmaceutically acceptable excipient, diluent or carrier;
  b) a therapeutically effective amount of at least one sex steroid precursor or prodrug thereof; and
  c) a therapeutically effective amount of at least one selective estrogen receptor modulator or an antiestrogen or prodrug.

In another embodiment the invention provides a kit comprising a first container containing a pharmaceutical formulation comprising a therapeutically effective amount of at least one sex steroid precursor or a prodrug thereof; and said kit further comprising a second container containing a pharmaceutical formulation comprising a therapeutically effective amount of at least one selective estrogen receptor modulator or an antiestrogen or prodrug thereof.

In another embodiment, the invention pertains to a method of treating or reducing the incidence of hot flushes, vasomotor symptoms, night sweats, and sleep disturbance by increasing levels of a sex steroid precursor selected from the group consisting of dehydroepiandrosterone (DHEA), dehydroepiandrosterone-sulfate (DHEA-S), androst-5-ene-3β,17β-diol (5-diol) and 4-androstene-3,17-dione in a patient in need of said treatment or said reduction, and further comprising administering to said patient a therapeutically effective amount of a selective estrogen receptor modulator (SERM) as part of a combination therapy.

As used herein, "Pure SERM" means that the SERM does not have any estrogenic activity in breast and endometrial tissues at physiological or pharmacological concentrations.

In another embodiment, the invention provides a kit comprising a first container containing a therapeutically effective amount of at least one precursor of sex steroids and further comprising a second container containing a therapeutically effective amount of at least one selective estrogen receptor modulator.

In another embodiment, the invention provides, in one container, a pharmaceutical composition comprising:
  a) a pharmaceutically acceptable excipient, diluent or carrier;
  b) a therapeutically effective amount of at least one precursor of sex steroids; and
  c) a therapeutically effective amount of at least one selective estrogen receptor modulator.

In another embodiment, the invention provides a method of reducing or eliminating the incidence of symptoms selected from the group consisting of hot flushes, vasomotor symptoms, and night sweats, said method comprising administering to a patient in need of said elimination or reduction, (i) a therapeutically effective amount of a sex steroid precursor or prodrug thereof in association with (ii) a therapeutically effective amount of a selective estrogen receptor modulator or an antiestrogen or prodrug of either.

In another embodiment, the invention provides a pharmaceutical composition for reducing or eliminating symptoms selected from the group consisting of hot flushes, vasomotor symptoms, and night sweats, comprising:
  a) a pharmaceutically acceptable excipient, diluent or carrier;
  b) at least one sex steroid precursor or prodrug thereof; and
  c) at least one selective estrogen receptor modulator or an antiestrogen or prodrug of either;
    wherein said pharmaceutical composition is provided in packaging that directs use of said composition for reduction or elimination of at least one symptom selected from the group consisting of hot flushes, vasomotor symptoms and night sweats.

In another embodiment, the invention provides a kit for reducing or eliminating symptoms selected from the group consisting of hot flushes, vasomotor symptoms, and night sweats, comprising (i) a first container having therein a at least one sex steroid precursor or a prodrug thereof; (ii) a second container having therein a at least one selective estrogen receptor modulator, or an antiestrogen or prodrug of either of the foregoing; and (iii) instructions for using the kit for the reduction or elimination of at least one symptom selected from the group consisting of hot flushes, vasomotor symptoms and night sweats.

As used herein, compounds administered to a patient "in association with" other compounds are administered sufficiently close to administration of said other compound that a patient obtains the physiological effects of both compounds simultaneously, even though the compounds were not administered in close time proximity. When compounds are administered as part of a combination therapy they are administered in association with each other. Preferred selective estrogen receptor modulators discussed herein are preferably used in combination with preferred sex steroid precursors dehydroepiandrosterone, dehydroepiandrosterone-sulfate, androst-5-ene-3β,17β-diol, or 4-androstene-3,17-dione, especially dehydroepiandrosterone.

The estrogen replacement therapy is commonly used in postmenopausal women to prevent and treat diseases due to the menopause, namely osteoporosis, hot flushes, vaginal dryness, coronary heart disease (Cummings 1991) but presents some undesirable effects associated with chronic estrogen administration. Particularly, the perceived increased risk for uterine and/or breast cancer (Judd, Meldrum et al., 1983; Colditz, Hankinson et al., 1995) generated by estrogen is the major disadvantage of this therapy. The authors of the present invention have found that the addition of a selective estrogen receptor modulator (SERM) to precursors of sex steroids administration suppresses these undesirable effects.

On the other hand, SERMs alone have little or no beneficial effects on some menopausal symptoms like hot flushes and sweats. The applicant believes that the addition of a precursor of sex steroids to SERM treatment of menopausal symptoms reduces or even eliminates hot flushes and sweats. It is important to note that hot flushes and sweats are the first manifestations of menopause and the acceptation or non-acceptation of menopausal treatment by patients is usually dependent upon the success or non-success in the reduction of hot flushes and sweats.

As used herein, a selective estrogen receptor modulator (SERM) is a compound that either directly or through its active metabolite functions as an estrogen receptor antagonist ("antiestrogen") in breast tissue, yet provides estrogenic or estrogen-like effect on bone tissue and on serum cholesterol levels (i.e. by reducing serum cholesterol). Non-steroidal compounds that function as estrogen receptor antagonists in vitro or in human or rat breast tissue (especially if the compound acts as an antiestrogen on human breast cancer cells) is likely to function as a SERM. Conversely, steroidal antiestrogens tend not to function as SERMs because they tend not to display any beneficial effect on serum cholesterol. Non-steroidal antiestrogens we have tested and found to function as SERMs include EM-800, EM-652.HCl, Raloxifene, Tamoxifen, 4-hydroxy-Tamoxifen, Toremifene, 4-hydroxy-Toremifene, Droloxifene, LY 353 381, LY 335 563, GW-5638, Lasofoxifene, bazedoxifene (TSE 424; WAY-TSE 424; WAY 140424; 1-[[4-[2-(hexahydro-1H-azepin-1-yl)ethoxy]phenyl]methyl]-2-(4-hydroxyphenyl)-3-methyl-1H-indol-5-ol), Pipendoxifene (ERA 923; 2-(4-hydroxyphenyl)-3-methyl-1-[[4-[2-(1-piperidinyl)ethoxy]phenyl]methyl]-1H-indol-5-ol), and Idoxifene, but are not limited to these compounds.

But we have found also that all SERMs do not react in the same manner and may be divided into two subclasses: "pure SERMs" and "mixed SERMs". Thus, some SERMs like EM-800 and EM-652.HCl do not have any estrogenic activity in breast and endometrial tissues at physiological or pharmacological concentrations and have hypocholesterolemic and hypotriglyceridemic effects in the rat. These SERMS may be called "pure SERMs". The ideal SERM is a pure SERM of the type EM-652.HCl because of its potent and pure antiestrogenic activity in the mammary gland. Others, like Raloxifene, Tamoxifen, Droloxifene, 4-hydroxy-Tamoxifen (1-(4-dimethylaminoethoxyphenyl)-1-(4-hydroxyphenyl)-2-phenyl-but-1-ene), Toremifene, 4-hydroxy-Toremifene [(Z)-(2)-2-[4-(4-chloro-1-(4-hydroxyphenyl)-2-phenyl-1-butenyl)phenoxy]-N,N-dimethylethanamine), LY 353 381, LY 335 563, GW-5638, Lasofoxifene, Idoxifene and Bazedoxifene have some estrogenic activities in the breast and endometrium. This second series of SERMs may be called "mixed SERMs". The unwanted estrogenic activities of these "mixed SERMs" may be inhibited by addition of pure "SERMs" as shown in FIGS. 5 and 6 in vitro tests and in FIG. 7 in an in vivo test of breast cancer. Since human breast carcinoma xenografts in nude mice are the closest available model of human breast cancer, we have thus compared the effect of EM-800 and Tamoxifen alone and in combination on the growth of ZR-75-1 breast cancer xenografts in nude mice.

The applicant believes that it is very important that SERMs of the invention act as pure antiestrogens in breast, uterine, and endometrial tissues because SERMs have to counteract potential side-effects of estrogens, particularly those formed from the exogenous precursors of sex steroids which can increase the risk of cancer in these tissues. Particularly, the applicant believes that benzopyran derivatives of the invention having the absolute configuration 2S at position 2 is more suitable than its racemic mixture. Thus, in U.S. Pat. No. 6,060,503, optically active benzopyran antiestrogens having 2S configuration are disclosed to treat estrogen-exacerbated breast and endometrial cancer and these compounds are shown to be significantly more efficient than racemic mixtures (See FIGS. 1-5 of U.S. Pat. No. 060,503).

The enantiomer of 2S configuration being difficult to be industrially obtained as a pure state, the applicant believes that less than 10%, preferably less than 5% and more preferably less than 2% by weight of contamination by the 2R enantiomer is preferred.

BRIEF DESCRIPTION OF THE DRAWINGS

FIG. 4 shows the effect of increasing oral doses of the antiestrogen EM-800 (15 μg, 50 μg or 100 μg) (B) or of percutaneous administration of increasing doses of DHEA (0.3, 1.0 or 3.0 mg) combined with EM-800 (15 μg) or EM-800 alone (A) for 9.5 months on average ZR-75-1 tumor size in ovariectomized (OVX) nude mice supplemented with estrone. The initial tumor size was taken as 100%. Control OVX mice receiving the vehicle alone were used as additional controls. Estrone was administered subcutaneously at the dose of 0.5 μg once daily while DHEA was dissolved in 50% ethanol-50% propylene glycol and applied on the dorsal skin area twice daily in a volume of 0.02 ml. Comparison is also made with OVX animals receiving the vehicle alone.

FIG. 10 shows sections of rat endometrium:
a) Untreated animal. The luminal epithelium (LE) is characterized by columnar epithelial cells while the glandular epithelium (GE) is rather cuboidal. The stroma contains several cellular elements and collagen fibers.
b) Animal treated with EM-800 (0.5 mg/kg, b w per day) during 12 weeks. The luminal epithelium is markedly reduced in height. The glandular epithelial cells have unstained cytophasm with no sign of activity. The stroma is highly cellular due to reduction in intercellular elements of the stroma.

DETAILED DESCRIPTION OF THE INVENTION

Beneficial Effects of DHEA

Figure 1:
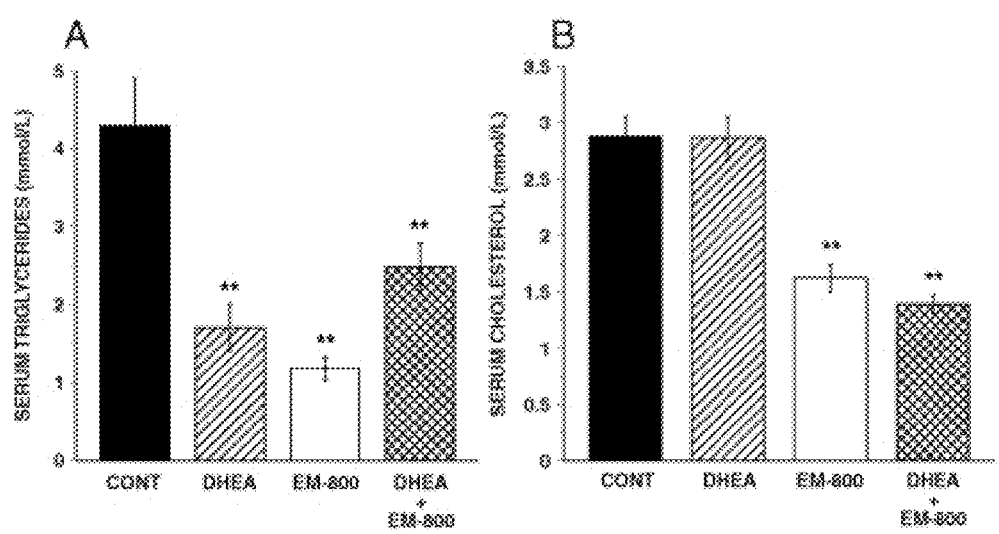
FIG. 1 shows the effect of treatment with DHEA (10 mg, percutaneously, once daily) or EM-800 (75 µg, orally, once daily) alone or in combination for 9 months on serum triglyceride (A) and cholesterol (B) levels in the rat. Data are expressed as the means±SEM. **: $P<0.01$ experimental versus respective control.
Figure 2:
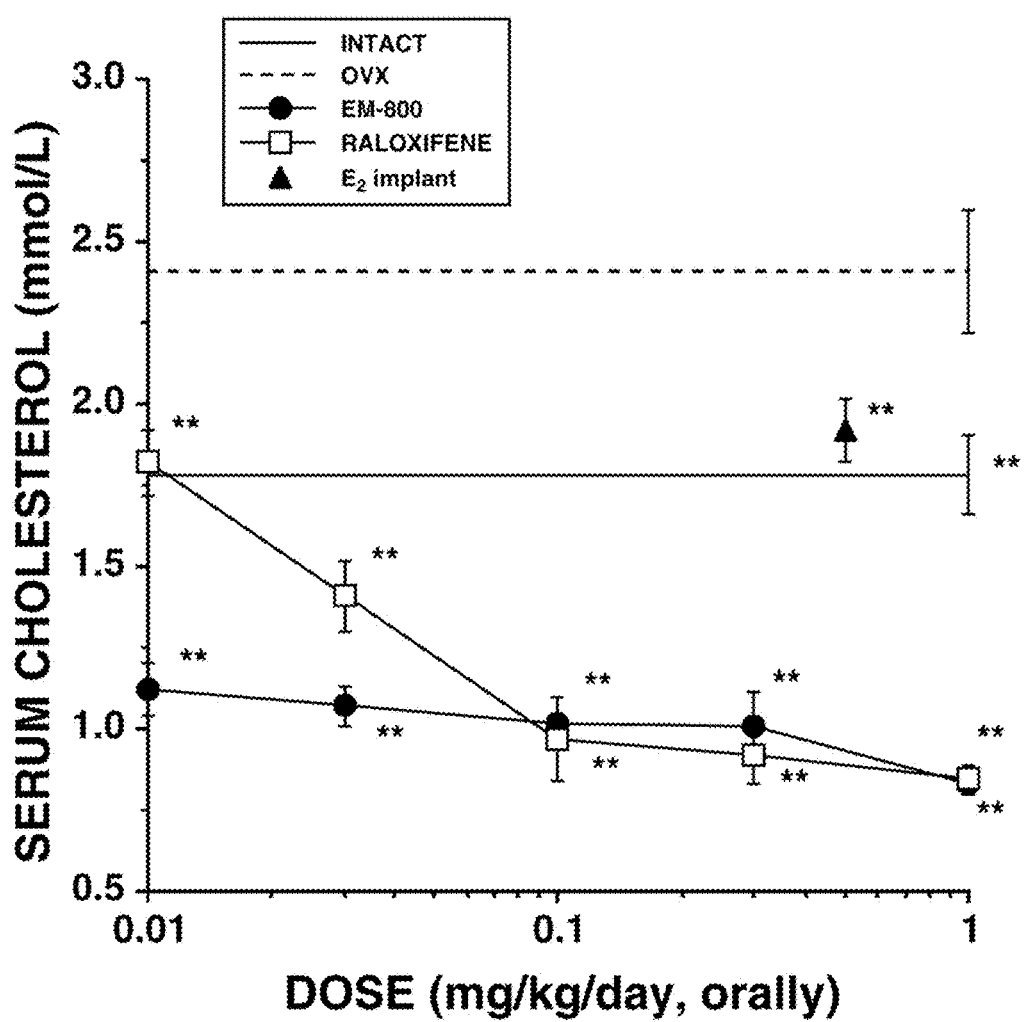
FIG. 2 shows the effect of 37-week treatment with increasing doses (0.01, 0.03, 0.1, 0.3, and 1 mg/kg) of EM-800 or Raloxifene administered on total serum cholesterol levels in the ovariectomized rat. Comparison is made with intact rats and ovariectomized animals bearing an implant of 17β-estradiol ($E_2$);** $p<0.01$, experimental versus OVX control rats.

The most widely recognized fact concerning menopause is that there is a progressive decrease and finally an arrest of estrogen secretion by the ovaries. The cessation of ovarian estrogen secretion is illustrated by the marked decline in circulating 17β-estradiol ($E_2$) levels. This easily measurable change in circulating $E_2$ levels coupled with the beneficial effects of estrogens on menopausal symptoms and bone resorption has concentrated most of the efforts of hormone replacement therapy on various forms of estrogens as well as to combinations of estrogen and progestin in order to avoid the potentially harmful stimulatory effects of estrogens used alone on the endometrium which can result in endometrial hyperplasia and cancer.

The rapid fall in circulating 17β-estradiol ($E_2$) at menopause, coupled with the beneficial effects of exogenous estrogens on menopausal symptoms and bone resorption has focused most of the efforts of hormone replacement therapy on various forms of estrogens as well as to combinations of estrogen and progestin in order to avoid the risk of endometrial cancer induced by estrogens administered alone.

Hormone replacement therapy (HRT), estrogen and progestin, is used in postmenopausal women for the acute symptoms arising from estrogen deficiency, particularly hot flushes and night sweats, and for the long term prevention of osteoporosis and possibly cardiovascular disease. While progestins are effective at protecting the uterus from the stimulatory effects of long term estrogen exposure, it carries its own side effects, in particular dysfunctional uterine bleeding (Archer et al., 1999). This is a frequent side effect and a common reason for women to prematurely stop hormone replacement therapy within the first 6-12 months. The classical HRT has recently been seriously questioned or even abandoned by many women following data indicating that the combination of Premarin and Provera (Prempro) causes a 26% increase in the incidence of breast cancer at 5.2 years of follow-up with a potential negative impact on cardiovascular events (Women's Health Initiative, 2002).

We feel that the increased understanding of androgen and estrogen formation and action in peripheral target tissues called intracrinology (Labrie, 1991; Labrie et al., 1992a; Labrie et al., 1992b; Labrie et al., 1994; Labrie et al., 1995; Luu—The et al., 1995a; Labrie et al., 1996; Labrie et al., 1997a; Labrie et al., 1997b; Labrie et al., 1997c; Labrie et al., 1997d) as well as our recent observations indicating the predominant role of androgens over that of estrogens in the prevention of bone loss after ovariectomy in the rat (Martel et al., 1998) and the observation of a similar situation in post-menopausal women (Labrie et al., 1997c) have paved the way for a timely and potentially highly significant progress in the field of sex steroid replacement therapy and aging. Such a possibility is well supported by our observations.

In Berger et al. (2005) it is shown particularly interesting effects of DHEA on the three layers of the vaginal wall of rat vagina, namely a highly mucified epithelium, an increased muscularis thickness and increased collagen fiber compactness in the lamina propria. Thus DHEA exerts both androgenic and estrogenic effects on the vaginal mucosa, providing a more physiological replacement therapy.

The present invention is thus based upon the recent progress achieved in our understanding of sex steroid physiology in men and women (Labrie, 1991; Labrie et al., 1992a; Labrie et al., 1992b; Labrie et al., 1994; Labrie et al., 1995a; Luu—The et al., 1995a; Labrie et al., 1997a; Labrie et al., 1997b; Labrie et al., 1997c; Labrie et al., 1997d) and the recognition that women, at menopause, are not only deprived from estrogens activity due to a declining ovarian activity, but have already been submitted for a few years to a decreasing exposure to androgens. In fact, normal women produce an amount of androgens equivalent to two thirds of the androgens secreted in men (Labrie et al., 1997a).

The pool of androgens in women decreases progressively from the age of 30 years in parallel with the decrease in the serum concentration of DHEA and DHEA-S (Labrie et al., 1997b). Consequently, it appears logical to use both androgenic and estrogenic replacement therapy at peri- and post-menopause, thus maintaining a physiological balance between these two classes of sex steroids in each cell and tissue, a goal which can only be met by the local formation of androgens and estrogens in peripheral tissues from the steroid precursor DHEA.

DHEA, a Predominant Source of Androgens

Role of DHEA in Peripheral Sex Steroid Formation

Humans, with some other primates, are unique among animal species in having adrenals that secrete large amounts of the inactive precursor steroids DHEA and especially DHEA-S, which are converted into potent androgens and/or estrogens in peripheral tissues. Plasma DHEA-S levels in adult and women are 500 times higher than those of testosterone and 10,000 times higher than those of estradiol, thus providing a large supply of substrate for the formation of androgens and/or estrogens. As mentioned above, the local synthesis and action of sex steroids in peripheral target tissues has been called intracrinology (Labrie et al., 1988; Labrie, 1991). Recent and rapid progress in this area has been made possible by the elucidation of the structure of most of the tissue-specific genes that encode the steroidogenic enzymes responsible for the transformation of DHEA-S and DHEA into androgens and/or estrogens locally in peripheral tissues (Labrie et al., 1992a; Labrie et al., 1992c; Labrie et al., 1995; Luu—The et al., 1995b; Labrie et al., 1996; Labrie et al., 1997d).

The major importance of DHEA and DHEA-S in human sex steroid physiology is illustrated by the estimate that approximately 50% of total androgens in adult men derive from these adrenal precursor steroids (Labrie et al., 1985; Belanger et al., 1986; Labrie et al., 1993), while, in women, our best estimate of the intracrine formation of estrogens in peripheral tissues is in the order of 75% before menopause and close to 100% after menopause (Labrie, 1991).

The almost exclusive focus on the role of ovarian estrogens has removed the attention from the dramatic 70% fall in circulating DHEA which already occurs between the ages of 20 to 30 and 40 to 50 years (Migeon et al., 1957; Vermeulen and Verdonck, 1976; Vermeulen et al., 1982; Orentreich et al., 1984; Belanger et al., 1994; Labrie et al., 1997b). Since DHEA is transformed to both androgens and estrogens in peripheral tissues, such a fall in serum DHEA and DHEA-S explains why women at menopause, as mentioned above, are not only lacking estrogens but are also deprived from androgens.

As mentioned above, recent data suggest that progestins have a negative impact on breast cancer (Clarke and Sutherland, 1990; Musgrove et al., 1991; Horwitz, 1992), with reports indicating an increased risk of the disease (Colditz et al., 1995). In this context, it is important to indicate that the absence of a stimulatory effect of DHEA on the human endometrium (Labrie et al., 1997c) eliminates the need to administer a progestin to neutralize the potential effect of estrogens on the endometrium.

Concerning the breast, DHEA is known to prevent the development (Luo et al., 1997) and to inhibit the growth (Li et al., 1993) of dimethylbenz(a)anthracene mammary tumors in the rat. DHEA, in addition, inhibits the growth of human breast cancer xenografts in nude mice (See example 1 and Couillard et al., 1998). Thus, contrary to estrogens and progestins which exert stimulatory effects, DHEA is expected to inhibit both the development and the growth of breast cancer in women.

As well demonstrated in our previous studies, supplementation with physiological amounts of exogenous DHEA permits the biosynthesis of androgens and estrogens only in the appropriate target tissues which contain the specific steroidogenic enzymes. The active androgens and estrogens thus synthesized remain in the cells of origin and very little leakage occurs into the circulation. In fact, the most striking effects of DHEA administration are on the circulating levels of the glucuronide derivatives of the metabolites of DHT, namely ADT-G and 3α-diol-G, these metabolites being produced locally in the peripheral intracrine tissues which possess the appropriate steroidogenic enzymes to synthesize DHT from the adrenal precursors DHEA and DHEA-S and, thereafter, to further metabolize DHT into inactive conjugates (Labrie, 1991; Labrie et al., 1996). This local biosynthesis and action of androgens in target tissues eliminates the exposure of other tissues to androgens and thus minimizes the risks of undesirable masculinizing or other androgen-related side effects. The same applies to estrogens although we feel that a reliable parameter of total estrogen secretion (comparable to the glucuronides for androgens) is not yet available.

Role of Androgens and Estrogens in Bone Physiology

A predominant role of androgens on bone physiology is well documented (Labrie et al., 1997c; Martel et al., 1998). In fact, both testosterone and DHT increased the transcription of α (I) procollagen mRNA in osteoblast-like osteosarcoma cells (Benz et al., 1991). Treatment with DHT has also been shown to stimulate endochondral bone development in the orchiectomized rat (Kapur and Reddi, 1989). Moreover, bone mineral density measured in the lumbar spine, femoral trochanter and total body was increased more by estrogen+testosterone implants than by $E_2$ alone over a 24-month treatment period in postmenopausal women (Davis et al., 1995).

Moreover, in established osteoporosis, anabolic steroids have been reported to help prevent bone loss (Hennernan and Wallach, 1957). Similarly, subcutaneous $E_2$ and testosterone implants have been found to be more efficient than oral estrogen in preventing osteoporosis in postmenopausal women (Savvas et al., 1988). Although the difference observed in that study has been attributed to the different routes of administration of the estrogen, the cause of the difference could well be the action of testosterone. As index of increased bone formation, an increase in serum osteocalcin, a marker of bone formation has been found in post-menopausal women receiving methyltestosterone plus estrogen, compared with estrogen alone (Raisz et al., 1996). A similar stimulatory effect on serum osteocalcin has been observed following treatment of postmenopausal women with percutaneous DHEA for 12 months (Labrie et al., 1997c). Moreover, androgen therapy, as observed with nandrolone decanoate, has been found to increase vertebral bone mineral density in postmenopausal women (Need et al., 1989). Although androgens are gaining increasing support due to their unique actions in postmenopausal women, virilizing effects are observed with the use of testosterone (Burger et al., 1984; Studd et al., 1987).

DHEA and Abdominal Obesity

Abdominal obesity is associated with an increased risk of insulin resistance, type 2 diabetes and atherosclerosis (Shimokata et al., 1989; Cefalu et al., 1995; Ferrannini et al., 1997; Kopelman, 2000). Among other factors, hormonal changes, especially the declining secretion of DHEA and DHEA-S by the adrenals is thought to be a factor involved (Tchernof et al., 1996). In rat and mouse models, DHEA administration reduces visceral fat accumulation in diet-induced (Yen et al., 1977; Cleary and Zisk, 1986; Mohan et al., 1990; Hansen et al., 1997) obesity. A beneficial effect of DHEA has also been observed on the decrease in insulin resistance that occurs with age (Han et al., 1998).

In a study performed in postmenopausal women who received a DHEA cream for 12 months, we have found that insulin resistance was decreased while subcutaneous fat at the level of the thigh was also decreased (Diamond et al., 1996). Moreover, the daily administration of 50 mg DHEA for 6 months in 65 to 78-year old men and women decreased abdominal visceral fat by 10.2% in women and 7.4% in men (Villareal and Holloszy, 2004). In the same study, abdominal subcutaneous fat was decreased by 6% in both women and men. Moreover, the responsiveness of serum insulin to the glucose tolerance test was decreased by 13% with no change in the glucose response, thus leading to a 34% improvement in the insulin sensitivity index following DHEA administration. An improvement in DHEA action has also been found in middle-aged men suffering from hypercholesterolemia (Kawano et al., 2003).

In a previous study performed by the same group, DHEA administration for 6 months decreased total body fat mass by 1.4 kg while fat-free mass was increased by 0.9 kg (Villareal et al., 2000). Effects of androgens on libido, hot flushes and quality of life.

Community-based studies suggest self-reported sexual dysfunctions in women which range from 8% to 50%. In fact, low libido and sexual dysfunction increases with age in women from the third decade (Laumann et al., 1999) as well as after ovariectomy (Nathorst-Boos and von Schoultz, 1992). While phychosocial and health factors are involved in low arousal and sexual desire (Dennerstein et al., 1997) it is believed that low androgens play an independent role (Bachmann et al., 2002; Miller et al., 2004).

Androgens are known to play a role in women's arousability, pleasure as well as intensity and ease of orgasm. Androgens are also involved in the neurovascular smooth muscle response of swelling and increased lubrication (Basson, 2004). Estrogens affect the vulval and vaginal congestive responses. Since estrogens also affect mood, they have an influence on sexual interest (Basson, 2004). It should be remembered that DHEA is transformed into both androgens and estrogens in the vagina (Sourla et al., 1998) (Berger et al., 2005)

In addition, the detailed benefits of androgens added to ERT or HRT have been described on general well-being, energy, mood, and general quality of life (Sherwin and Gelfand, 1985; Sherwin, 1988). Improvements in the major psychologic and psychomatic symptoms, namely irritability, nervousness, memory, and insomnia have been observed following addition of androgens to estrogen replacement therapy (ERT) (Notelovitz et al., 1991).

Loss of libido and/or sexual satisfaction are common in early post-menopause. The addition of androgens to hormone replacement therapy (HRT) is known to have beneficial effects on these problems. Shifren et al., (2000) have found that transdermal testosterone administered by patch improved sexual frequency, pleasure and mood in surgically menopausal women. The effect was seen at a daily 300 µg dose of testosterone, a dose that led to serum testosterone levels in the upper limit of normal. Testosterone treatment has also been studied in non androgen-deficient women complaining of decreased libido (Goldstat et al., 2003). Such treatment with testosterone improved libido, sexual function as well as quality of life compared to placebo. Similarly, in menopausal women with normal levels of androgens, the addition of methyltestosterone to estrogen increased sexual desire and frequency as compared to estrogen alone (Lobo et al., 2003). Among women with dysfunction of sexual interest, desire, androgen therapy has been suggested for those having free serum testosterone levels within the lower quantile of the reference range (Bachmann et al., 2002). In fact, there is increased use of testosterone to treat hypoactive sexual desire disorder (HSDD) (Sherwin and Gelfand, 1987; Davis et al., 1995; Shifren et al., 2000; Goldstat et al., 2003). These randomized clinical trials demonstrate that testosterone is effective in women with HSDD.

The androgenic effect of DHEA should also be useful in reducing hot flushes. In fact, androgen therapy is successful in reducing hot flushes in hypogonadal men (De Fazio et al., 1984) and in menopausal transition in women (Overlie et al., 2002). Moreover, the addition of androgens has been found to be effective in relieving hot flushes in women who had unsatisfactory results with estrogen alone (Sherwin and Gelfand, 1984). Hot flushes are one of the main reasons women initially seek HRT therapy, and estrogen is very effective at alleviating this symptom.

A clear example of nature of androgen deficiency of adrenal origin is provided by cases of adrenal insufficiency. (Arlt et al., 1999) have studied the effect of DHEA, 50 mg daily and placebo for 4 months in a population of women suffering from adrenal insufficiency. Treatment with DHEA raised serum testosterone in the low normal range. Such treatment increased the frequency of sexual thoughts, interest and satisfaction. Well-being, depression and anxiety were also improved. In a study where DHEA was administered at a high 300 mg daily dose, a greater subjective mental (p<0.016) and physical (p<0.030) was observed in response to an erotic video (Hackbert and Heiman, 2002). In a study performed in women receiving 50 mg DHEA daily, improved libido was observed in women aged 70 years or more but not in those aged 60 to 70 years (Baulieu, 1999). DHEA has also shown beneficial effects on hot flushes (Baulieu, 1999; Stomati et al., 2000). In a recent Canadian survey, 70.8% of practitioners add androgen to estrogen to enhance quality of life (Gelfand, 2004).

Other Potential Benefits of DHEA

The 70 to 95% reduction in the formation of DHEA and DHEA-S by the adrenals during aging results in a dramatic reduction in the formation of androgens and estrogens in peripheral target tissues, which could well be involved in the pathogenesis of age-related diseases such as insulin resistance (Coleman et al., 1982; Schriock et al., 1988) and obesity (Nestler et al., 1988; MacEwen and Kurzman, 1991; Tchernof et al., 1995). Low circulating levels of DHEA-S and DHEA have, in fact, been found in patients with breast cancer (Zumoff et al., 1981) and DHEA has been found to exert antioncogenic activity in a series of animal models (Schwartz et al., 1986; Gordon et al., 1987; Li et al., 1993). DHEA has also been shown to have immuno modulatory effects in vitro (Suzuki et al., 1991) and in vivo in fungal and viral diseases (Rasmussen et al., 1992), including HIV (Henderson et al., 1992). On the other hand, a stimulatory effect of DHEA on the immune system has been described in postmenopausal women (Casson et al., 1993).

Previous Data Obtained with DHEA in Women

The use of estrogen replacement therapy requires the addition of progestins to counteract the endometrial proliferation induced by estrogens while both estrogens and progestins could increase the risk of breast cancer (Bardon et al., 1985; Colditz et al., 1995). In order to avoid the limitations of standard estrogen (ERT) or hormonal replacement therapy (HRT), we have studied the effect of DHEA administration to 60 to 70 year old women for 12 months on bone mineral density, parameters of bone formation and turnover, serum lipids, glucose and insulin, adipose tissue mass, muscular mass, energy, well-being as well as on vaginal and endometrial histology (Diamond et al., 1996; Labrie et al., 1997c). DHEA was administered percutaneously to avoid first passage of the steroid precursor through the liver.

We have thus evaluated the effect of chronic replacement therapy with a 10% DHEA cream applied once daily for 12 months in 60 to 70 year old women (N=15). Anthropometric measurements showed no change in body weight but a 9.8% decrease in subcutaneous skin fold thickness at 12 months (p<0.05) (Diamond et al., 1996). Bone mass density was increased by 2.3% at the hip, 3.75% at the hip Ward's triangle, and 2.2% at the lumbar spine level (all p<0.05). These changes in bone mineral density were accompanied by significant decreases at 12 months of 38% and 22% in urinary hydroxyproline and in plasma bone alkaline phosphatase, respectively (all p<0.05). An increase of 135% over control (p<0.05) in plasma osteocalcin was concomitantly observed, thus suggesting a stimulatory effect of DHEA on bone formation.

Measurements of mid-thigh fat and muscle areas by computed tomography have shown a 3.8% decrease (p<0.05) of femoral fat and a 3.5% increase (p<0.05) in femoral muscular area at 12 months (Diamond et al., 1996). There was no significant change in abdominal fat measurements. These changes in body fat and muscular surface areas were associated with a 12% decrease (p<0.05) of fasting plasma glucose and a 17% decrease (p<0.05) in fasting plasma insulin levels. Treatment with DHEA had no undesirable effect on the lipid or lipoprotein profile. In fact, there was an overall trend for a 3% to 10% decrease in total cholesterol and its lipoprotein fractions. Plasma triglycerides were not affected.

The index of sebum secretion was 79% increased after 12 months of DHEA therapy with a return to pretreatment values 3 months after cessation of treatment. DHEA administration stimulated vaginal epithelium maturation in 8 out of 10 women who had a maturation value of zero at the onset of therapy while a stimulation was also seen in the three women who had an intermediate vaginal maturation before therapy. Most importantly, the estrogenic stimulatory effect observed in the vagina was not found in the endometrium which remained completely atrophic in all women after 12 months of DHEA treatment (Labrie et al., 1997c).

The present data clearly indicate the beneficial effects of DHEA therapy in postmenopausal women through its transformation into androgens and/or estrogens in specific intracrine target tissues without significant side effects. The absence of stimulation of the endometrium by DHEA eliminates the need for progestin replacement therapy, thus avoiding the fear of progestin-induced breast cancer. The observed stimulatory effect of DHEA on bone mineral density and the increase in serum osteocalcin, a marker of bone formation, are of particular interest for the prevention and treatment of osteoporosis and indicate a unique activity of DHEA on bone physiology, namely on bone formation while, ERT and HRT can only reduce the rate of bone loss.

A role of androgens has been proposed on depression, memory loss, loss of cognition and brain cell activity (Almeida et al., 2008, Azad et al., 2003 and Hajszan et al., 2008). Estrogens which can also be synthesized in brain from DHEA have been shown to have a beneficial role in Alzheimer's disease, memory loss and loss of cognition (Rocca et al., 2007). Three metaanalyses have shown a 20 to 40% decreased risk of Alzheimer's disease in women who used estrogen after menopause (Yaffe et al., 1998, Leblanc et al., 2001, Hogovorst et al., 2000). Estrogen reduces beta-amyloid deposition in the brain whereas progesterone has the opposite effect (Xu et al, 1998, Huang et al., 2004).

An association between lack of estrogen and cognitive impairment or dementia is supported by laboratory data. Among them estrogen improves synapse formation on dendritic spines in the hippocampi of oophorectomized rats (Mc Ewen and Alves, 1999, Monk and Brodatz, 2000). Moreover, estrogen improves cerebral blood flow and glucose metabolism and it may act as an antioxidant ((Mc Ewen and Alves, 1999; Monk and Brodatz, 2000; Gibbs and Aggamal, 1998). Estrogen has also been found to prevent B-Amyloid 1-42 from inducing a rise in intracellular calcium and from causing mitochondrial damage (Chen et al., 2006, Morrison et al., 2006).

There is now solid evidence from clinical studies that there is a critical age window for the beneficial effects of estrogens on neuroprotection (Rocca et al., 2007), cardiovascular disease (Manson et al., 2006) and overall mortality (Rocca et al., 2006). The best benefits are seen when the treatment with $E_2$ has been started early with sometimes no or negative effects when the treatment is started late after menopause (WHI study). Estrogen reduces beta-amyloid deposition in the brain whereas progesterone has the apposite effect (Xu et al., 1998, Huan et al., 2004).

Benefits of DHEA: Combination of Estrogen-Like and Androgenic Effects

It has been observed that androgens exert a direct antiproliferative activity on the growth of ZR-75-1 Androgens have also been shown to inhibit the growth of DMBA-induced mammary carcinoma in the rat, this inhibition being reversed by the simultaneous administration of the pure antiandrogen Flutamide (Dauvois et al., 1989). Taken together, these data indicate the involvement of the androgen receptor in the inhibitory action of DHEA on breast cancer human breast cancer cells in vitro and that such an inhibitory effect of androgens is additive to that of an antiestrogen (Poulin and Labrie, 1986; Poulin et al., 1988). Similar inhibitory effects have been observed in vivo on ZR-75-1 xenographts in nude mice (Dauvois et al., 1991).

We have shown that DHEA exerts beneficial effects on bone in both the female rat (Luo et al., 1997), and postmenopausal women (Labrie et al., 1997c). Thus, in intact female rats, treatment with DHEA increases bone mineral density (BMD) of total skeleton, lumbar spine and femur (Luo et al., 1997).

Figure 8:
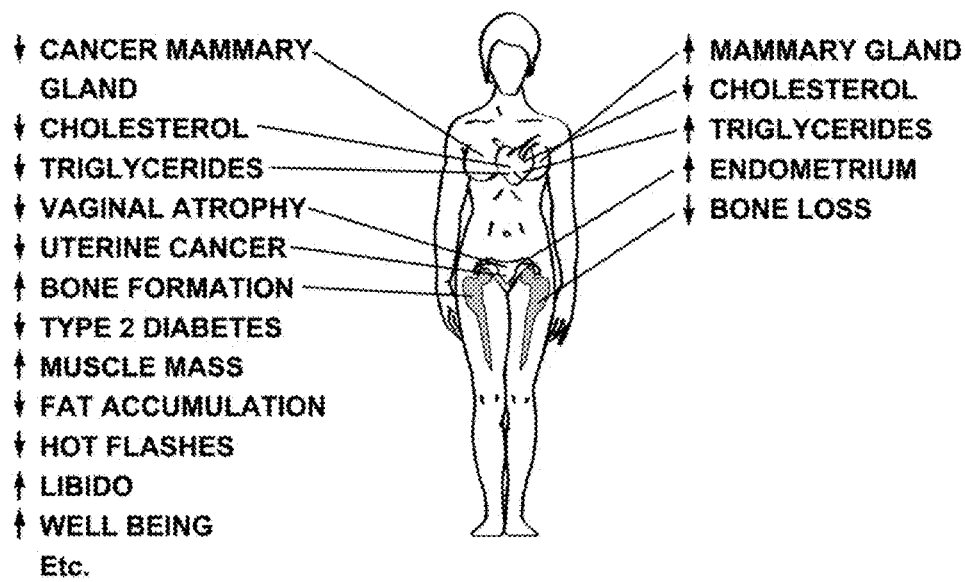
FIG. 8 shows the comparison of the effects of standard ERT (estrogen) or HRT (estrogen+progestin) and the combination of dehydroepiandrosterone and the SERM Acolbifene on parameters of menopause. The addition of Acolbifene to dehydroepiandrosterone will counteract the potentially negative effect of estrogen formed from dehydroepiandrosterone.

The present invention is based upon the recent progress achieved in our understanding of sex steroid physiology in women and the recognition that women, at menopause, are not only deprived from estrogen due to the arrest of estrogen secretion by the ovaries, but have already been submitted for a few years to a decreasing exposure to androgens. In fact, normal women produce an amount of androgens equivalent to two thirds of the androgens secreted in men (Labrie et al., 1997a). The pool of androgens in women decreases progressively from the age of 30 years in parallel with the decrease in the serum concentration of DHEA and DHEA-S (Labrie et al., 1997b). Consequently, it appears logical to use both androgenic and estrogenic replacement therapy at peri- and post-menopause, thus maintaining a physiological balance between these two classes of sex steroids in each cell and tissue, a goal which can only be met by the local formation of androgens and estrogens in peripheral tissues from a steroid precursor such as DHEA. The addition of a SERM like Acolbifene is to increase the positive effect on breast cancer protection as well as on other benefice of SERM administration. In FIG. 8, comparison is made with the positive and negative effects of classical ERT.

Previous data indicate the beneficial effects of DHEA therapy in postmenopausal women through its transformation into androgens and/or estrogens in specific intracrine target tissues without significant side effects. In fact, our data obtained in the rat clearly demonstrate that DHEA can provide the beneficial effects which are lacking with the use of a selective estrogen receptor modulator (SERM) alone.

Figure 7:
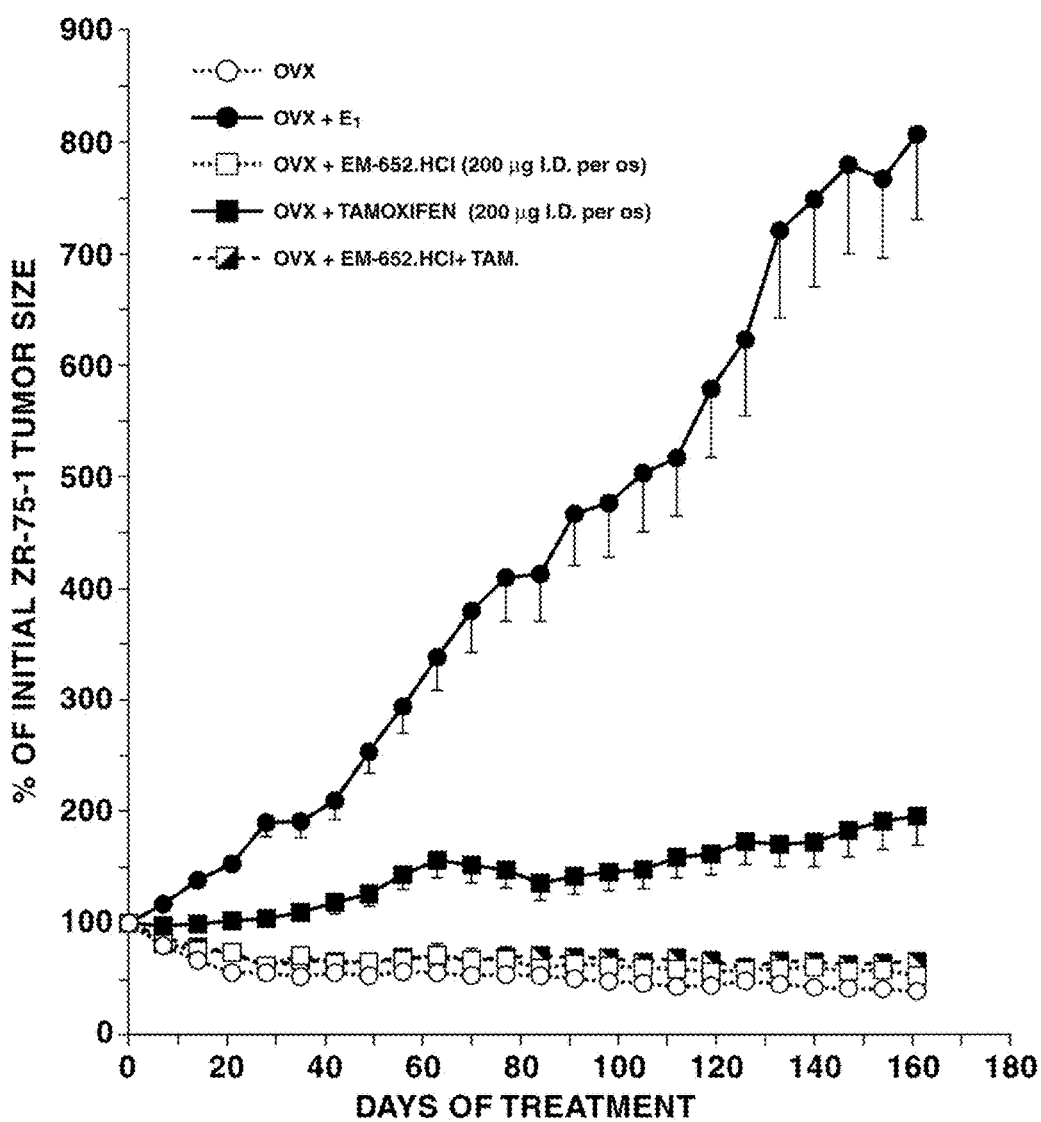
FIG. 7 shows that the stimulatory effect of Tamoxifen on the growth of human breast cancer ZR-75-1 xenografts is completely blocked by simultaneous administration of EM-652.HCl. EM-652.HCl, by itself, in agreement with its pure antiestrogenic activity has no effect on tumor growth in the absence of Tamoxifen.

Beneficial Effects of Acolbifene:

It can be seen in FIG. 7 that the approximately 100% stimulatory effect of Tamoxifen on tumor growth was completely blocked by simultaneous treatment with EM-652HCl. EM-652.HCl in accordance with its pure antiestrogenic activity did not exert any stimulatory effect on the growth of the human breast cancer ZR-75-1 xenografts in nude mice.

We have tested the steroidal antiestrogen fluvestrant (Faslodex, ICI-182,780) and found it not to function as a SERM but antiestrogen fluvestrant may also be used in combination with DHEA in the present invention for the prevention of breast cancer. SERMs, in accordance with the invention, may be administered in the same dosage as known in the art, even where the art uses them as antiestrogens instead of as SERMs.

We have also noted a correlation between the beneficial effect of SERMs have on serum cholesterol and beneficial estrogenic or estrogen-like effects on bone. SERMs have also a beneficial effect on hypertension, insulin resistance, diabetes, and obesity (especially abdominal obesity). Without intending to be bound by theory, it is believed that SERMs, many of which preferably have two aromatic rings linked by one to two carbon atoms, are expected to interact with the estrogen receptor by virtue of the foregoing portion of the molecule that is best recognized by the receptor. Preferred SERMs have side chains which may selectively cause antagonistic properties in breast and usually uterine tissues without having significant antagonistic properties in other tissues. Thus, the SERMs may desirably functions as antiestrogens in the breast while surprisingly and desirably functioning as estrogens (or providing estrogen-like activity) in bone and in the blood (where concentrations of lipid and cholesterol are favorably affected). The favorable effect on cholesterol and lipids translates to a favorable effect against atherosclerosis which is known to be adversely affected by improper levels of cholesterol and lipids.

Figure 9:
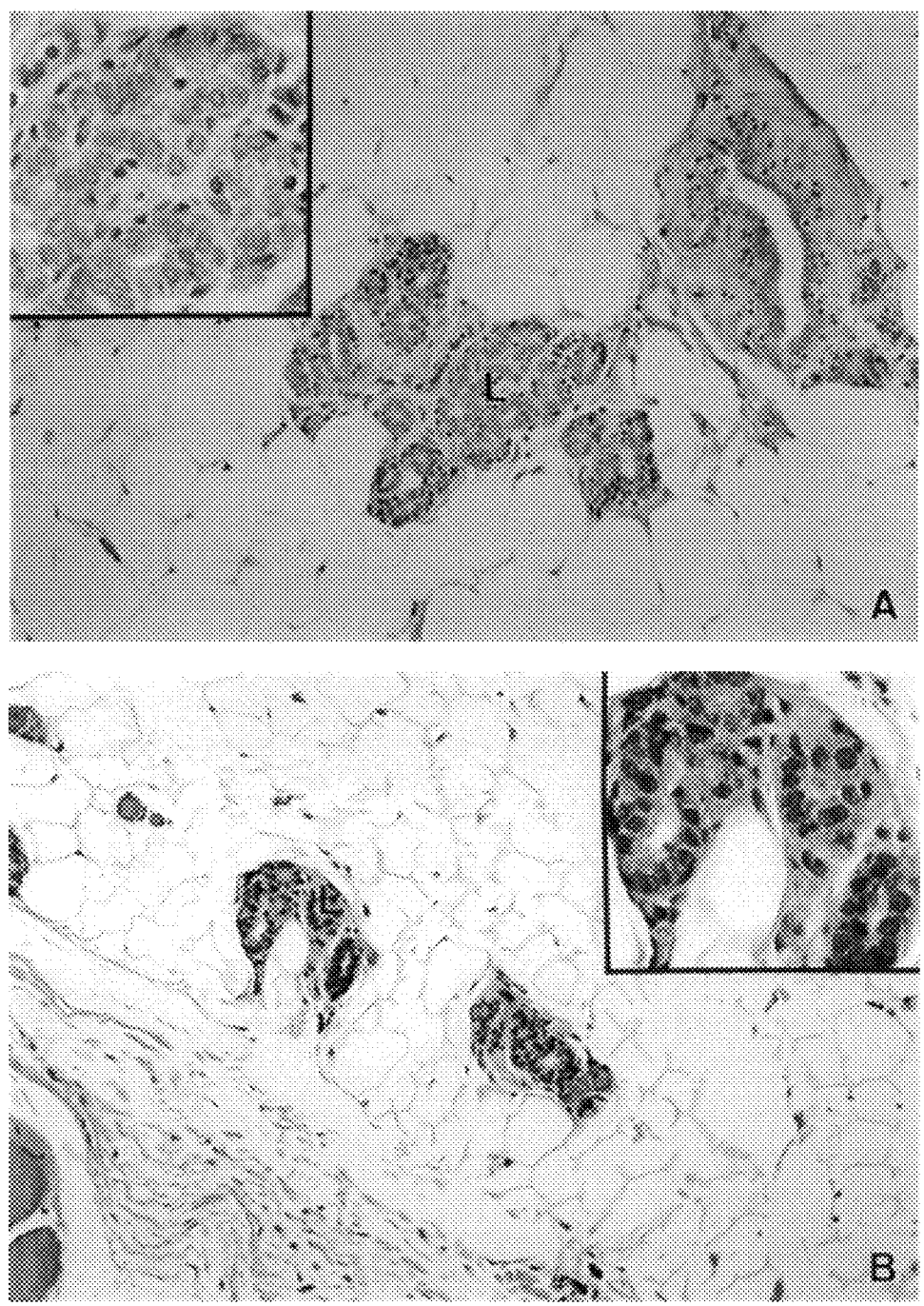
FIG. 9 shows sections of rat mammary gland:
a) Untreated animal. The lobules (L) consist of a few alveoli. Insert. High magnification showing alveoli.
b) Animal treated with EM-800 (0.5 mg/kg, b w per day) for 12 weeks. The lobules (L) are reduced in size. Insert. High magnification showing atrophied alveolar cells.

As demonstrated in FIG. 9, although circulating levels of 17β-estradiol were elevated from 95.9±32.4 pg/ml in intact animals to 143.5±7.8 pg/ml (50% elevation in animals treated with EM-800, 0.5 mg/kg, orally daily/for 12 weeks), a marked atrophy of the mammary gland was observed. Similarly, in FIG. 10, a marked atrophy of the endometrium was observed in animals receiving EM-800 (0.5 mg/kg). In these intact animals receiving the pure antiestrogen EM-800, the inhibitory effect of estrogens at the hypothalamo-pituitary level was removed, thus causing increased LH and then secondarily increased 17β-estradiol secretion by the ovaries.

Hot flushes, cardiovascular symptoms, Alzheimer's disease, loss of cognitive functions and insomnia involve certainly estrogen receptors situated in the nervous central system. Probably, low levels of estrogens in the brain, can explain at least in part, these conditions. Exogenous estrogens and particularly those (i.e. estradiol) formed by the administration of sex steroid precursors can pass through the brain barrier and bind to the estrogen receptor to restore the normal estrogenic action. On the other hand, SERMs of the invention, and more particularly those of Acolbifene family, cannot pass through the brain barrier as shown in example 8. Thus, they cannot antagonise the positive effect of estrogens in brain but they antagonise the negative effects of estrogens in the breast, uterine, and endometrial tissues rending this combination (SERM+sex steroid precursor) particularly attractive for the treatment or reduction of the risk of acquiring the above-mentioned conditions.

As mentioned earlier, a role for androgens has also been suggested for all these symptoms. In fact, DHEA can provide both estrogens and androgens in the brain according to physiological needs.

Overall Additive Benefits of Combining a Sex Steroid Precursor and a SERM or an Antiestrogen The main reason why women consult their physician at menopause is the occurrence of hot flushes, a problem well known to be eliminated by estrogen replacement therapy. Since the site responsible for hot flushes is the central nervous system (CNS) and EM-652 has very poor accessibility to the CNS (data enclosed), it is expected that sex steroid precursor administration will increase estrogen concentration in central nervous system and thus will control hot flushes without interference by the SERM. On the other hand, the SERM will eliminate all the negative effects of estrogens at other sites, specially the risk of breast and uterine cancer. In fact, the addition of EM-652 to sex steroid precursor blocks the stimulatory effect of formed estrogens on the mammary gland and uterus while, in other tissues, EM-652 will exert its own beneficial effect, for example on the bone, where it partially reverses the effect of ovariectomy on bone mineral density.

By removing E2, we decrease the risk of breast cancer since our data show that DHEA can decrease hot flushes, vasomotor symptoms and night sweats. However, DHEA can be slightly transformed into estrogens, thus the need for a SERM.

No adverse effect of EM-652 is seen on any parameter while it should exert marked beneficial effects for the prevention and treatment of breast and uterine cancer.

Preferred SERMs or antiestrogens discussed herein relate: (1) to all diseases stated to be susceptible to the invention; (2) to both therapeutic and prophylactic applications; and (3) to preferred pharmaceutical compositions and kits.

A patient in need of treatment or of reducing the risk of onset of a given disease is one who has either been diagnosed with such disease or one who is susceptible of acquiring such disease.

Except where otherwise stated, the preferred dosage of the active compounds (concentrations and modes of administration) of the invention is identical for both therapeutic and prophylactic purposes. The dosage for each active component discussed herein is the same regardless of the disease being treated (or of the disease whose likelihood of onset is being reduced).

Except when otherwise noted or where apparent from context, dosages herein refer to weight of active compounds unaffected by pharmaceutical excipients, diluents, carriers or other ingredients, although such additional ingredients are desirably included, as shown in the examples herein. Any dosage form (capsule, pill, tablet, injection or the like) commonly used in the pharmaceutical industry is appropriate for use herein, and the terms "excipient", "diluent", or "carrier" include such nonactive ingredients as are typically included, together with active ingredients in such dosage forms in the industry. For example, typical capsules, pills, enteric coatings, solid or liquid diluents or excipients, flavorants, preservatives, or the like may be included.

All of the active ingredients used in any of the therapies discussed herein may be formulated in pharmaceutical compositions which also include one or more of the other active ingredients. Alternatively, they may each be administered separately but sufficiently simultaneous in time so that a patient eventually has elevated blood levels or otherwise enjoys the benefits of each of the active ingredients (or strategies) simultaneously. In some preferred embodiments of the invention, for example, one or more active ingredients are to be formulated in a single pharmaceutical composition. In other embodiments of the invention, a kit is provided which includes at least two separate containers wherein the contents of at least one container differs, in whole or in part, from the contents of at least one other container with respect to active ingredients contained therein.

Combination therapies discussed herein also include use of one active ingredient (of the combination) in the manufacture of a medicament for the treatment (or risk reduction) of the disease in question where the treatment or prevention further includes another active ingredient of the combination in accordance with the invention. For example in one embodiment, the invention provides the use of a SERM in the preparation of a medicament for use, in combination with a sex steroid precursor in vivo, in the treatment of any of the diseases for which the present combination therapy is believed effective (i.e. hot flushes, sweat, irregular menstruation, and any symptoms related to menopause).

Estrogens are well-known to stimulate the proliferation of breast epithelial cells and cell proliferation itself is thought to increase the risk of cancer by accumulating random genetic errors that may result in neoplasia (Preston Martin et al., 1990). Based on this concept, antiestrogens have been introduced to prevent breast cancer with the objective of reducing the rate of cell division stimulated by estrogens.

Figure 3:
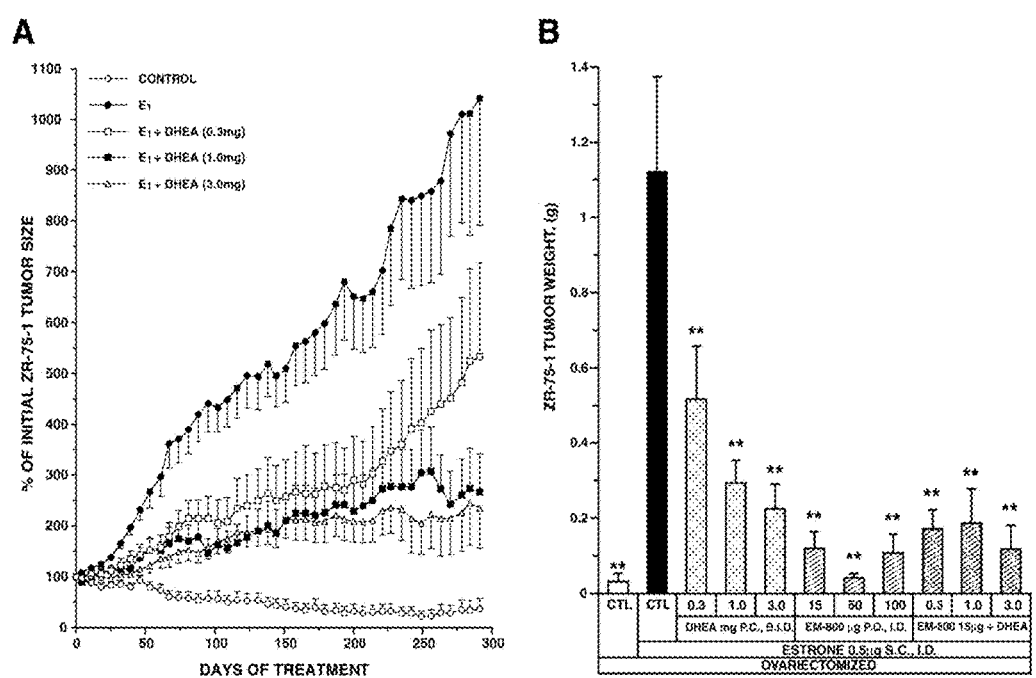
FIG. 3 shows: A) Effect of increasing doses of DHEA (0.3 mg, 1.0 mg or 3.0 mg) administered percutaneously twice daily on average ZR-75-1 tumor size in ovariectomized (OVX) nude mice supplemented with estrone. Control OVX mice receiving the vehicle alone are used as additional controls. The initial tumor size was taken as 100%. DHEA was administered percutaneously (p.c.) in a 0.02 ml solution of 50% ethanol-50% propylene glycol on the dorsal skin. B) Effect of treatment with increasing doses of DHEA or EM-800 (a SERM of the present invention) alone or in combination for 9.5 months on ZR-75-1 tumor weight in OVX nude mice supplemented with estrone. **, p<0.01, treated versus control OVX mice supplemented with estrone.
Figure 5:
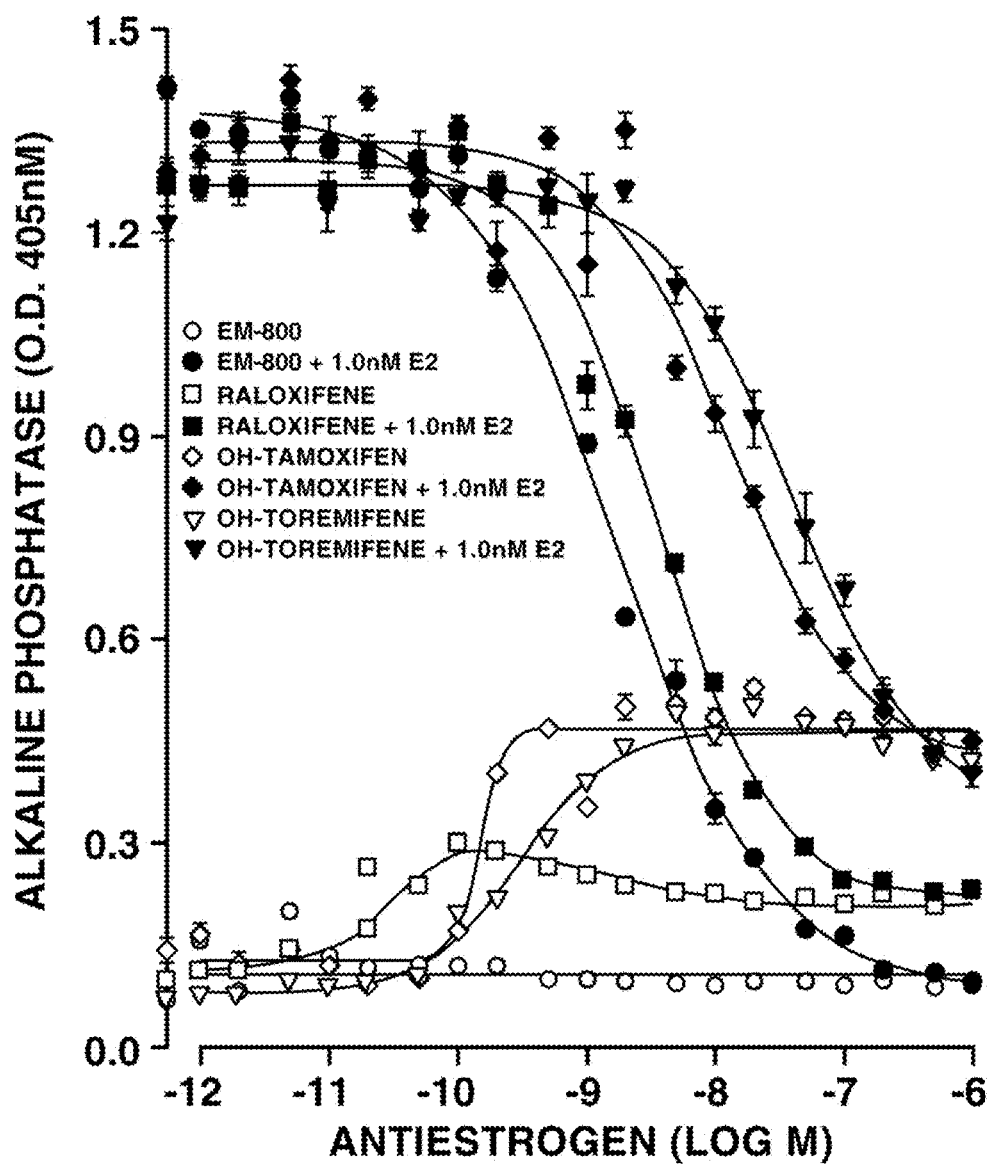
FIG. 5 shows the effect of increasing concentrations of EM-800, (Z)-4-OH-Tamoxifen, (Z)-4-OH-Toremifene and Raloxifene on alkaline phosphatase activity in human Ishikawa cells. Alkaline phosphatase activity was measured after a 5-day exposure to increasing concentrations of indicated compounds in the presence or absence of 1.0 nM $E_2$. The data are expressed as the means±SEM of four wells. When SEM overlaps with the symbol used, only the symbol is shown (Simard, Sanchez et al., 1997).
Figure 6:
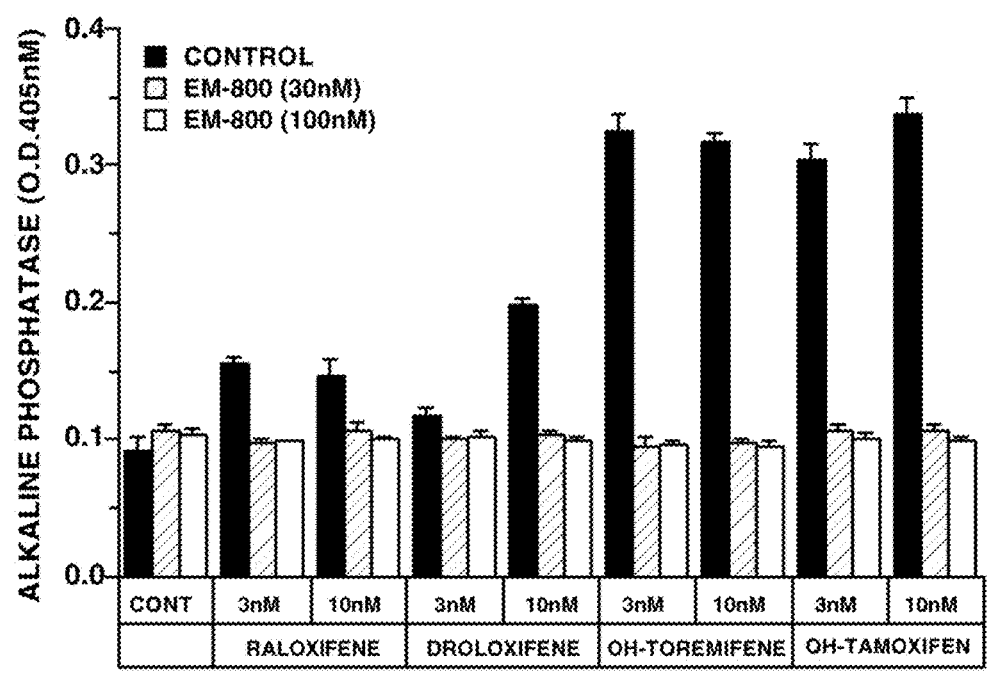
FIG. 6 shows the blockade of the stimulatory effect of (Z)-4-OH-Tamoxifen, (Z)-4-OH-Toremifene, Droloxifene and Raloxifene on alkaline phosphatase activity by the antiestrogen EM-800 in human Ishikawa carcinoma cells. Alkaline phosphatase activity was measured after a 5-day exposure to 3 or 10 nM of the indicated compounds in the presence or absence of 30 or 100 nM EM-800. The data are expressed as the means±SD of eight wells with the exception of the control groups were data are obtained from 16 wells (Simard, Sanchez et al., 1997).

We have also studied the potential interaction of the inhibitory effect of the novel antiestrogen (EM-800) with that of sex steroid precursor (DHEA) on the growth of human ZR-75-1 breast cancer xenografts in nude mice by combined administration of the two drugs. FIGS. 3 and 4 show that DHEA, by itself, at the doses used, causes a 50 to 80% inhibition of tumor growth while the near complete inhibition of tumor growth achieved with a low dose of the antiestrogen was not affected by DHEA.

The limitations of bone mineral density (BMD) measurements are well known. As an example, BMD measurements showed no change in rats treated with the steroidal antiestrogen ICI-182780 (Wakeling, 1993) while inhibitory changes were seen by histomorphometry (Gallagher et al., 1993). Similar differences were reported with Tamoxifen (Jordan et al., 1987; Sibonga et al., 1996).

It should be indicated that reduced bone mineral density is not the only abnormality associated with reduced bone strength. It is thus important to analyze the changes in biochemical parameters of bone metabolism induced by various compounds and treatments in order to gain a better knowledge of their action.

It is particularly important to indicate that the combination of DHEA and EM-800 exerted unexpected beneficial effects on important biochemical parameters of bone metabolism. In fact, DHEA alone did not affect the urinary hydroxyproline/creatinine ratio, a marker of bone resorption. Moreover, no effect of DHEA could be detected on daily urinary calcium or phosphorus excretion (Luo et al., 1997). EM-800 decreased the urinary hydroxyproline/creatinine ratio by 48% while, similarly to DHEA, no effect of EM-800 was seen on urinary calcium or phosphorus excretion. EM-800, moreover, had no effect on serum alkaline phosphatase activity, a marker of bone formation while DHEA increased the value of the parameter by about 75% (Luo et al., 1997).

One of the unexpected effects of the combination of DHEA and EM-800 relates to the urinary hydroxyproline/creatinine ratio, a marker of bone resorption, which was reduced by 69% when both DHEA and EM-800 were combined, this value being statistically different ($p<0.01$) from the 48% inhibition achieved by EM-800 alone while DHEA alone did not show any effect. Thus, the addition of DHEA to EM-800 increases by 50% the inhibitory effect of EM-800 on bone reabsorption. Most importantly, another unexpected effect of the addition of DHEA to EM-800 was the approximately 84% decrease in urinary calcium (from 23.17±1.55 to 3.71±0.75 µmol/24 h/100 g ($p<0.01$) and the 55% decrease in urinary phosphorus (from 132.72±6.08 to 59.06±4.76 µmol/24 h/100 g ($p<0.01$) respectively, (Luo et al., 1997).

Importantly, the combination of EM-800 and DHEA in ovariectomized rats treated for 12 months had beneficial effects on bone morphometry. Trabecular bone volume is particularly important for bone strength and to prevent bone fractures. Thus, in the above-mentioned study, trabecular bone volume of the tibia increased from 4.1±0.7% in ovariectomized rats to 11.9±0.6% ($p<0.01$) with DHEA alone while the addition of EM-800 to DHEA further increased trabecular bone volume to 14.7±1.4%, a value similar to that found in intact controls (FIG. 15).

Figure 16:
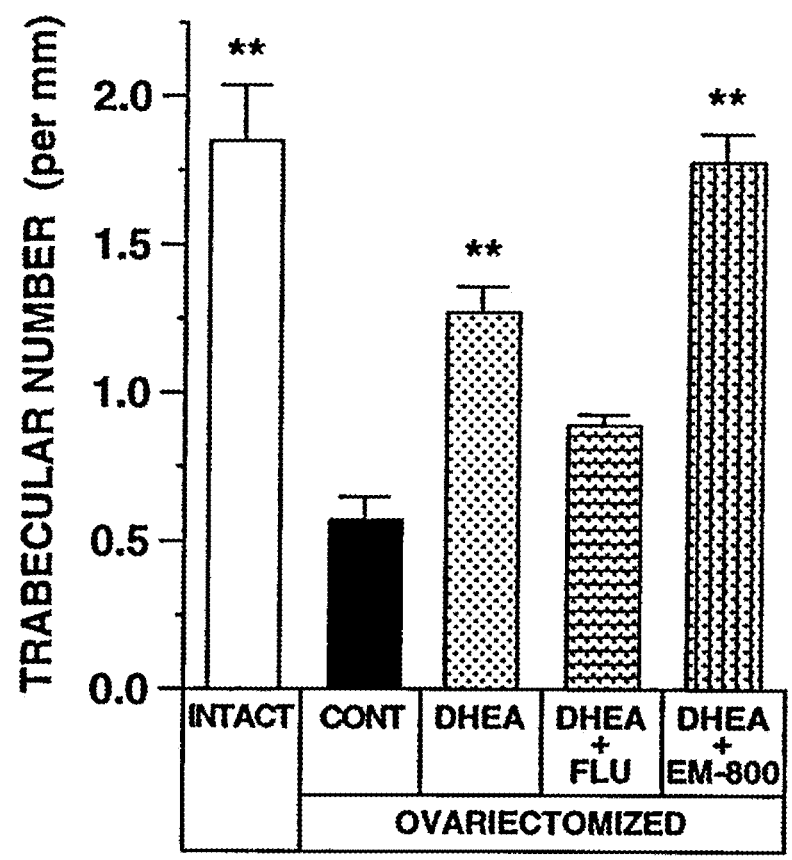
FIG. 16 shows the effect of 12-month treatment with dehydroepiandrosterone (DHEA) alone or in combination with Flutamide or EM-800 on trabecular number in ovariectomized rats. Intact animals are added as additional controls. Data are presented as mean±SEM ** p<0.01 versus OVX Control.

From a value of 0.57±0.08 per mm in ovariectomized rats, treatment with DHEA resulted in a 137% increase in trabecular bone number compared to ovariectomized controls. The stimulatory effect of DHEA thus reached 1.27±0.1 per mm while simultaneous treatment with EM-800 and DHEA resulted in an additional 28% increase in trabecular bone number ($p<0.01$) compared to that achieved by DHEA alone (FIG. 16). Similarly, the addition of EM-800 to DHEA treatment, resulted in an additional 15% ($p<0.05$) decrease in trabecular bone separation, compared to that achieved with DHEA alone, thus leading to values not different from those seen in intact controls.

Figure 15:
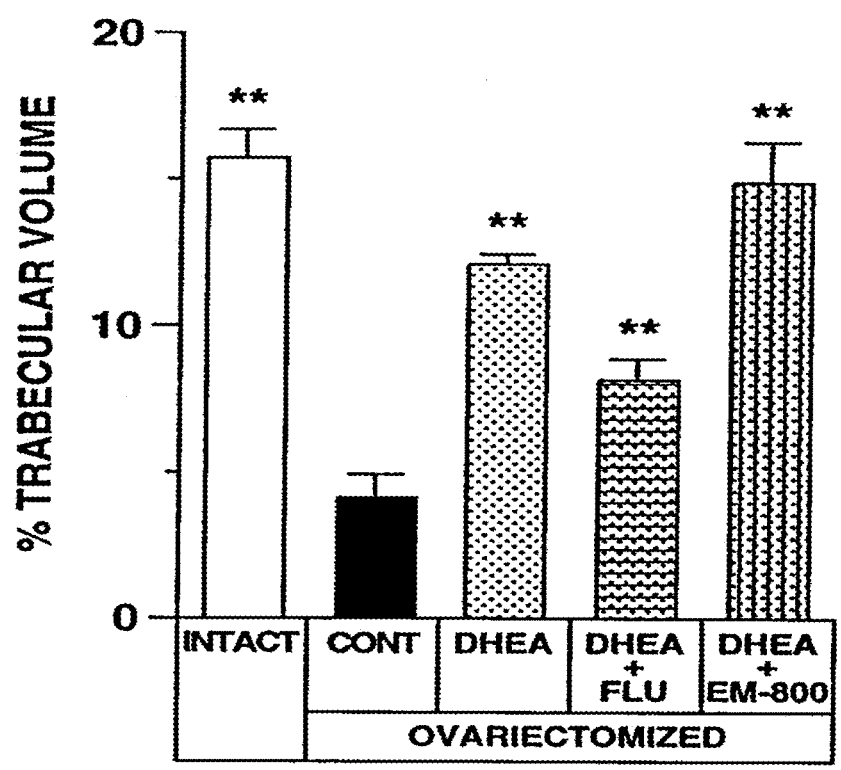
FIG. 15 shows the effect of 12-month treatment with dehydroepiandrosterone (DHEA) alone or in combination with Flutamide or EM-800 on trabecular bone volume in ovariectomized rats. Intact animals are added as additional controls. Data are presented as mean±SEM ** p<0.01 versus OVX Control.
Figure 17:
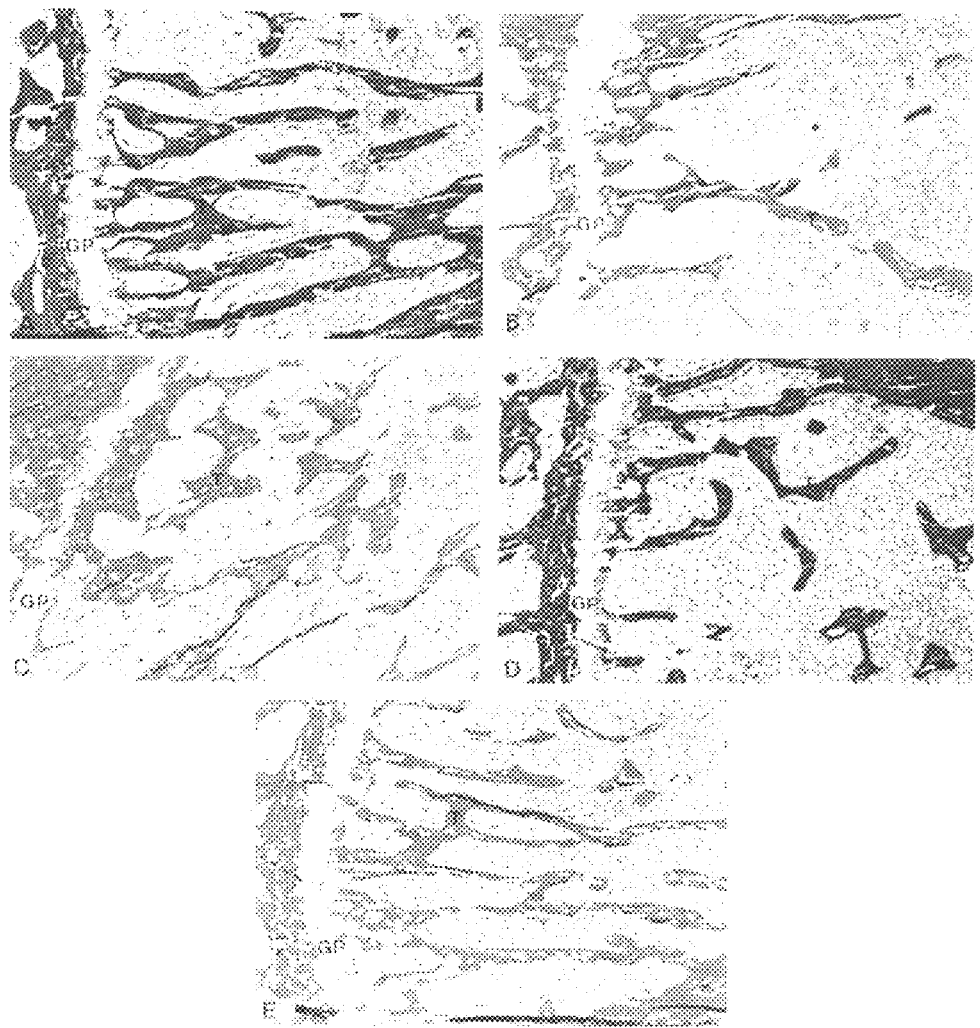
FIG. 17 shows proximal tibia metaphyses from intact control (A), ovariectomized control (B), and ovariectomized rats treated with DHEA alone (C) or in combination with Flutamide (D) or EM-800 (E). Note the reduced amount of trabecular bone (T) in ovariectomized control animals (B), and the significant increase in trabecular bone volume (T) induced after DHEA administration (C). The addition of Flutamide to DHEA partially blocked the effect of DHEA on the trabecular bone volume (D), whereas the combination of DHEA and EM-800 provided complete protection against the ovariectomy-associated bone loss. Modified trichrome Masson-Goldner, magn.×80. T: Trabeculae, GP: Growth Plate.

As complement to the numerical data presented in FIGS. 15,16, FIG. 17 illustrates the increase in trabecular bone volume in the proximal tibia metaphysis induced by DHEA in ovariectomized treated animals (C) compared to ovariectomized controls (B), as well as the partial inhibition of the stimulatory effect of DHEA after the addition of Flutamide to DHEA treatment (D). On the other hand, administration of DHEA in combination with EM-800 resulted in a complete prevention of the ovariectomy-induced osteopenia (E), the trabecular bone volume being comparable to that seen in intact controls (A).

cholesterol further to $0.63\pm0.09$ mmol/l ($p<0.01$), thus reaching a 65% inhibitory effect. No statistically significant change was observed in serum triglyceride levels with any of the treatments used (Table 2).

It is also of interest to note that the potent inhibitory effect of EM-800 on serum cholesterol is not prevented by simultaneous treatment with DHEA (Luo et al., 1997).

The bone loss observed at menopause in women is believed to be related to an increase in the rate of bone resorption which is not fully compensated by the secondary increase in bone formation. In fact, the parameters of both bone formation and bone resorption are increased in osteoporosis and both bone resorption and formation are inhibited by estrogen replacement therapy. The inhibitory effect of

TABLE 1

| GROUP | URINE | | | SERUM |
|---|---|---|---|---|
| | CALCIUM (nmol/24 h/100 g) | PHOSPHORUS (nmol/24 h/100 g) | HP/Cr (μmol/mmol) | tALP (IU/L) |
| CONTROL | 23.17 ± 1.55 | 132.72 ± 6.08 | 13.04 ± 2.19 | 114.25 ± 14.04 |
| DHEA (10 mg) | 25.87 ± 3.54 | 151.41 ± 14.57 | 14.02 ± 1.59 | 198.38 ± 30.76* |
| EM-800 (75 μg) | 17.44 ± 4.5 | 102.03 ± 25.13 | 6.81 ± 0.84** | 114.11 ± 11.26 |
| DHEA + EM-800 | 3.71 ± 0.75** | 59.06 ± 4.76** | 4.06 ± 0.28** | 204.38 ± 14.20** |

TABLE 2

Effect of 12-month treatment with dehydroepiandrosterone (DHEA) administered alone or in combination with Flutamide (FLU) or EM-800 on bone markers and serum lipids.

| Group | Alkaline phosphatase IU/L | OH-proline/ creatinin μmol/mmol | Cholesterol mmol/L | Triglycerides mmol/L |
|---|---|---|---|---|
| Intact Control | 30 ± 3** | 15.4 ± 1.3 | 2.28 ± 0.12 | 1.4 ± 0.2 |
| OVX Control | 51 ± 4 | 11.7 ± 1.2 | 2.29 ± 0.16 | 1.1 ± 0.1 |
| OVX + DHEA | 201 ± 25** | 7.3 ± 1.0* | 1.78 ± 0.16* | 0.8 ± 0.1 |
| OVX + DHEA + FLU | 103 ± 10** | 14.5 ± 1.2 | 2.27 ± 0.15 | 0.8 ± 0.1 |
| OVX + DHEA + EM-800 | 202 ± 17** | 6.4 ± 1.0** | 0.63 ± 0.09** | 1.0 ± 0.2 |

*$p < 0.05$;
**$p < 0.01$ versus OVX Control

The importance of the androgenic component of the stimulatory effect of DHEA on bone histomorphometry is also supported by the effect of DHEA on markers of bone formation and resorption. The concentration of serum alkaline phosphatase, a marker of bone formation (Meunier et al. 1987, Lauffenburger et al. 1977), was increased from 51±4 IU/L in OVX controls to 201±25 IU/L in DHEA-treated animals, suggesting a stimulatory effect of DHEA on bone formation (Table 2). FLU reversed by 65% the stimulatory effect of DHEA on this parameter while EM-800 had no significant effect. On the other hand, since hydroxyproline released during collagen degradation is not reutilized in collagen synthesis, it is a useful marker of collagen metabolism or osteoclastic bone resorption. In the present study, the urinary hydroxyproline/creatinine ratio decreased from 11.7±1.2 μmol/mmol in OVX controls to 7.3±1.0 μmol/mmol ($p<0.05$) in DHEA-treated rats (Table 2). The administration of FLU completely prevented the inhibitory effect of DHEA on this parameter while EM-800 had no statistically significant influence on the effect of DHEA.

Moreover, serum cholesterol was reduced by 22% from 2.29±0.16 to 1.78±0.16 mmol/l ($p<0.05$) by DHEA treatment, an effect neutralized by concomitant treatment with the pure antiandrogen FLU. The addition of the pure antiestrogen EM-800, on the other hand, decreased total serum estrogen replacement on bone formation is thus believed to result from a coupled mechanism between bone resorption and bone formation, such that the primary estrogen-induced reduction in bone resorption entrains a reduction in bone formation (Parfitt, 1984).

Cancellous bone strength and subsequent resistance to fracture do not only depend upon the total amount of cancellous bone but also on the trabecular microstructure, as determined by the number, size, and distribution of the trabeculae. The loss of ovarian function in postmenopausal women is accompanied by a significant decrease in total trabecular bone volume (Melsen et al., 1978; Vakamatsou et al., 1985), mainly related to a decrease in the number and, to a lesser degree, in the width of trabeculae (Weinstein and Hutson, 1987).

In order to facilitate the combination therapy aspect of the invention, for any indication discussed herein, the invention contemplates pharmaceutical compositions which include the SERM and the sex steroid precursor in a single composition for simultaneous administration. The composition may be suitable for administration in any traditional manner including but not limited to oral administration, subcutaneous injection, intramuscular injection or percutaneous administration. In other embodiments, a kit is provided wherein the kit includes one or more SERM and sex steroid precursor in separate or in one container. The kit may include appropriate materials for oral administration, e.g. tablets, capsules, syrups and the like and for transdermal administration, e.g., ointments, lotions, gels, creams, sustained release patches and the like.

Applicants believe that administration of SERMs or antiestrogens and sex steroid precursors has utility in the treatment and/or reduction of the incidence of hot flushes and sweat. The active ingredients of the invention (whether SERM, antiestrogen or precursor or otherwise) may be formulated and administered in a variety of ways. When administered together in accordance with the invention, the active ingredients may be administered simultaneously or separately.

Active ingredient for transdermal or transmucosal is preferably from 0.01% to 1%, DHEA or 5-diol. Alternatively, the active ingredient may be placed into a vaginal ring or a transdermal patch having structures known in the art, for example, structures such as those set forth in E.P. Patent No. 0279982 or in an intravaginal cream, gel, ovule, or suppository.

When formulated as an ointment, lotion, gel, cream, ovule, or suppository or the like, the active compound is admixed with a suitable carrier which is compatible with human skin or mucosa and which enhances transdermal or transmucosal penetration of the compound through the skin or mucosa. Suitable carriers are known in the art and include but are not limited to Klucel HF and Glaxal base. Some are commercially available, e.g., Glaxal base available from Glaxal Canada Limited Company. Other suitable vehicles can be found in Koller and Buri, S. T. P. Pharma 3(2), 115-124, 1987. The carrier is preferably one in which the active ingredient(s) is (are) soluble at ambient temperature at the concentration of active ingredient that is used. The carrier should have sufficient viscosity to maintain the inhibitor on a localized area of skin or mucosa to which the composition has been applied, without running or evaporating for a time period sufficient to permit substantial penetration of the precursor through the localized area of skin or mucosa and into the bloodstream where it will cause a desirable clinical effect. The carrier is typically a mixture of several components, e.g. pharmaceutically acceptable solvents and a thickening agent. A mixture of organic and inorganic solvents can aid hydrophylic and lipophylic solubility, e.g. water and an alcohol such as ethanol.

When formulated as an ovule or a vaginal suppository or the like, the active compound is admixed with a suitable carrier which is compatible with human vaginal mucosa. Preferred carriers are hard fats (mixture of glycerides of saturated fatty acids), particularly Witepsol, and specially Witepsol H-15 base (available from Medisca, Montreal, Canada). Any other lipophilic base such as Fattibase, Wecobee, cocoa butter, theobroma oil or other combinations of Witepsol bases could used.

Preferred sex steroid precursors are dehydroepiandrosterone (DHEA) (available, for example, from Proquina, Orizaba, Veracruz, Mexico).

The carrier may also include various additives commonly used in ointments, lotions and suppositories and well known in the cosmetic and medical arts. For example, fragrances, antioxidants, perfumes, gelling agents, thickening agents such as carboxymethylcellulose, surfactants, stabilizers, emollients, coloring agents and other similar agents may be present.

Treatment in accordance with the invention is suitable for indefinite continuation. The SERM or antiestrogenic compound and the sex steroid precursor can also be administered, by the oral route, and may be formulated with conventional pharmaceutical excipients, e.g. spray dried lactose, microcrystalline cellulose, and magnesium stearate into tablets or capsules for oral administration.

The active substances can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycol. Of course, taste-improving substances can be added in the case of oral administration forms.

As further forms, one can use plug capsules, e.g. of hard gelatin, as well as closed soft-gelatin capsules comprising a softener or plasticizer, e.g. glycerin. The plug capsules contain the active substance preferably in the form of granulate, e.g. in mixture with fillers, such as lactose, saccharose, mannitol, starches, such as potato starch or amylopectin, cellulose derivatives or highly dispersed silicic acids. In solf-gelatin capsules, the active substance is preferably dissolved or suspended in suitable liquids, such as vegetable oils or liquid polyethylene glycols.

The lotion, ointment, gel or cream should be thoroughly rubbed into the skin so that no excess is plainly visible, and the skin should not be washed in that region until most of the transdermal penetration has occurred preferably at least 4 hours and, more preferably, at least 6 hours.

A transdermal patch may be used to deliver precursor in accordance with known techniques. It is typically applied for a much longer period, e.g., 1 to 4 days, but typically contacts active ingredient to a smaller surface area, allowing a slow and constant delivery of active ingredient.

A number of transdermal drug delivery systems that have been developed, and are in use, are suitable for delivering the active ingredient of the present invention. The rate of release is typically controlled by a matrix diffusion, or by passage of the active ingredient through a controlling membrane.

Mechanical aspects of transdermal devices are well known in the rat, and are explained, for example, in U.S. Pat. Nos. 5,162,037, 5,154,922, 5,135,480, 4,666,441, 4,624,665, 3,742,951, 3,797,444, 4,568,343, 5,064,654, 5,071,644, 5,071,657, the disclosures of which are incorporated herein by reference. Additional background is provided by European Patent 0279982 and British Patent Application 2185187.

The device may be any of the general types known in the art including adhesive matrix and reservoir-type transdermal delivery devices. The device may include drug-containing matrixes incorporating fibers which absorb the active ingredient and/or carrier. In a reservoir-type device, the reservoir may be defined by a polymer membrane impermeable to the carrier and to the active ingredient.

In a transdermal device, the device itself maintains active ingredient in contact with the desired localized skin surface. In such a device, the viscosity of the carrier for active ingredient is of less concern than with a cream or gel. A solvent system for a transdermal device may include, for example, oleic acid, linear alcohol lactate and dipropylene glycol, or other solvent systems known in the art. The active ingredient may be dissolved or suspended in the carrier.

For attachment to the skin, a transdermal patch may be mounted on a surgical adhesive tape having a hole punched in the middle. The adhesive is preferably covered by a release liner to protect it prior to use. Typical material suitable for release includes polyethylene and polyethylenecoated paper, and preferably silicone-coated for ease of removal. For applying the device, the release liner is simply peeled away and the adhesive attached to the patient's skin. In U.S. Pat. No. 5,135,480, the disclosure of which is incorporated by reference, Bannon et al., describe an alternative device having a non-adhesive means for securing the device to the skin.

It is necessary only that SERM, antiestrogen and sex steroid precursor be administered in a manner and at a dosage sufficient to allow blood serum concentration of each to obtain desired levels. In accordance with the combination therapy of the invention, concentration of the SERM is maintained within desired parameters at the same time that sex steroid precursor concentration is maintained within desired parameters One preferred sex steroid precursor is DHEA, although DHEA-S and analogs discussed below are also especially effective for the reasons stated below.

A selective estrogen receptor modulator of the invention has a molecular formula with the following features: a) two aromatic rings spaced by 1 to 2 intervening carbon atoms, both aromatic rings being either unsubstituted or substituted by a hydroxyl group or a group converted in vivo to hydroxyl; and b) a side chain possessing an aromatic ring and a tertiary amine function or salt thereof.

One preferred SERM of the invention is Acolbifene:

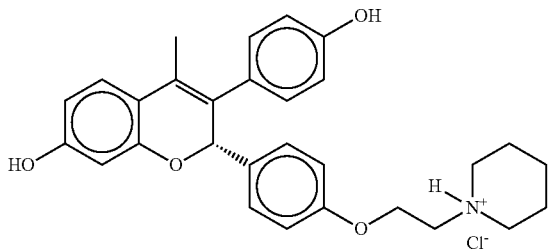

Acolbifene (also called EM-652.HCl; EM-1538) is the hydrochloride salt of the potent antiestrogen EM-652. It is disclosed in U.S. Pat. No. 6,710,059 B1. Another preferred SERM is Lasoxifene (Oporia; CP-336,156; (−)-cis-(5R,6S)-6-phenyl-5-[4-(2-pyrrolidin-1-ylethoxy)phenyl]-5,6,7,8-tetrahydronaphthalen-2-ol, D-(−)-tartrate salt) (available from Pfizer Inc., USA).

Another preferred SERM is Bazedoxifene (TSE 424; WAY-TSE 424; WAY 140424; 1-[[4-[2-(hexahydro-1H-azepin-1-yl)ethoxy]phenyl]methyl]-2-(4-hydroxyphenyl)-3-methyl-1H-indol-5-ol, acetate) developed by Wyeth Ayers (USA) and disclosed in JP10036347 (American home products corporation) and approved in USA for the prevention of postmenopausal osteoporosis and non-steroidal estrogen derivatives described in WO 97/32837. Other preferred SERMs of the invention include Tamoxifen ((Z)-2-[4-(1,2-diphenyl-1-butenyl) phenoxy]-N,N-dimethylethanamine) (available from Zeneca, UK), Toremifene ((Z)-2-[4-(4-Chloro-1,2-diphenyl-1-butenyl)phenoxy]-N,N-dimethyl-ethanamine) available from Orion, Finland, under the trademark Fareston or Schering-Plough), Droloxifene ((E)-3-[1-[4-[2-(Dimethylamino) ethoxy]phenyl]-2-phenyl-1-butenyl] phenol) and, from Eli Lilly and Co., USA: Raloxifene ([2-(4-hydroxyphenyl)-6-hydroxybenzo[b]thien-3-yl][4-[2-(1-piperidinyl)ethoxy]phenyl]-methanone hydrochloride), LY 335124, LY 326315, LY 335563 (6-hydroxy-3-[4-[2-(1-piperidinyl)ethoxy]phenoxyl]-2-(4-hydroxyphenyl)benzo[b]thiopene hydrochloride) and Arzoxifene (LY 353381, 6-hydroxy-3-[4-[2-(1-piperidinyl)ethoxy]phenoxyl]-2-(4-methoxyphenyl)benzo[b]thiophene hydrochloride). Other preferred SERMs are Idoxifene ((E)-1-[2-[4-[1-(4-Iodophenyl)-2-phenyl-1-butenyl]phenoxy]ethyl]pyrrolidine) (SmithKline Beecham, USA), Levormeloxifene (3,4-trans-2,2-dimethyl-3-phenyl-4-[4-(2-(2-(pyrrolidin-1-yl)ethoxy) phenyl]-7-methoxychroman) (Novo Nordisk, A/S, Denmark) which is disclosed in Shalmi et al. WO 97/25034, WO 97/25035, WO 97/25037, WO 97/25038; and Korsgaard et al. WO 97/25036), GW5638 (described by Willson et al., 1997) and indole derivatives (disclosed by Miller et al., EP 0802183A1) Are also included, Iproxifen (TAT 59; (E)-4-[1-[4-[2-(dimethylamino)ethoxy]phenyl]-2-[4-(1-methyl-ethyl)phenyl]-1-butenyl]phenol dihydrogen phosphate) from Taiho (Japan), Ospemifene (FC 1271; ((Z)-2-[4-(4-chloro-1,2-diphenyl-1-butenyl)phenoxyl]ethanol) from available from Orion-Farmos Pharmaceutica, Finland, SERM 3471, HMR 3339 and HMR 3656 from Sanofi-Aventis (France), SH 646 from Schering AG, Germany, Pipendoxifene (ERA 923) developed by Wyeth-Ayers, non-steroidal estrogen derivatives described in WO 97/3283, Fispemifene developed by QuatRx (USA) and CC 8490 developed by Celgene in USA.

Any SERM used as required for efficacy, as recommended by the manufacturer, can be used. Appropriate dosages are known in the art. Any other non steroidal antiestrogen commercially available can be used according to the invention. Any compound having activity similar to SERMs (example: Raloxifene can be used).

SERMs administered in accordance with the invention are preferably administered in a dosage range between 0.01 to 10 mg/kg of body weight per day (preferably 0.05 to 1.0 mg/kg), with 5 mg per day, especially 10 mg per day, in two equally divided doses being preferred for a person of average body weight when orally administered, or in a dosage range between 0.003 to 3.0 mg/kg of body weight per day (preferably 0.015 to 0.3 mg/ml), with 1.5 mg per day, especially 3.0 mg per day, in two equally divided doses being preferred for a person of average body weight when parentally administered (i.e. intramuscular, subcutaneous or percutaneous administration). Preferably the SERMs are administered together with a pharmaceutically acceptable diluent or carrier as described below.

One preferred antiestrogen of the invention is fulvestrant (Faslodex; ICI-182 7807α-[9-(4,4,5,5,5-pentafluoro-pentyl-sulphinyl)nonyl]oestra-1,3,5(10)-triene-3,17(3-diol) which is intramuscularly administered with the dosage of 250 mg per month available from AstraZeneca Canada Inc., Mississauga, Ontario, Canada.

With respect to all of the dosages recommended herein, the attending clinician should monitor individual patient response and adjust dosage accordingly.

EXAMPLES

Example 1

In the mammary gland, androgens are formed from the precursor steroid dehydroepiandrosterone (DHEA). Clinical evidence indicates that androgens have inhibitory effects on breast cancer. Estrogens, on the other hand, stimulate the development and growth of breast cancer. We studied the effect of DHEA alone or in combination with the newly described pure antiestrogen, EM-800, on the growth of tumor xenografts formed by the human breast cancer cell line ZR-75-1 in ovariectomized nude mice.

Mice received daily subcutaneous injections of 0.5 µg estrone (an estrogenic hormone) immediately after ovariectomy. EM-800 (15, 50 or 100 µg) was given orally once daily. DHEA was applied twice daily (total dose 0.3, 1.0 or 3.0 mg) to the dorsal skin either alone or in combination with a 15 µg daily oral dose of EM-800. Changes in tumor size in response to the treatments were assessed periodically in relation to the measurements made on the first day. At the end of the experiments, tumors were dissected and weighed.

A 9.4-fold increase in tumor size in 9.5 months was observed in ovariectomized mice receiving estrone alone in comparison with mice not receiving estrone. Administration of 15, 50 or 100 µg EM-800 in estrone-supplemented ovariectomized led to inhibitions of 88%, 93%, and 94% in tumor size, respectively. DHEA, on the other hand, at doses of 0.3, 1.0 or 3.0 mg inhibited terminal tumor weight by 67%, 82%, and 85%, respectively. Comparable inhibitions in tumor size were obtained with a daily 15 µg oral dose of EM-800 with or without different doses of percutaneous DHEA. DHEA and EM-800 independently suppressed the growth of estrone-stimulated ZR-75-1 mouse xenograft tumors in nude mice. Administration of DHEA at the defined doses does not alter the inhibitory effect of EM-800.

Materials and Methods

ZR-75-1 Cells

ZR-75-1 human breast cancer cells were obtained from the American Type Culture Collection (Rockville, Md.) and routinely cultured as monolayers in RPMI 1640 medium supplemented with 2 mM L-glutamine, 1 mM sodium pyruvate, 100 IU penicillin/ml, 100 µg streptomycin/ml, and 10% fetal bovine serum, under a humidified atmosphere of 95% air/5% $CO_2$ at 37° C. as described (Poulin and Labrie, 1986; Poulin et al., 1988). Cells were passaged weekly after treatment with 0.05% trypsin: 0.02% EDTA (w/v). The cell cultures used for the experiments described in this report were derived from passage 93 of the cell line ZR-75-1.

Animals

Female homozygous Harlan Sprague-Dawley (nu/nu) athymic mice (28- to 42-day-old) were obtained from HSD (Indianapolis, Ind., USA). Mice were housed in vinyl cages with air filter tops in laminar air flow hoods and maintained under pathogen-limited conditions. Cages, bedding, and food were autoclaved before use. Water was autoclaved, acidified to pH 2.8, and provided ad libitum.

Cell Inoculation

Mice were bilaterally ovariectomized (OVX) one week before tumor cell inoculation under anesthesia achieved by intraperitoneal injection of 0.25 ml/animal of Avertin (amylic alcohol: 0.8 g/100 ml 0.9% NaCl; and tribromo ethanol: 2 g/100 ml 0.9% NaCl). $1.5 \times 10^6$ ZR-75-1 cells in logarithmic growth phase were harvested after the treatment of monolayer with 0.05% trypsin/0.02% EDTA (w/v), were suspended in 0.1 ml of culture medium containing 25% Matrigel and were inoculated subcutaneously on both flanks of the animals using a 1 inch-long 20-gauge needle as described previously (Dauvois et al., 1991). In order to facilitate growth of the tumors, each animal received daily subcutaneous injection of 10 µg of estradiol ($E_2$) in vehicle composed of 0.9% NaCl 5% ethanol 1% gelatin for 5 weeks. After appearance of palpable ZR-75-1 tumors, tumor diameter was measured with calipers and mice having tumor diameter between 0.2 and 0.7 cm were selected for this study.

Hormonal Treatment

All animals, except those in the control OVX group, received daily subcutaneous injections of 0.5 µg estrone ($E_1$) in 0.2 ml of 0.9% NaCl 5% ethanol 1% gelatin. In the indicated groups, DHEA was administered percutaneously twice daily at the doses of 0.3, 1.0 or 3.0 mg/animal applied in a volume of 0.02 ml on the dorsal skin area outside the area of tumor growth. DHEA was dissolved in 50% ethanol 50% propylene glycol. EM-800, ((+)-7-pivaloyloxy-3-(4'-pivaloyloxyphenyl)-4-methyl-2-(4"-(2'"-piperidinoethoxy) phenyl)-2H-benzopyran), was synthesized as described earlier (Gauthier et al., J. Med. Chem. 40: 2117-2122, 1997) in the medicinal chemistry division of the Laboratory of Molecular Endocrinology of the CHUL Research Center. EM-800 was dissolved in 4% (v/v) ethanol 4% (v/v) polyethylene glycol (PEG) 600 1% (w/v) gelatin 0.9% (w/v) NaCl. Animals of the indicated groups received daily oral doses of 15 µg, 50 µg, or 100 µg of EM-800 alone or in combination with DHEA while animals of the OVX group received the vehicle (0.2 ml 4% ethanol 4% PEG 600 1% gelatin 0.9% NaCl) alone. Tumors were measured once a week with Vernier calipers. Two perpendicular diameters in cms (L and W) were recorded and tumor area ($cm^2$) was calculated using the formula: $L/2 \times W/2 \times \pi$ (Dauvois et al., 1991). The area measured on the first day of treatment was taken as 100% and changes in tumor size were expressed as percentage of initial tumor area. In case of subcutaneous tumors in general, it is not possible to accurately access three dimensional volume of tumor, therefore, only tumors areas were measured. After 291 days (or 9.5 months) of treatment, the animals were sacrificed.

The categories of responses were evaluated as described (Dauvois et al., 1989a; Dauvois et al., 1989b; Labrie et al., 1995b). In short, partial regression corresponds to the tumors that regressed equal to or more than 50% of their original size; stable response refers to tumors that regressed less than 50% of the original size or progressed less than 50% of their original size, while complete regression refers to those tumors that were undetectable at the end of treatment. Progression refers to tumors that progressed more than 50% compared with their original size. At the end of the experiment, all animals were killed by decapitation. Tumors, uterus, and vagina were immediately removed, freed from connective and adipose tissues, and weighed.

Statistical Analysis

Statistical significance of the effects of treatments on tumor size was assessed using an analysis of variance (ANOVA) evaluating the effects due to DHEA, EM-800, and time, and repeated measures in the same animals performed at the initiation and at the end of the treatment (subjects within group factor). The repeated measures at time 0 and after 9.5 months of treatment constitute randomized blocks of animals. The time is thus analyzed as a within-block effect while both treatments are assessed as between-block effects. All interactions between main effects were included in the model. The significance of the treatment factors and of their interactions was analyzed using the subjects within group as the error term. Data were logtransformed. The hypotheses underlying the ANOVA assumed the normality of the residuals and the homogeneity of variance.

A posteriori pairwise comparisons were performed using Fisher's test for least significant difference. Main effects and the interaction of treatments on body weight and organ weight were analyzed using a standard two-way ANOVA with interactions. All ANOVAs were performed using SAS program (SAS Institute, Cary, N.C., USA). Significance of differences was declared using a 2-tailed test with an overall level of 5%. Categorical data were analyzed with a Kruskall-Wallis test for ordered categorical response variables (complete response, partial response, stable response, and progression of tumor). After overall assessment of a treatment effects, subsets of the results presented in Table 4 were analyzed adjusting the critical p-value for multiple comparisons. The exact p-values were calculated using StatXact program (Cytel, Cambridge, Mass., USA). Data are expressed as means±standard error of the mean (SEM) of 12 to 15 mice in each group.

Results

As illustrated in FIG. 3A, human ZR-75-1 tumors increased by 9.4-fold over 291 days (9.5 months) in ovariectomized nude mice treated with a daily 0.5 µg subcutaneously administered dose of estrone while in control OVX mice who received the vehicle alone, tumor size was decreased to 36.9% of the initial value during the course of the study.

Treatment with increasing doses of percutaneous DHEA caused a progressive inhibition of $E_1$-stimulated ZR-75-1 tumor growth. Inhibitions of 50.4%, 76.8%, and 80.0% were achieved at 9.5 months of treatment with the 0.3 mg, 1.0 mg, and 3.0 mg daily doses per animal of DHEA, respectively (FIG. 3A). In agreement with the decrease in total tumor load, treatment with DHEA led to a marked decrease of the average weight of the tumors remaining at the end of the experiment. In fact, average tumor weight decreased from 1.12±0.26 g in control $E_1$-supplemented ovariectomized nude mice to 0.37±0.12 g (P=0.005), 0.20±0.06 g (P=0.001), and 0.17±0.06 g (P=0.0009) in the groups of animals receiving the daily 0.3, 1.0 and 3.0 mg doses of DHEA, respectively (FIG. 3B).

At the daily doses of 15 µg, 50 µg, and 100 µg, the antiestrogen EM-800 inhibited estrogen-stimulated tumor size by 87.5% (P<0.0001), 93.5% (P<0.0001), and 94.0% (P=0.0003), respectively (FIG. 4A) when compared to the tumor size in control animals at 9.5 months. The tumor size reductions achieved with the three EM-800 doses are not significantly different between each other. As illustrated in FIG. 3B, tumor weight at the end of the 9.5-month study was decreased from 1.12±0.26 g in control $E_1$-supplemented OVX mice to 0.08±0.03 g, 0.03±0.01 g and 0.04±0.03 g in animals treated with the daily 15 µg, 50 µg, and 100 µg doses of EM-800, respectively (P<0.0001 at all doses of EM-800 vs $E_1$ supplemented OVX).

As mentioned above, the antiestrogen EM-800, at the daily oral dose of 15 µg, caused a 87.5% inhibition of estrone-stimulated tumor growth measured at 9.5 months. The addition of DHEA at the three doses used had no significant effect on the already marked inhibition of tumor size achieved with the 15 µg daily dose of the antiestrogen EM-800 (FIG. 4B). Thus, average tumor weight was dramatically reduced from 1.12±0.26 g in control estrone-supplemented mice to 0.08±0.03 g (P<0.0001), 0.11±0.04 g (P=0.0002), 0.13±0.07 g (P=0.0004) and 0.08±0.05 g (P<0.0001) in the animals who received the daily dose of 15 µg of the antiestrogen alone or in combination with the 0.3, 1.0, and 3.0 mg doses of DHEA, respectively (no significant difference was noted between the 4 groups) (FIG. 3B).

It was also of interest to examine the categories of responses achieved with the above-indicated treatments. Thus, treatment with the increasing doses of DHEA decreased, although not to a level of statistical significance (P=0.088), the number of progressing tumors from 87.5% in the control OVX animals supplemented with estrone to values of 50.0%, 53.3%, and 66.7% in the animals treated with the daily doses of 0.3, 1.0 or 3.0 mg of DHEA (Table 3). Complete responses, on the other hand, increased from 0% in the estrone-supplemented mice to 28.6%, 26.7%, and 20.0% in the animals receiving the 0.3, 1.0, and 3.0 mg daily doses of percutaneous DHEA. Stable responses, on the other hand, were measured at 12.5%, 21.4%, 20.0%, and 13.3% in the control $E_1$-supplemented mice and in the three groups of animals who received the above-indicated doses of DHEA, respectively. In control ovariectomized mice, the rates of complete, partial and stable responses were measured at 68.8%, 6.2%, and 18.8%, respectively, while progression was seen in only 6.2% of tumors (Table 3).

Complete responses or disappearance of the tumors were achieved in 29.4%, 33.3%, 26.7%, and 35.3% of tumors in the animals who received the antiestrogen EM-800 (P=0.0006) alone (15 µg) or in combination with the 0.3 mg, 1.0 mg, or 3.0 mg of DHEA, respectively. Progression, on the other hand, was seen in 35.3%, 44.4%, 53.3%, and 17.6% of the tumors, in the same groups of animals, respectively. There is no significant difference between the groups treated with EM-800, either alone or in combination with DHEA.

No significant effect of DHEA or EM-800 treatment was observed on body weight adjusted for tumor weight. Treatment of OVX mice with estrone, increased uterine weight from 28±5 mg in OVX control mice to 132±8 mg (P<0.01) while increasing doses of DHEA caused a progressive but relatively small inhibition of the stimulatory effect of estrone which reached 26% (P=0.0008) at the highest dose of DHEA used. It can be seen in the same figure that estrone-stimulated uterine weight was decreased from 132±8 mg in control estrone-supplemented mice to 49±3 mg, 36±2 mg, and 32±1 mg (P<0.0001 at all doses vs control) with the daily oral doses of 15 µg, 50 µg, or 100 µg of EM-800 (overall P<0.0001), respectively. Fifteen micrograms (15 µg) EM-800 in combination with the 0.3 mg, 1.0 mg or 3.0 mg daily doses of DHEA, uterine weight was measured at 46±3 mg, 59±5 mg and 69±3 mg, respectively.

On the other hand, treatment with estrone increased vaginal weight from 14±2 mg in OVX animals to 31±2 mg (P<0.01) while the addition of DHEA had no significant effect. Vaginal weight was then reduced to 23±1 mg, 15±1 mg, and 11±1 mg following treatment with the daily 15 µg, 50 µg or 100 µg doses of EM-800, respectively (overall p and pairwise P<0.0001 at all doses vs. control). In combination with the 0.3 mg, 1.0 mg or 3.0 mg doses of DHEA and of EM-800, vaginal weight was measured at 22±1 mg, 25±2 mg and 23±1 mg, respectively (N.S. for all groups versus 15 µg EM-800). It should be mentioned that at the highest dose used, namely 100 µg daily, EM-800 decreased uterine weight in estrone-supplemented OVX animals to a value not different from that of OVX controls while vaginal weight was reduced to a value below that measured in OVX controls (P<0.05). DHEA, probably due to its androgenic effects, partially counteracted the effect of EM-800 on uterine and vaginal weight.

TABLE 3

Effect of percutaneous administration of DHEA or oral administration of EM-800 alone or in combination for 9.5 months on the responses (complete, partial, stable, and progression) of human ZR-75-1 breast tumor xenografts in nude mice.

| GROUP | | TOTAL NUMBER OF ANIMALS | CATEGORY OF RESPONSE | | | |
|---|---|---|---|---|---|---|
| | | | Complete | Partial | Stable | Progression |
| | | | | Number and (%) | | |
| OVX | | 16 | 11 (68.8) | 1 (6.2) | 3 (18.8) | 1 (6.2) |
| OVX + E1 | (0.5 μg) | 16 | 0 (0) | 0 (0) | 2 (12.5) | 14 (87.5) |
| OVX + E1 (0.5 μg) + DHEA | 0.3 mg | 14 | 4 (28.6) | 0 (0) | 3 (21.4) | 7 (50.0) |
| | 1.0 mg | 15 | 4 (26.7) | 0 (0) | 3 (20.0) | 8 (53.3) |
| | 3.0 mg | 15 | 3 (20.0) | 0 (0) | 2 (13.3) | 10 (66.7) |
| OVX + E1 (0.5 μg) + EM-800 | 15 μg | 17 | 5 (29.4) | 1 (5.9) | 5 (29.4) | 6 (35.3) |
| | 50 μg | 16 | 4 (25.0) | 3 (18.8) | 5 (31.2) | 4 (25.0) |
| | 100 μg | 16 | 8 (50.0) | 0 (0) | 3 (18.8) | 5 (31.2) |
| OVX + E1 (0.5 μg) + EM-800 + DHEA | 0.3 mg | 18 | 6 (33.3) | 0 (0) | 4 (22.2) | 8 (44.4) |
| | 1.0 mg | 15 | 4 (26.7) | 0 (0) | 3 (20.0) | 8 (53.3) |
| | 3.0 mg | 17 | 6 (35.3) | 0 (0) | 8 (47.1) | 3 (17.6) |

$E_1$ = Estrone; DHEA = dehydroepiandrosterone; OVX = ovariectomized

Example 2

Example of Synthesis of the Preferred Compound of the Invention

Synthesis of (S)-(+)-7-hydroxy-3-(4'-hydroxyphenyl)-4-methyl-2-(4"-(2"'-piperidinoethoxy)phenyl)-2H-1-benzopyran hydrochloride EM-01538 (EM-652, HCl)

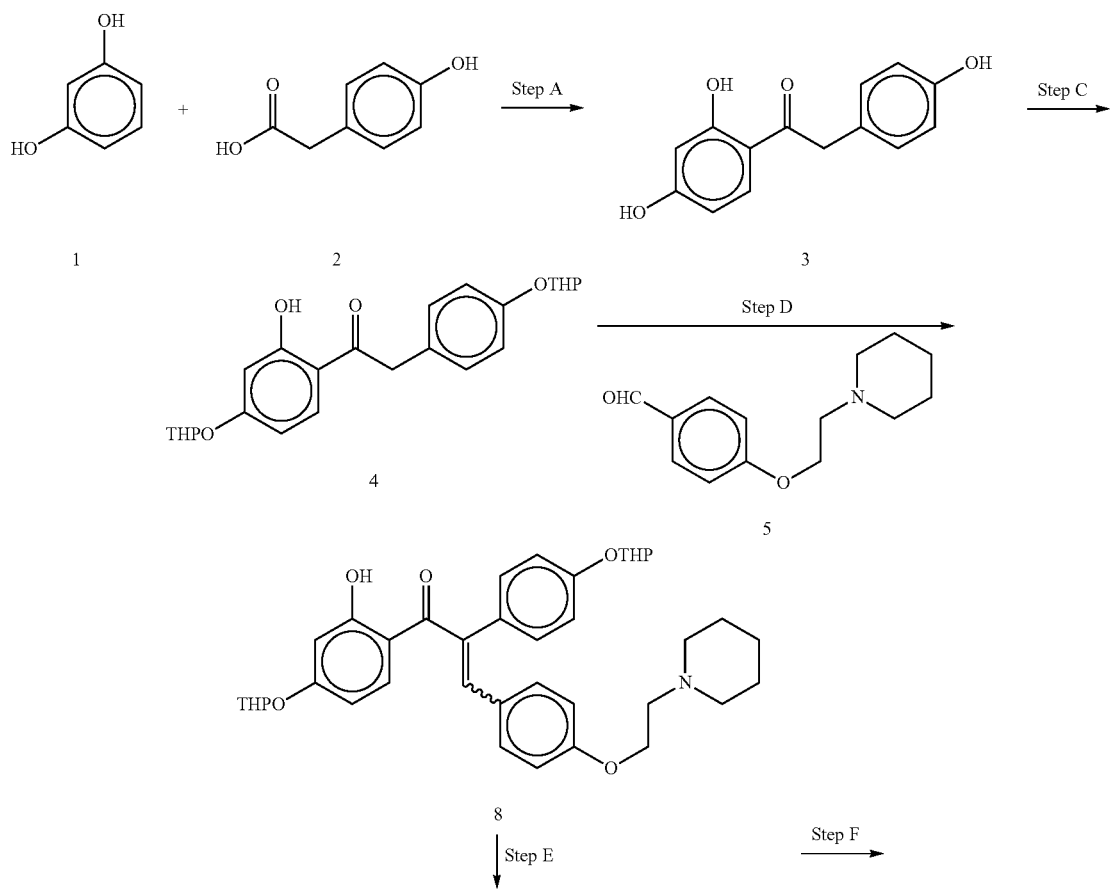

Scheme 1

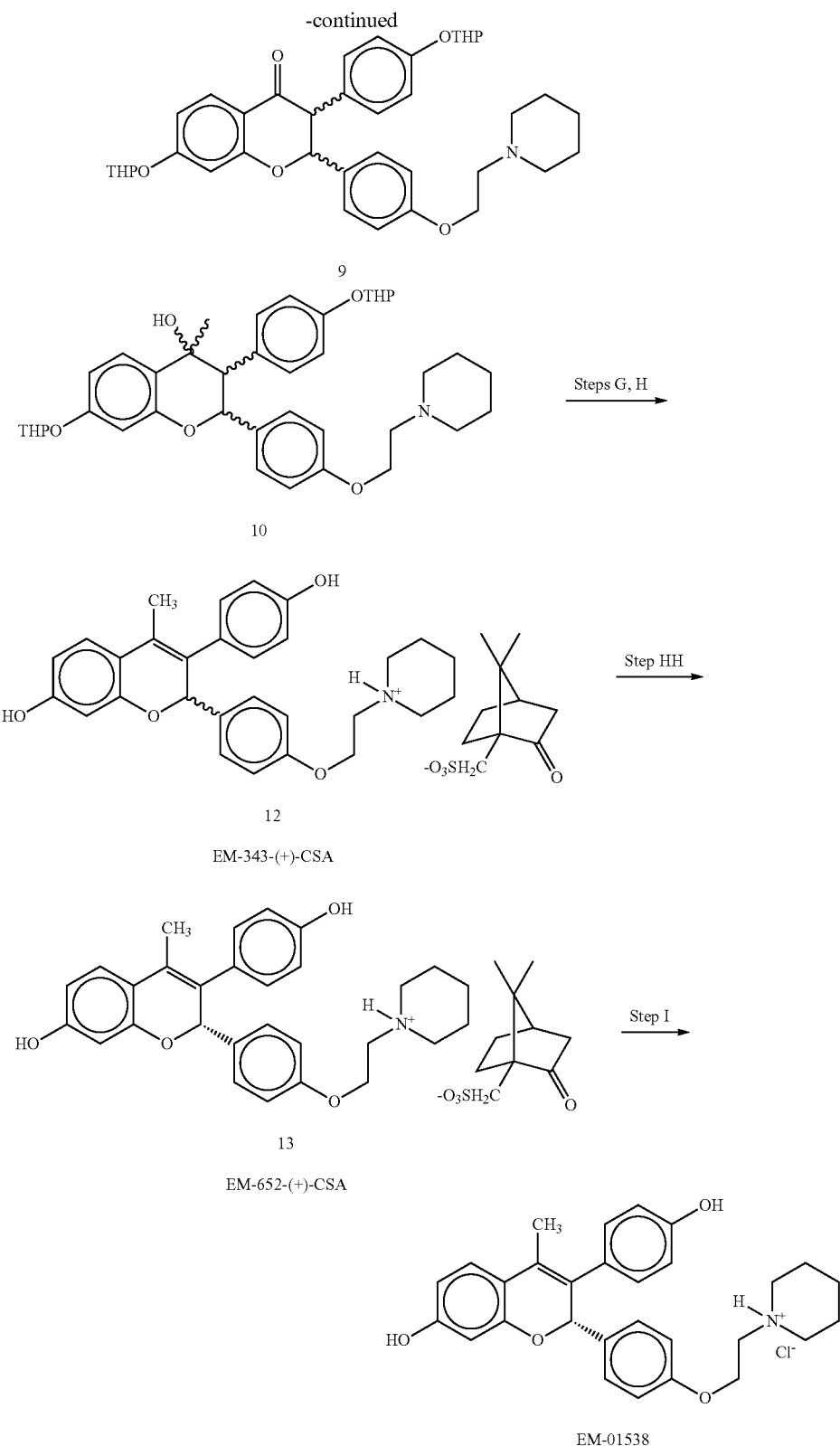
Step A: BF$_3$.Et$_2$O , toluene; 100° C.; 1 hour.
Step C: 3,4-dihydropyran, p-toluenesulfonic acid monohydrate, ethyl acetate; 25° C. under nitrogen, 16 hours, and then crystallization in isopropanol.
Steps D, E, and F:
(1) piperidine, toluene, Dean & Stark apparatus, reflux under nitrogen ; (2) 1,8-diazabicyclo[5,4,0]undec-7-ene, DMF, reflux 3 hours ;

(3) CH₃MgCl, THF, −20 to 0° C. and then room temperature for 24 hours;
Steps G, H: (1S)-(+)-10-camphorsulfonic acid, acetone, water, toluene, room temperature, 48 hours.
Step HH: 95% ethanol, 70° C., then room temperature 3 days.
Step HHR: Recycling of mother liquor and wash of step HH (S)-10-camphorsulfonic acid, reflux; 36 hours, then room temperature for 16 hours.
Step I:
(1) DMF aq., Na₂CO₃, ethyl acetate;
(2) Ethanol, dilute HCl;
(3) Water.

Synthesis of 2-tetrahydropyranyloxy-4-hydroxy-2'-(4"-tetrahydropyranyloxyphenyl)acetophenone (4)

A suspension of 2,4-dihydroxy-2'-(4"-hydroxyphenyl)acetophenone 3 (97.6 g, 0.4 mole) (available from Chemsyn Science Laboratories, Lenexa, Kans.) in 3,4-dihydropyran (218 ml, 3.39 mole) and ethyl acetate (520 ml) was treated with p-toluenesulfonic acid monohydrate (0.03 g, 0.158 mmole) at about 25° C. The reaction mixture was stirred under nitrogen with no external heating for about 16 hours. The mixture was then washed with a solution of sodium bicarbonate (1 g) and sodium chloride (5 g) in water (100 ml). The phases were separated and the organic phase was washed with brine (20 ml). Each wash was back extracted with 50 ml ethyl acetate. All the organic phases were combined and filtered through sodium sulfate. Solvent (about 600 ml) was removed by distillation at atmospheric pressure and isopropanol (250 ml) was added. Additional solvent (about 300 ml) was distilled at atmospheric pressure and isopropanol (250 ml) was added. Additional solvent (about 275 ml) was distilled at atmospheric pressure and isopropanol (250 ml) was added. The solution was cooled at about 25° C. with stirring and after about 12 hours, the crystalline solid was filtered, washed with isopropanol and dried (116.5 g, 70%).

Synthesis of 4-hydroxy-4-methyl-2-(4'-[2"-piperidino]-ethoxy)phenyl-3-(4'''-tetrahydropyranyloxy)phenyl-7-tetrahydropyranyloxychromane (10)

A solution of 2-tetrahydropyranyloxy-4-hydroxy-2'-(4"-tetrahydropyranyloxyphenyl)acetophenone 4 (1 kg, 2.42 mole), 4-[2-(1-piperidino)ethoxy]benzaldehyde 5 (594 g, 2.55 mole) (available from Chemsyn Science Laboratories, Lenexa, Kans.) and piperidine (82.4 g, 0.97 mole) (available from Aldrich Chemical Company Inc., Milwaukee, Wis.) in toluene (8 L) was refluxed under nitrogen with a Dean & Stark apparatus until one equivalent of water (44 mL) was collected. Toluene (6.5 L) was removed from the solution by distillation at atmospheric pressure. Dimethylformamide (6.5 L) and 1,8-diazabicyclo[5,4,0]undec-7-ene (110.5 g, 0.726 mole) were added. The solution was agitated for about 8 hours at room temperature to isomerize the chalcone 8 to chromanone 9 and then added to a mixture of water and ice (8 L) and toluene (4 L). The phases were separated and the toluene layer washed with water (5 L). The combined aqueous washes were extracted with toluene (3×4 L). The combined toluene extracts were finally washed with brine (3×4 L), concentrated at atmospheric pressure to 5.5 L and then cooled to −10° C. With continued external cooling and stirring under nitrogen, a 3M solution of methylmagnesium chloride in THF (2.5 L, 7.5 mole) (available from Aldrich Chemical Company Inc., Milwaukee, Wis.) was added, maintaining the temperature below 0° C. After all the Grignard reagent was added, the external cooling was removed and the mixture allowed warm to room temperature. The mixture was stirred at this temperature for about 24 hours. The mixture was again cooled to about −20° C. and with continued external cooling and stirring, saturated ammonium chloride solution (200 ml) was added slowly, maintaining the temperature below 20° C. The mixture was stirred for 2 hours and then added the saturated ammonium chloride solution (2 L) and toluene (4 L) and agitated for five minutes. The phases were separated and the aqueous layer extracted with toluene (2×4 L). The combined toluene extracts were washed with dilute hydrochloric acid until the solution became homogenous and then with brine (3×4 L). The toluene solution was finally concentrated at atmospheric pressure to 2 L. This solution was used directly in the next step.

Synthesis of (2R,S)-7-hydroxy-3-(4'-hydroxyphenyl)-4-methyl-2-(4"-[2'''-piperidino]ethoxy)phenyl)-2H-1-benzopyran (1S)-10-camphorsulphonic acid salt (±12)

To the toluene solution of 4-hydroxy-4-methyl-2-(4'-[2"-piperidino]-ethoxy)-phenyl-3-(4'''-tetrahydropyranyloxy)phenyl-7-tetrahydropyranyloxychromane (10) was added acetone (6 L), water (0.3 L) and (S)-10-camphorsulphonic acid (561 g, 2.42 mole) (available from Aldrich Chemical Company Inc., Milwaukee, Wis.). The mixture was agitated under nitrogen for 48 hours after which time the solid (2R,S)-7-hydroxy-3-(4'-hydroxyphenyl)-4-methyl-2-(4"-[2'''-piperidino]ethoxy)phenyl)-2H-1-benzopyran (1S)-10-camphorsulphonic acid salt (12) was filtered, washed with acetone and dried (883 g). This material was used in the next (HH) step without further purification.

Synthesis of (2S)-7-hydroxy-3-(4'-hydroxyphenyl)-4-methyl-2-(4"-[2'-piperidino]ethoxy)phenyl)-2H-1-benzopyran (1S)-10-camphorsulphonic acid salt (13, (+)-EM-652(1S)-CSA salt)

A suspension of (2R,S)-7-hydroxy-3-(4'-hydroxyphenyl)-4-methyl-2-(4"-[2'''-piperidino]ethoxy)phenyl)-2H-benzopyran (1S)-10-camphorsulphonic acid salt ±12 (759 g) in 95% ethanol was heated with stirring to about 70° C. until the solid had dissolved. The solution was allowed to cool to room temperature with stirring then seeded with a few crystals of (2S)-7-hydroxy-3-(4'-hydroxyphenyl)-4-methyl-2-(4"-[2'''-piperidino]ethoxy)phenyl)-2H-1-benzopyran (1S)-10-camphorsulphonic acid salt 13. The solution was stirred at room temperature for about three days in total. The crystals were filtered, washed with 95% ethanol and dried (291 g, 76%). The de of the product was 94.2% and the purity 98.8%.

Synthesis of (S)-(+)-7-hydroxy-3-(4'-hydroxyphenyl)-4-methyl-2-(4"-(2'-piperidinoethoxy)phenyl)-2H-1-benzopyran hydrochloride EM-01538 (EM-652, HCl)

A suspension of compound 13 (EM-652-(+)-CSA salt, 500 mg, 0.726 mmol) in dimethylformamide (11 μL, 0.15 mmol) was treated with an 0.5 M aqueous sodium carbonate solution (7.0 mL, 3.6 mmol), and stirred for 15 min. The suspension was treated with ethyl acetate (7.0 mL) and stirred during 4 h. The organic phase was then washed with an aqueous saturated sodium carbonate solution (2×5 mL)

and brine (1×5 mL) dried over magnesium sulfate, and concentrated. A solution of the resulting pink foam (EM-652) in ethanol (2 mL) was treated with 2 N hydrochloric acid (400 µL, 0.80 mmol), stirred for 1 h, treated with distilled water (5 mL), and stirred during 30 min. The resulting suspension was filtered, washed with distilled water (5 mL), dried in air and under high vacuum (65° C.) to give a creamy powder (276 mg, 77%): Fine off-white powder ; Scanning calorimetry: Melting peak onset at 219° C., ΔH=83 J/g ; $[\alpha]^{24}_D$=154° in methanol 10 mg/ml.; $^1$H NMR (300 MHz, CD$_3$OD) δ (ppm) 1.6 (broad, 2H, H-4'''), 1.85 (broad, 4H, H-3''' and 5'''), 2.03 (s, 3H, CH$_3$), 3.0 and 3.45 (broad, 4H, H-2''' and 6'''), 3.47 (t, J=4.9 Hz, 2H, H-3'''), 4.26 (t, J=4.9 Hz, 2H, H-2'''), 5.82 (s, 1H, H-2), 6.10 (d, J=2.3 Hz, 1H, H-8), 6.35 (dd, J=8.4, 2.43 Hz, 1H, H-6), 6.70 (d, J=8.6 Hz, 2H, H-3', and H-5'), 6.83 (d, J=8.7 Hz, 2H, H-3" and H-5"), 7.01 (d, J=8.5 Hz, 2H, H-2' and H-6'), 7.12 (d, J=8.4 Hz, 1H, H-5), 7.24 (d, J=8.6 Hz, 2H, H-2" and H-6"); $^{13}$C RMN (CD$_3$OD, 75 MHz) δ ppm 14.84, 22.50, 23.99, 54.78, 57.03, 62.97, 81.22, 104.38, 109.11, 115.35, 116.01, 118.68, 125.78, 126.33, 130.26, 130.72, 131.29, 131.59, 134.26, 154.42, 157.56, 158.96, 159.33.

Elemental Composition: C, H, N, Cl: Theory; 70.51, 6.53, 2.84, 7.18, %. Found: 70.31, 6.75, 2.65, 6.89%.

Example 3

Materials and Methods
Animals

Female BALB/c mice (BALB/cAnNCrlBR) weighing 18-20 g were obtained from Charles-River, Inc. (St-Constant, Quebec, Canada) and housed 5 per cage in a temperature (23±1° C.)- and light (12 h light/day, lights on at 7:15)-controlled environment. The mice were fed rodent chow and tap water ad libitum. The animals were ovariectomized (OVX) under Isoflurane anesthesia via bilateral flank incisions and randomly assigned to groups of 10 animals. Ten mice were kept intact as controls.
Treatments In the first experiment (FIGS. 11 to 14), tested compounds, namely EM-652.HCl, lasofoxifene (as free base; active and inactive enantiomers) and raloxifene, were administered orally by gavage once daily at doses of 1, 3 or 10 µg/animal for 9 days, starting 2 days after ovariectomy. In the second experiment (Table 6), TSE 424 was administered orally by gavage once daily at doses of 1, 3, 10 or 30 µg/animal for 9 days, starting 2 days after ovariectomy. In both experiments, to evaluate the antiestrogenic activity, treatment with estrone (E$_1$, 0.06 µg, s.c. injection, twice daily) was started 5 days post-ovariectomy and was administered for a 6 day-period. Compounds were dissolved in ethanol (4% final concentration) and administered in 0.4% methylcellulose. Mice in the intact and OVX control groups received the vehicle alone (4% ETOH-0.4% methylcellulose) during the 9-day period. The animals were killed by exsanguination at the abdominal aorta on the 11th morning following ovariectomy. The uteri and vagina were rapidly dissected, weighed, and kept in 10% buffered formalin for further histologic examination.

Article I. Results

Experiment 1

Figure 11:
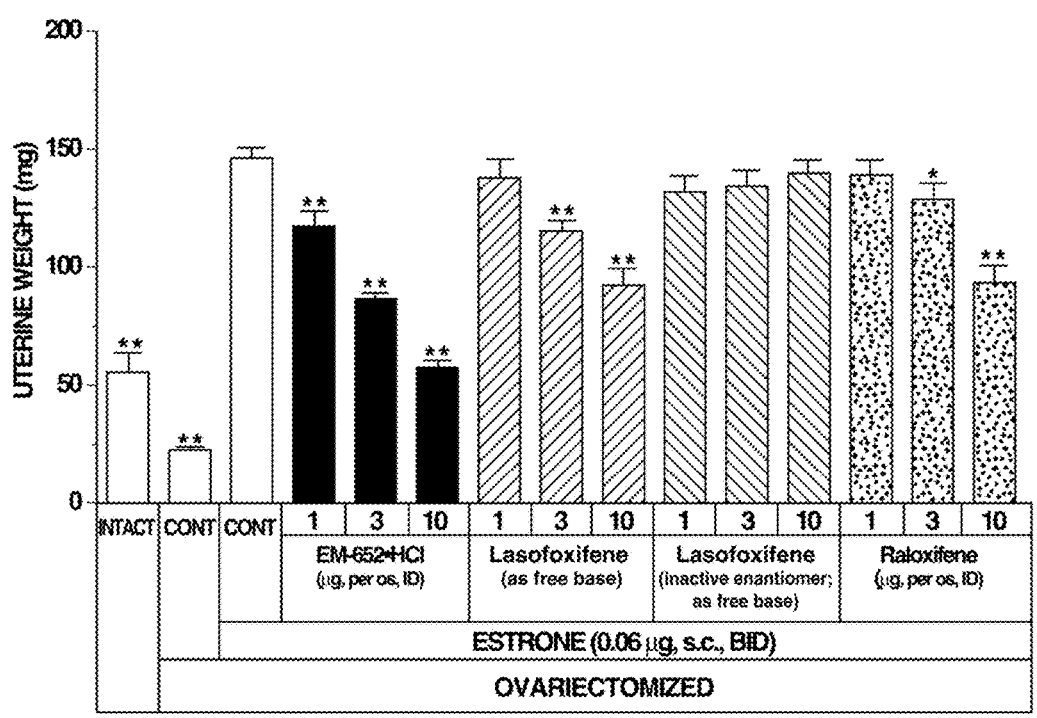
FIG. 11 shows the effect on uterine weight of increasing concentrations of EM-652.HCl, Lasofoxifene (free base; active and inactive enantiomers) and Raloxifene administered orally for 9 days to ovariectomized mice simultaneously treated with estrone. *p<0.05, **p<0.01 versus $E_1$-treated control.
Figure 12:
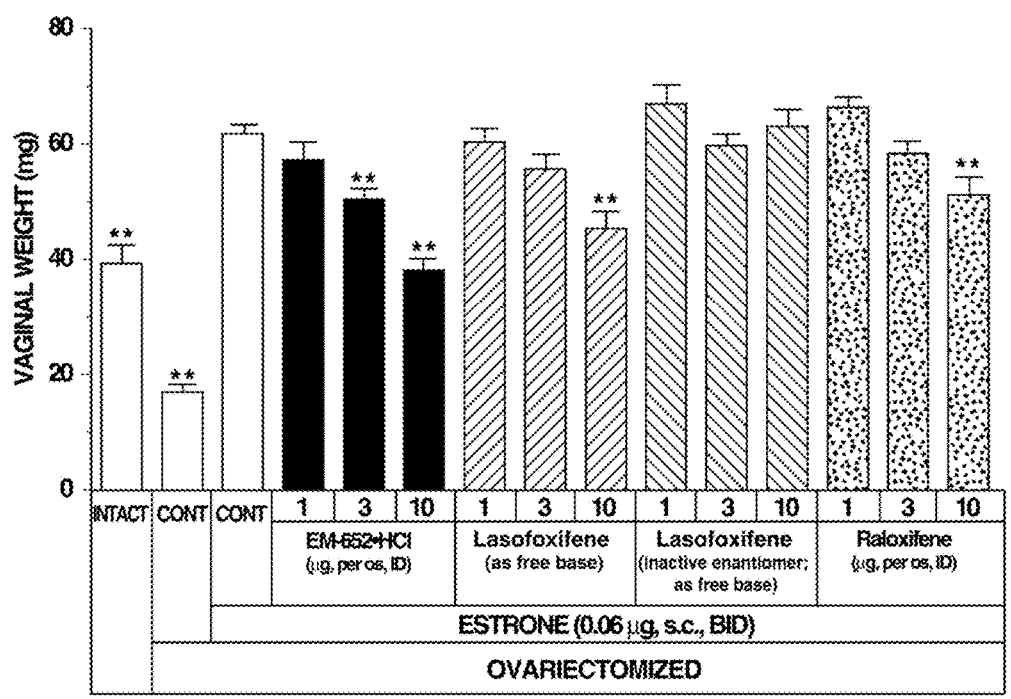
FIG. 12 shows the effect on vaginal weight of increasing concentrations of EM-652.HCl, Lasofoxifene (free base; active and inactive enantiomers) and Raloxifene administered orally for 9 days to ovariectomized mice simultaneously treated with estrone. **p<0.01 versus $E_1$-treated control.
Figure 13:
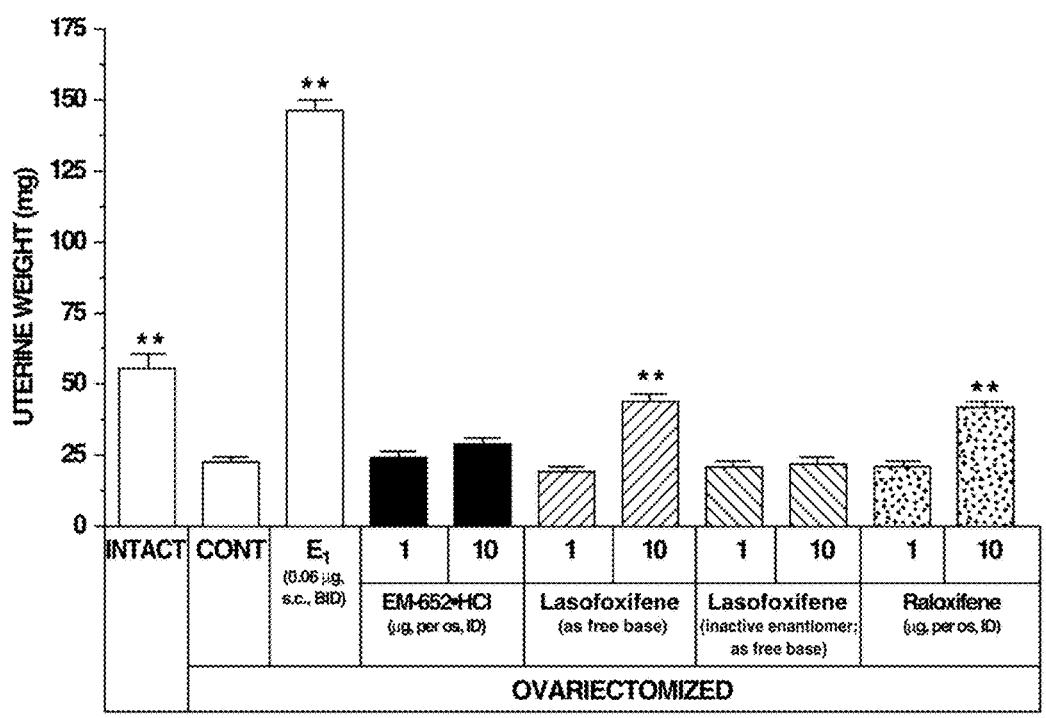
FIG. 13 shows the effect on uterine weight of 1 μg and 10 μg of EM-652.HCl, Lasofoxifene (free base; active and inactive enantiomers) and Raloxifene administered orally for 9 days to ovariectomized mice. **p<0.01 versus OVX control.
Figure 14:
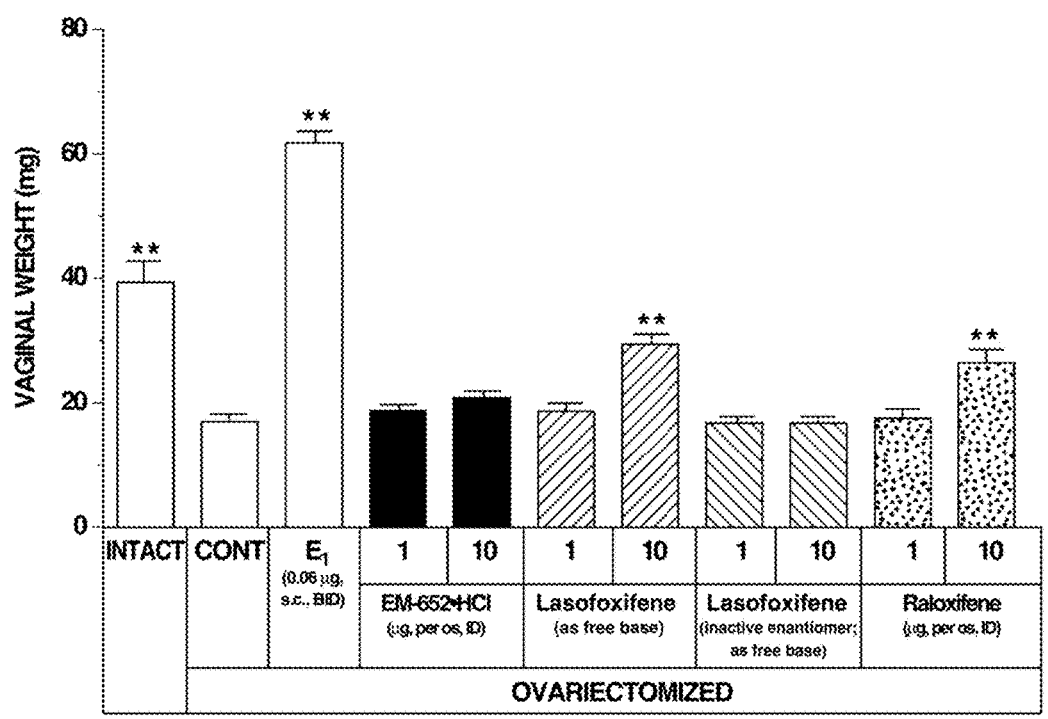
FIG. 14 shows the effect on vaginal weight of 1 μg and 10 μg of EM-652.HCl, Lasofoxifene (free base; active and inactive enantiomers) and Raloxifene administered orally for 9 days to ovariectomized mice. **p<0.01 versus OVX control.

As illustrated in FIG. 11, EM-652.HCl administered at the daily oral doses of 1 µg, 3 µg, and 10 µg caused respective 24%, 48%, and 72% inhibitions of estrone-stimulated uterine weight (p<0.01 for all doses versus control) while raloxifene administered at the same doses caused respective 6% (NS), 14% (p<0.01) and 43% (p<0.01) inhibitions of this parameter. Lasofoxifene (as free base), on the other hand, had no inhibitory effect at the lowest dose used while it caused respective 25% (p<0.01) and 44% (p<0.01) inhibitions of estrone-stimulated uterine weight at the daily doses of 3 µg and 10 µg. The inactive enantiomer of lasofoxifene exerted no inhibitory effect on this parameter at any dose used.

The compounds mentioned above exerted similar effects on vaginal weight. The daily oral administration of EM-652.HCl led to respective 10% (NS), 25% and 53% inhibitions of vaginal weight (p<0.01 for the two highest doses) at the 1 µg, 3 µg, and 10 µg doses (FIG. 12), while raloxifene exerted a significant 24% (p<0.01) inhibitory effect on this parameter at the highest dose only (10 µg). Similarly to raloxifene, lasofoxifene (as free base) caused a significant 37% (p<0.01) inhibitory effect only at the highest dose used, while the inactive enantiomer had no inhibitory effect on vaginal weight at any dose used.

When compounds were administered alone (in the absence of estrone) to ovariectomized mice at the daily oral doses of 1 µg and 10 µg, EM-652.HCl had no significant stimulatory effect on uterine weight at both doses used, while treatment with 10 µg of lasofoxifene and raloxifene caused respective 93% (p<0.01) and 85% (p<0.01) stimulations of uterine weight (FIG. 13), thus indicating an estrogenic effect of these latter compounds on this parameter. Similarly, EM-652.HCl exerted no significant stimulatory effect on vaginal weight (FIG. 14) while administration of 10 µg of lasofoxifene and raloxifene caused respective 73% (p<0.01) and 56% (p<0.01) stimulations of vaginal weight. On the other hand, the inactive enantiomer of lasofoxifene had no stimulatory effect on uterine and vaginal weight.

Experiment 2

As shown in table 4, TSE 424 administered at the daily oral doses of 1 µg, 3 µg, 10 µg or 30 µg caused respective 12% (NS), 47%, 74%, and 94% inhibitions of estrone-stimulated uterine weight (p<0.01 for the three highest doses versus E$_1$-control). On the other hand, the daily oral administration of TSE 424 led to respective 16% (NS), 56% (p<0.01) and 93% (p<0.01) inhibitions of vaginal weight at the 3 µg, 10 µg, and 30 µg doses.

When the compound was administered alone (in the absence of estrone) to ovariectomized mice at the daily oral doses of 3 µg and 30 µg, TSE 424 had no significant stimulatory effect on uterine and vaginal weight at both doses used (Table 4).

TABLE 4

Effect on uterine and vaginal weight of increasing concentrations of TSE 424 administered orally for 9 days to ovariectomized mice simultaneously treated or not with estrone.

| TREATMENT | UTERINE WEIGHT (mg) | VAGINAL WEIGHT (mg) |
| --- | --- | --- |
| INTACT | 54.6 ± 12.5** | 37.9 ± 3.9** |
| OVX | 15.6 ± 1.3** | 13.9 ± 1.5** |
| OVX + E$_1$ | 118.3 ± 6.0 | 53.4 ± 2.8 |
| OVX + E$_1$ + TSE 424 1 µg | 105.5 ± 6.1 | 54.2 ± 3.0 |
| OVX + E$_1$ + TSE 424 3 µg | 69.7 ± 4.4** | 47.2 ± 1.6 |
| OVX + E$_1$ + TSE 424 10 µg | 42.1 ± 2.7** | 31.1 ± 2.3** |

TABLE 4-continued

Effect on uterine and vaginal weight of increasing concentrations of TSE 424 administered orally for 9 days to ovariectomized mice simultaneously treated or not with estrone.

| TREATMENT | UTERINE WEIGHT (mg) | VAGINAL WEIGHT (mg) |
|---|---|---|
| OVX + E$_1$ + TSE 424 30 µg | 21.7 ± 1.7** | 16.7 ± 1.8** |
| OVX + TSE 424 3 µg | 18.3 ± 1.2 | 14.1 ± 1.2 |
| OVX + TSE 424 30 µg | 17.7 ± 1.6 | 15.3 ± 2.0 |

**p < 0.01 versus E$_1$-treated control.

Example 4

Preventive Effects on Bone Loss, Serum Lipids and Total Body Fat

Animals and Treatment

Ten to twelve week-old female Sprague-Dawley rats (Crl:CD(SD)Br) (Charles River Laboratory, St-Constant, Canada) weighing approximately 220-270 g at start of treatment were used. The animals were acclimatized to the environmental conditions (temperature: 22±3° C.; humidity: 50±20%; 12-h light-12-h dark cycles, lights on at 07:15 h) for at least 1 week before starting the experiments. The animals were housed individually and were allowed free access to tap water and a pelleted certified rodent feed (Lab Diet 5002, Ralston Purina, St-Louis, Mo.). Experiments were conducted in an animal facility approved by the Canadian Council on Animal Care (CCAC) and the Association for Assessment and Accreditation of Laboratory Animal Care (AAALAC) in accordance with the CCAC Guide for Care and Use of Experimental Animals.

In a first experiment, one hundred fifty-four rats were randomly distributed between 11 groups of 14 animals each as follows: 1) Intact control; 2) OVX control; 3) OVX+E$_2$ (1 mg/kg); 4) OVX+EM-652.HCl (2.5 mg/kg); 5) OVX+E$_2$+EM-652.HCl; 6) OVX+dehydroepiandrosterone (DHEA; 80 mg/kg); 7) OVX+DHEA+EM-652.HCl; 8) OVX+DHEA+E$_2$; 9) OVX+DHEA+E$_2$+EM-652.HCl; 10) OVX+GW 5638; 11) OVX+E$_2$+GW 5638. On day 1 of the study, the animals of the appropriate groups were bilaterally ovariectomized (OVX) under isoflurane anesthesia. The DHEA was applied topically on the dorsal skin as a solution in 50% ethanol-50% propylene glycol while the other tested compounds were administered as suspension in 0.4% methylcellulose by oral gavage. Treatments were initiated on day 2 of the study and were performed once daily during 3 months.

In the second experiment, one hundred thirty-two rats were randomly distributed between 9 groups of 14 or 15 animals each as follows: 1) Intact control; 2) OVX control; 3) OVX+Premarin (0.25 mg/kg); 4) OVX+EM-652.HCl (2.5 mg/kg); 5) OVX+Premarin+EM-652.HCl; 6) OVX+TSE 424 (2.5 mg/kg); 7) OVX+Premarin+TSE 424; 8) OVX+Lasofoxifene (tartrate salt; racemate; 2.5 mg/kg); 9) OVX+Premarin+Lasofoxifene. On day 1 of the study, the animals of the appropriate groups were bilaterally OVX under isoflurane anesthesia. Tested compounds were administered as suspension in 0.4% methylcellulose by oral gavage. Treatments were initiated on day 2 of the study and were performed once daily during 26 weeks. In both experiments, animals not receiving a test article were treated with the appropriate vehicle alone during the same period.

Bone Mineral Density Measurements

After 3 months (experiment 1) or 26 weeks (experiment 2) of treatment, individual rats under Isoflurane anesthesia had their whole body skeleton and lumbar spine scanned using dual energy x-ray absorptiometry (DEXA; QDR 4500A, Hologic, Waltham, Mass.) and a Regional High Resolution Scan software. The bone mineral density (BMD) of the lumbar spine (vertebrae L2 to L4) and the total body composition (fat percentage) were determined.

Serum Assays

After 3 months (experiment 1) or 26 weeks (experiment 2) of treatment, blood samples were collected at the jugular vein from overnight fasted animals (under Isoflurane anesthesia). Samples were processed for serum preparation and frozen at −80° C. until assay. Serum cholesterol levels and alkaline phospatase activity (ALP) were determined using the Boehringer Mannheim Diagnostic Hitachi 911 Analyzer (Boehringer Mannheim Diagnostic Laboratory Systems).

Statistical Analyses

Data are expressed as means±SEM. Statistical significance was determined according to the multiple-range test of Duncan-Kramer (Kramer C Y; Biometrics 1956; 12:307-310).

Results

As shown in table 5, after 3 months of ovariectomy, BMD of the lumbar spine was 10% lower in OVX control animals than in intact controls (p<0.01). At the doses used, the administration of estradiol and EM-652.HCl alone prevented lumbar spine BMD loss by 98% (p<0.01) and 65% (p<0.05), respectively, while the combined treatment with E$_2$ and EM-652.HCl prevented the OVX-induced decrease in lumbar spine BMD by 61% (p<0.05). On the other hand, while the administration of DHEA alone prevented lumbar spine BMD by 43% (p<0.05), the combined treatment with DHEA+E$_2$+EM-652.HCl prevented the OVX-induced decrease in lumbar spine BMD by 91% and led to BMD value not different from intact controls.

In table 6, 26 weeks after ovariectomy, BMD of the lumbar spine was 18% lowered compared to intact controls (p<0.01). The administration of Premarin, EM-652.HCl, TSE 424 and Lasofoxifene alone prevented lumbar spine BMD by 54%, 62%, 49% and 61%, respectively (all p<0.01 versus OVX controls). The addition of Premarin to EM-652.HCl, TSE 424 or Lasofoxifene led to lumbar spine BMD values not significantly different from those obtained with the administration of each SERM alone (Table 6). Similarly, the addition of DHEA to E$_2$ or to EM-652.HCl completely prevented the OVX-induced decrease in lumbar spine BMD (Table 5). The positive effect of DHEA on BMD is also supported by its effect on serum alkaline phosphatase activity (ALP), a marker of bone formation and turnover. ALP activity was increased from 73±6 IU/L in OVX control animals to 224±18 IU/L, 290±27 IU/L, 123±8 IU/L and 261±20 IU/L (all p<0.01) in DHEA-, DHEA+EM-652.HCl-, DHEA+E$_2$- and DHEA+E$_2$+EM-652.HCl-treated animals, respectively, thus suggesting a stimulatory effect of DHEA on bone formation (Table 7).

In addition to the preventive effects on bone loss, the administration of EM-652.HCl, TSE 424, Lasofoxifene, GW 5638, DHEA and E$_2$ exerts some beneficial effects on total body fat percentage and serum lipids. After three months of ovariectomy, total body fat was increase by 22% (p<0.05; Table XXX 6). The administration of EM-652.HCl completely prevented the OVX-induced fat percentage increase while the addition of DHEA and/or E$_2$ to the SERM led to fat percentage values below those observed in intact control animals. After 26 weeks of ovariectomy, the 40% fat increase induced by estrogen deficiency was reversed by 74%, 78%, 75% and 114% following the administration of Premarin, EM-652.HCl, TSE 424 or Lasofoxifene, respectively, while the addition of Premarin to each SERM completely prevented the OVX-induced fat percentage increase (Table 8).

As shown in Table 7, three months after ovariectomy, a 22% increase in serum cholesterol levels was observed in OVX control rats compared to intact controls (p<0.01). In fact, serum cholesterol was increased from 2.01±0.11 mmol/L in intact animals to 2.46±0.08 mmol/L in OVX controls. The administration of $E_2$ or DHEA alone decrease serum cholesterol levels to 1.37±0.18 mmol/L and 1.59±0.10 mmol/L, respectively, while the administration of EM-652.HCl alone or in combination with $E_2$ and/or DHEA led to cholesterol levels significantly lower (between 0.65 to 0.96 mmol/L) than those found in intact animals (2.01±0.11 mmol/L). Similarly, the administration of GW 5638, TSE 424 and lasofoxifene alone or in combination with $E_2$ or Premarin completely prevented the OVX-induced increase on serum cholesterol levels and led to values lower than those found in intact animals (Tables 7 and 8).

TABLE 5

EFFECT ON PREVENTION OF BONE LOSS FOLLOWING 3 MONTH-TREATMENT WITH ESTRADIOL, EM-652•HCl, GW 5638 OR DHEA, ADMINISTERED ALONE OR IN COMBINATION, TO OVARIECTOMIZED FEMALE RATS

| ARTICLE II.<br>ARTICLE IV.<br>TREATMENT | ARTICLE III.<br>LUMBAR SPINE | |
|---|---|---|
| | BMD (g/cm$^2$) | Prevention of Bone Loss (%) |
| 1) Intact | 0.2461 ± 0.0049** | 100 |
| OVX | 0.2214 ± 0.0044 | — |
| OVX + $E_2$ | 0.2457 ± 0.0049** | 98 |
| OVX + EM-652•HCl | 0.2374 ± 0.0027* | 65 |
| OVX + EM-652•HCl + $E_2$ | 0.2364 ± 0.0037* | 61 |
| OVX + DHEA | 0.2321 ± 0.0034 | 43 |
| OVX + DHEA + EM-652•HCl | 0.2458 ± 0.0037** | 99 |
| OVX + DHEA + $E_2$ | 0.2496 ± 0.0029** | 114 |
| OVX + DHEA + $E_2$ + EM-652•HCl | 0.2439 ± 0.0043** | 91 |

TABLE 5-continued

EFFECT ON PREVENTION OF BONE LOSS FOLLOWING 3 MONTH-TREATMENT WITH ESTRADIOL, EM-652•HCl, GW 5638 OR DHEA, ADMINISTERED ALONE OR IN COMBINATION, TO OVARIECTOMIZED FEMALE RATS

| ARTICLE II.<br>ARTICLE IV.<br>TREATMENT | ARTICLE III.<br>LUMBAR SPINE | |
|---|---|---|
| | BMD (g/cm$^2$) | Prevention of Bone Loss (%) |
| OVX + GW 5638 | 0.2299 ± 0.0060 | 34 |
| OVX + GW 5638 + $E_2$ | 0.2344 ± 0.0054 | 53 |

*p < 0.05;
**p < 0.01, experimental versus OVX control rats.

TABLE 6

EFFECT ON PREVENTION OF BONE LOSS FOLLOWING 26 WEEK-TREATMENT WITH PREMARIN, EM-652•HCl, TSE 424 OR LASOFOXIFENE, ADMINISTERED ALONE OR IN COMBINATION WITH PREMARIN, TO OVARIECTOMIZED FEMALE RATS

| ARTICLE V.<br>ARTICLE VII.<br>TREATMENT | ARTICLE VI.<br>LUMBAR SPINE | |
|---|---|---|
| | BMD (g/cm$^2$) | Prevention of Bone Loss (%) |
| 1) Intact | 0.2482 ± 0.0067** | 100 |
| OVX | 0.2035 ± 0.0035 | — |
| OVX + Premarin | 0.2277 ± 0.0028** | 54 |
| OVX + EM-652•HCl | 0.2311 ± 0.0040** | 62 |
| OVX + Premarin + EM-652•HCl | 0.2319 ± 0.0057** | 64 |
| OVX + TSE 424 | 0.2252 ± 0.0058** | 49 |
| OVX + Premarin + TSE 424 | 0.2223 ± 0.0046** | 42 |
| OVX + Lasofoxifene | 0.2307 ± 0.0040** | 61 |
| OVX + Premarin + Lasofoxifene | 0.2357 ± 0.0035** | 72 |

**p < 0.01, experimental versus OVX control rats.

TABLE 7

EFFECT ON TOTAL BODY FAT PERCENTAGE, SERUM CHOLESTEROL LEVELS AND ALKALINE PHOSPHATASE ACTIVITY FOLLOWING 3 MONTH-TREATMENT WITH ESTRADIOL, EM-652•HCl, GW 5638 OR DHEA, ADMINISTERED ALONE OR IN COMBINATION, TO OVARIECTOMIZED FEMALE RATS

| ARTICLE VIII.<br>ARTICLE XII.<br>TREATMENT | ARTICLE IX.<br>TOTAL FAT (%) | ARTICLE X.<br>CHOLESTEROL (mmol/L) | ARTICLE XI.<br>ALP (IU/L) |
|---|---|---|---|
| 1) Intact | 24.0 ± 1.5* | 2.01 ± 0.11** | 39 ± 2** |
| OVX | 29.2 ± 1.5 | 2.46 ± 0.08 | 73 ± 6 |
| OVX + $E_2$ | 19.5 ± 2.5** | 1.37 ± 0.18** | 59 ± 4 |
| OVX + EM-652•HCl | 23.2 ± 1.4** | 0.87 ± 0.04** | 91 ± 6* |
| OVX + EM-652•HCl + $E_2$ | 20.4 ± 1.4** | 0.96 ± 0.07** | 92 ± 5* |
| OVX + DHEA | 17.3 ± 1.5** | 1.59 ± 0.10** | 224 ± 18** |
| OVX + DHEA + EM-652•HCl | 18.0 ± 1.1** | 0.65 ± 0.06** | 290 ± 27** |
| OVX + DHEA + $E_2$ | 15.8 ± 1.3** | 1.08 ± 0.08** | 123 ± 8** |
| OVX + DHEA + $E_2$ + EM-652•HCl | 19.2 ± 1.6** | 0.71 ± 0.08** | 261 ± 20** |
| OVX + GW 5638 | 21.9 ± 1.4** | 1.14 ± 0.08** | 72 ± 6 |
| OVX + GW 5638 + $E_2$ | 23.2 ± 1.2** | 0.91 ± 0.07** | 80 ± 6 |

*p < 0.05;
**p < 0.01, experimental versus OVX control rats.

TABLE 8

EFFECT ON TOTAL BODY FAT PERCENTAGE, SERUM CHOLESTEROL LEVELS AND ALKALINE PHOSPHATASE ACTIVITY FOLLOWING 26 WEEK-TREATMENT WITH PREMARIN, EM-652•HCl, TSE 424 OR LASOFOXIFENE, ADMINISTERED ALONE OR IN COMBINATION WITH PREMARIN, TO OVARIECTOMIZED FEMALE RATS

| ARTICLE XIII. ARTICLE XVII. TREATMENT | ARTICLE XIV. TOTAL FAT (%) | ARTICLE XV. CHOLESTEROL (mmol/L) | ARTICLE XVI. ALP (IU) |
|---|---|---|---|
| 1) Intact | 25.5 ± 1.8** | 2.11 ± 0.11** | 33 ± 2* |
| OVX | 35.7 ± 1.6 | 2.51 ± 0.09 | 60 ± 6 |
| OVX + Premarin | 28.2 ± 1.8** | 1.22 ± 0.07** | 49 ± 3 |
| OVX + EM-652•HCl | 27.7 ± 1.4** | 0.98 ± 0.06** | 78 ± 4 |
| OVX + EM-652•HCl + Premarin | 25.7 ± 2.2** | 1.10 ± 0.07** | 81 ± 6 |
| OVX + TSE 424 | 28.0 ± 1.8** | 1.15 ± 0.05** | 85 ± 6 |
| OVX + TSE 424 + Premarin | 25.7 ± 1.7** | 1.26 ± 0.14** | 98 ± 22** |
| OVX + Lasofoxifene | 24.1 ± 1.3** | 0.60 ± 0.02** | 116 ± 9** |
| OVX + Lasofoxifene + Premarin | 23.8 ± 1.9** | 0.81 ± 0.12** | 107 ± 6** |

*$p < 0.05$;
**$p < 0.01$, experimental versus OVX control rats.

Example 5

Preventive Effects on Bone Loss Following Treatment with the SERMs EM-652.HCl, TSE-424 and Era-923, Administered Alone and in Combination with DHEA to Ovariectomized Female Rats Animals and Treatment Ten to twelve week-old female Sprague-Dawley rats (Crl:CD(SD)Br) (Charles River Laboratory, St-Constant, Canada) weighing approximately 220-270 g at start of treatment were used. The animals were acclimatized to the environmental conditions (temperature: 22±3° C.; humidity: 50±20%; 12-h light-12-h dark cycles, lights on at 07:15 h) for at least 1 week before starting the experiments. The animals were housed individually and were allowed free access to tap water and a pelleted certified rodent feed (Lab Diet 5002, Ralston Purina, St-Louis, Mo.). Experiments were conducted in an animal facility approved by the Canadian Council on Animal Care (CCAC) and the Association for Assessment and Accreditation of Laboratory Animal Care (AAALAC) in accordance with the CCAC Guide for Care and Use of Experimental Animals.

One hundred twenty-six rats were randomly distributed between 9 groups of 14 animals each as follows: 1) Intact control; 2) OVX control; 3) OVX+EM-652.HCl (2.5 mg/kg); 4) OVX+TSE-424 (EM-4803, 2.5 mg/kg); 5) OVX+ERA-923 (EM-3527, 2.5 mg/kg); 6) OVX+dehydroepiandrosterone (DHEA; 80 mg/kg); 7) OVX+DHEA+EM-652.HCl; 8) OVX+DHEA+TSE-424; 9) OVX+DHEA+ERA-923. On day 1 of the study, the animals of the appropriate groups were bilaterally ovariectomized (Ovx) under isoflurane anesthesia. The DHEA was applied topically on the dorsal skin as a solution in 50% ethanol-50% propylene glycol while the tested SERMs were administered as suspension in 0.4% methylcellulose by oral gavage. Treatments were initiated on day 2 of the study and were performed once daily during 5 weeks.

Bone Mineral Density Measurements

After 5 weeks of treatment, individual rats under Isoflurane anesthesia had their lumbar spine, femur and tibia scanned using dual energy x-ray absorptiometry (DEXA; QDR 4500A, Hologic, Waltham, Mass.) and a Regional High Resolution Scan software. The bone mineral density (BMD) of the lumbar spine (vertebrae L2 to L4), distal femoral metaphysis (DFM) and proximal tibial metaphysis (PTM) were determined.

Statistical Analyses

Data are expressed as means±SEM. Statistical significance was determined according to the multiple-range test of Duncan-Kramer (Kramer C Y 1956).

Results

As shown in table 9, after 5 weeks of ovariectomy, BMD of the lumbar spine was 9% lower in Ovx control animals than in intact controls. At the dose used the administration of the SERMs: EM-652.HCl, TSE-424 or ERA-923 alone prevented lumbar spine BMD loss by 86%, 53% and 78%, respectively. On the other hand, the administration of DHEA alone prevented lumbar spine BMD loss by 44%, while the combined treatment with DHEA+EM-652.HCl, DHEA+TSE-424 or DHEA+ERA-923 prevented the OVX-induced decrease in lumbar spine BMD by 94%, 105% and 105%, respectively.

Bone mineral density of the distal femoral metaphysis (DFM) was decreased by 10% after 5 weeks of ovariectomy (Table 9). The administration of the SERMs: EM-652.HCl, TSE-424 or ERA-923 alone prevented DFM BMD loss by 95%, 70% and 83%, respectively. On the other hand, the administration of DHEA alone prevented DFM BMD loss by 71%, while the combined treatment with DHEA+EM-652.HCl, DHEA+TSE-424 or DHEA+ERA-923 completely prevented the OVX-induced decrease in DFM BMD and led to DFM BMD values higher than those observed in intact control animals. Similar results were obtained on proximal tibial metaphysis BMD (Table 9).

TABLE 9

EFFECT ON PREVENTION OF BONE LOSS FOLLOWING 5 WEEK-TREATMENT WITH THE SERMs EM-652•HCl, TSE-424 AND ERA-923, ADMINISTERED ALONE OR IN COMBINATION WITH DHEA, TO OVARIECTOMIZED FEMALE RATS

| TREATMENT | LUMBAR SPINE (L2-L4) | | DISTAL FEMORAL METAPHYSIS (DFM) | | PROXIMAL TIBIAL METAPHYSIS (PFM) | |
|---|---|---|---|---|---|---|
| | BMD (g/cm$^2$) | Prevention of Bone Loss (%) | BMD (g/cm$^2$) | Prevention of Bone Loss (%) | BMD (g/cm$^2$) | Prevention of Bone Loss (%) |
| Intact | 0.2261 ± 0.0046 | 100 | 0.3024 ± 0.0040 | 100 | 0.2828 ± 0.0032 | 100 |
| Ovx | 0.2051 ± 0.0037 | — | 0.2709 ± 0.0036 | — | 0.2560 ± 0.0028 | — |
| Ovx + EM-652•HCl | 0.2232 ± 0.0031 | 86 | 0.3008 ± 0.0055 | 95 | 0.2806 ± 0.0035 | 92 |
| Ovx + TSE-424 | 0.2162 ± 0.0035 | 53 | 0.2929 ± 0.0042 | 70 | 0.2750 ± 0.0039 | 71 |
| Ovx + ERA-923 | 0.2214 ± 0.0029 | 78 | 0.2969 ± 0.0029 | 83 | 0.2805 ± 0.0034 | 91 |
| Ovx + DHEA | 0.2144 ± 0.0028 | 44 | 0.2934 ± 0.0046 | 71 | 0.2672 ± 0.0041 | 42 |
| Ovx + DHEA + EM-652•HCl | 0.2249 ± 0.0023 | 94 | 0.3122 ± 0.0045 | 131 | 0.2867 ± 0.0047 | 115 |
| Ovx + DHEA + TSE-424 | 0.2271 ± 0.0030 | 105 | 0.3099 ± 0.0040 | 124 | 0.2833 ± 0.0034 | 102 |
| Ovx + DHEA + ERA-923 | 0.2271 ± 0.0030 | 105 | 0.3072 ± 0.0053 | 115 | 0.2817 ± 0.0034 | 96 |

Example 6

Effect of Compounds of the Invention on Alkaline Phosphatase Activity in Human Endometrial Adenocarcinoma Ishikawa Cells.

Materials

Maintenance of Stock Cell Cultures

The human Ishikawa cell line derived from a well differentiated endometrial adenocarcinoma was kindly provided by Dr. Erlio Gurpide, The Mount Sinai Medical Center, New York, N.Y. The Ishikawa cells were routinely maintained in Eagle's Minimum Essential Medium (MEM) containing 5% (vol/vol) FBS (Fetal Bovine Serum) and supplemented with 100 U/ml penicillin, 100 µg/ml streptomycin, 0.1 mM non-essential amino acids solution. Cells were plated in Falcon T75 flasks at a density of 1.5×10$^6$ cells at 37° C.

Cell Culture Experiments

Twenty four hours before the start of the experiment, the medium of near confluent Ishikawa cells was replaced by fresh estrogen-free basal medium (EFBM) consisting of a 1:1 (v:v) mixture of phenol red-free Ham's F-12 and Dulbecco's Modified Eagle's Medium (DMEM) supplemented with 100 U/mL penicillin, 100 µg/mL streptomycin, 2 mM glutamine, and 5% FBS treated twice with dextran-coated charcoal to remove endogenous steroids. Cells were then harvested by 0.1% pancreatin (Sigma) and 0.25 mM HEPES, resuspended in EFBM and plated in Falcon 96, well flat-bottomed microtiter plates at a density of 2.2×10$^4$ cells/well in a volume of 100 µl and allowed to adhere to the surface of the plates for 24 h. Thereafter, medium was replaced with fresh EFBM containing the indicated concentrations of compounds in a final volume of 200 µl. Cells were incubated for five days, with a medium change after 48 h.

Alkaline Phosphatase Assay

At the end of the incubation period, microtiter plates were inverted and growth medium was decanted. The plates were rinsed with 200 µl by well of PBS (0.15M NaCl, 10 mM sodium phosphate, pH 7.4). PBS was then removed from the plates while carefully leaving some residual PBS, and the wash procedure was repeated once. The buffered saline was then decanted, and the inverted plates were blotted gently on a paper towel. Following replacement of the covers, the plates were placed at −80° C. for 15 min followed by thawing at room temperature for 10 min. The plates were then placed on ice, and 50 µl of an ice-cold solution containing 5 mM p-nitrophenyl phosphate, 0.24 mM MgCl$_2$, and 1 M diethanolamine (pH 9.8) were added. Plates were then warmed to room temperature, and the yellow color from the production of p-nitrophenyl was allowed to develop (8 min). Plates were monitored at 405 nm in an enzyme-linked immunosorbent assay plate reader (BIO-RAD, model 2550 EIA Reader).

Calculations

Dose-response curves as well as IC$_{50}$ values were calculated using a weighted iterative nonlinear squares regression.

TABLE 10

| NAME | CODE NAME | STRUCTURE | Maximal stimulation of alkaline phosphatase % of 1 nM E$_2$ stimulation* (nb of experiments) | Inhibition of 1 nM E$_2$-induced stimulation of alkaline phosphatase IC$_{50}$ (nM) (nb of experiments) | Maximal inhibition of 1 nM E$_2$-induced stimulation of alkaline phosphatase (nb of experiments) |
|---|---|---|---|---|---|
| EM-652•HCl (Acolbifene) | EM-652•HCl; (EM-1538) | 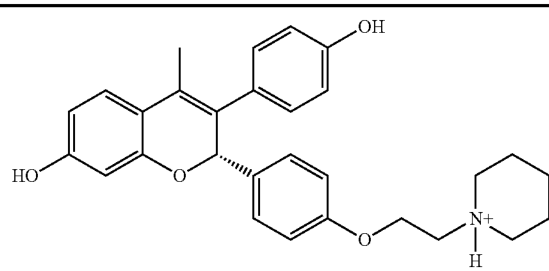 | 1.88 ± 0.26 (22) | 1.52 ± 0.22 (18) | 98.97 ± 0.174 (18) |

TABLE 10-continued

| NAME | CODE NAME | STRUCTURE | Maximal stimulation of alkaline phosphatase % of 1 nM $E_2$ stimulation* (nb of experiments) | Inhibition of 1 nM $E_2$-induced stimulation of alkaline phosphatase $IC_{50}$ (nM) (nb of experiments) | Maximal inhibition of 1 nM $E_2$-induced stimulation of alkaline phosphatase (nb of experiments) |
|---|---|---|---|---|---|
| OH-Toremifene | EM-880 | 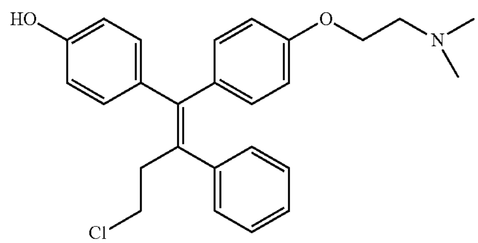 [SMILES: CN(C)CCOc1ccc(/C(=C(/CCCl)c2ccccc2)c2ccc(O)cc2)cc1] | 29.6 ± 2.1 (6) | 72.1 ± 7.6 (3) | 75.73 ± 3.52 (3) |
| GW-5638 | EM-1796 | 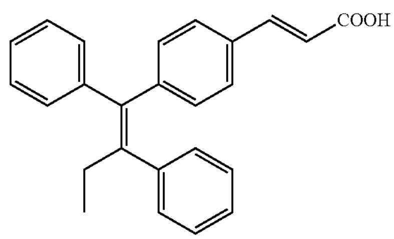 [SMILES: CC/C(=C(\c1ccccc1)c1ccc(/C=C/C(=O)O)cc1)c1ccccc1] | 7.75 ± 5.5 (2) | No inhibition | |
| Raloxifene LY 156758 | EM-1105 | 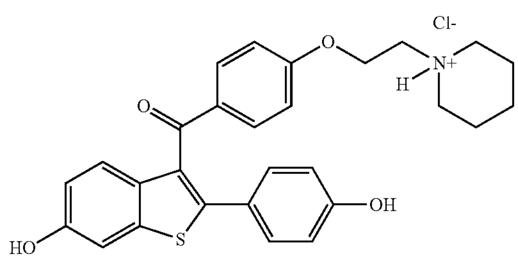 [SMILES: [Cl-] ; O=C(c1ccc(OCC[NH+]2CCCCC2)cc1)c1c(-c2ccc(O)cc2)sc2cc(O)ccc12] | 12.8 ± 1.7 (8) | 3.39 ± 0.9 (6) | 94.31 ± 1.74 (5) |
| LY 353381 | EM-1665 | 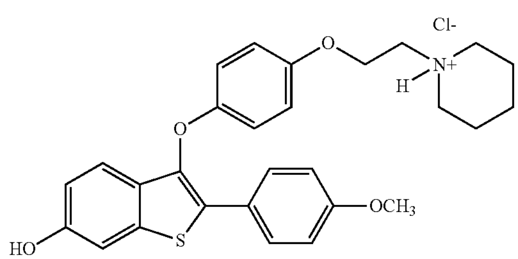 [SMILES: [Cl-] ; COc1ccc(-c2sc3cc(O)ccc3c2Oc2ccc(OCC[NH+]3CCCCC3)cc2)cc1] | 15.5 ± 0.25 (5) | 1.87 ± 0.07 (2) | 90.25 ± 0.127 (2) |
| Lasofoxifene (free base) | EM-3114 | 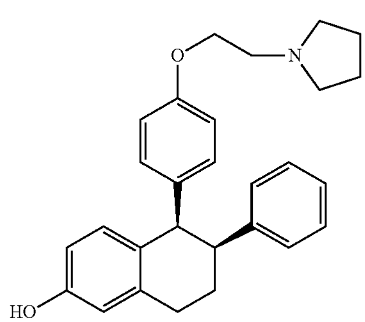 [SMILES: Oc1ccc2c(c1)CC[C@H](c1ccccc1)[C@@H]2c1ccc(OCCN2CCCC2)cc1] | 17.9 (1) | 4.24 (1) | 85.14 (1) |

TABLE 10-continued

| NAME | CODE NAME | STRUCTURE | Maximal stimulation of alkaline phosphatase % of 1 nM $E_2$ stimulation* (nb of experiments) | Inhibition of 1 nM $E_2$-induced stimulation of alkaline phosphatase $IC_{50}$ (nM) (nb of experiments) | Maximal inhibition of 1 nM $E_2$-induced stimulation of alkaline phosphatase (nb of experiments) |
|---|---|---|---|---|---|
| ERA-923 | EM-3527 | 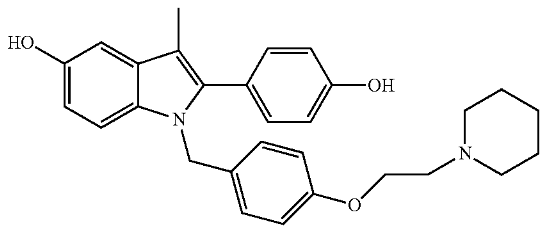 [SMILES: Cc1c(-c2ccc(O)cc2)n(Cc2ccc(OCCN3CCCCC3)cc2)c2ccc(O)cc12] | 0.6 (1) | 5.84 (1) | 100.16 (1) |

*% of 1 nM $E_2$ stimulation =
OD 405 nm compound-OD 405 nm basal/OD 405 nm 1 nM $E_2$-OD 405 nm basal
Please see also Labrie et al. 1999.

Example 7

Effect of EM-652.HCl, TSE 424, and Lasofoxifene on the Proliferation of Human Breast Cancer MCF-7 Cells Methods:

Maintenance of Stock Cell Cultures

MCF-7 human breast cancer cells were obtained from the American Type Culture Collection #HTB 22 at passage 147 and routinely grown in phenol red-free Dulbecco's Modified Eagle's-Ham's F12 medium, the supplements mentioned above and 5% FBS. The MCF-7 human breast adenocarcinoma cell line was derived from the pleural effusion of a Caucasian 69-year-old female patient. MCF-7 cells were used between passages 148 and 165 and subcultured weekly Cell Proliferation Studies Cells in their late logarithmic growth phase were harvested with 0.1% pancreatin (Sigma) and resuspended in the appropriate medium containing 50 ng bovine insulin/ml and 5% (v/v) FBS treated twice with dextran-coated charcoal to remove endogenous steroids. Cells were plated in 24-well Falcon plastic culture plates (2 cm²/well) at the indicated density and allowed to adhere to the surface of the plates for 72 h. Thereafter, medium was replaced with fresh medium containing the indicated concentrations of compounds diluted from 1000× stock solutions in 99% redistilled ethanol in the presence or absence of $E_2$. Control cells received only the ethanolic vehicle (0.1% EtOH, v/v). Cells were incubated for the specified time intervals with medium changes at 2- or 3-day intervals. Cell number was determined by measurement of DNA content.

Calculations and Statistical Analysis

Dose-response curves as well $IC_{50}$ values were calculated using a weighted iterative nonlinear least-squares regression. All results are expressed as means±SEM.

TABLE 11

| | | Experiment 1 | |
|---|---|---|---|
| NAME | CODE NAME | Maximal stimulation of DNA by tested compounds % of 1 nM $E_2$ stimulation * | Inhibition of 1 nM $E_2$ stimulation of DNA by tested compounds $IC_{50}$ (nM) |
| EM-652•HCl | EM-652•HCl; EM-1538 | N.S. | 0.796 |
| TSE 424 | EM-3527 | N.S. | 3.68 |
| | | Experiment 2 | |
| NAME | CODE NAME | Stimulation of DNA by tested compounds % of 1 nM $E_2$ stimulation * | Inhibition of 1 nM $E_2$ stimulation of DNA by tested compounds $IC_{50}$ (nM) |
| EM-652•HCl | EM-652•HCl; EM-1538 | N.S. | 0.205 |
| Lasofoxifene (free base) | EM-3114 | N.S. | 0.379 |

Example 8

Comparison of the Effects of EM-652.HCl, Tamoxifen, Toremifene, Droloxifene, Idoxifene, GW-5638, and Raloxifene on the Growth of Human Rz-75-1 Breast Tumors in Nude Mice.

The objective of this example was to compare the agonistic and antagonistic effects of EM-652.HCl and six other oral antiestrogens (SERMs) on the growth of the well-characterized estrogen-sensitive ZR-75-1 breast cancer xenografts in ovariectomized nude mice.

Materials and Methods

Human ZR-75-1 Breast Cancer Cells

ZR-75-1 human breast cancer cells were obtained from the American Type Culture Collection (Rockville, Md.) and cultured in phenol red-free RPMI-1640 medium. The cells were supplemented with 2 mM L-glutamine, 1 mM sodium pyruvate, 100 IU penicillin/ml, 100 µg streptomycin/ml, and 10% (v/v) fetal bovine serum and incubated under an humidified atmosphere of 95% air/5% $CO_2$ at 37° C. Cells were passaged weekly and harvested at 85-90% confluence using 0.083% pancreatin/0.3 mM EDTA.

Animals and Tumor Inoculation

Homozygous female nu/nu Br athymic mice (28- to 42-day old) were obtained from Charles River, Inc. (Saint-Constant, Québec, Canada). The mice (5 per cage) were housed in vinyl cages equipped with air filter lids, which were kept in laminar airflow hoods and maintained under pathogen-limiting conditions. The photoperiod was 12 hours of light and 12 hours of darkness (lights on at 07:15). Cages, bedding and food (Agway Pro-Lab R-M-H Diet #4018) were autoclaved before use. Water was autoclaved and provided ad libitum. Bilateral ovariectomy was performed under isoflurane-induced anesthesia. At the time of ovariectomy, an implant of estradiol ($E_2$) was inserted subcutaneously to stimulate initial tumor growth. $E_2$ implants were prepared in 1 cm-long Silastic tubing (inside diameter: 0.062 inch; outside diameter: 0.095 inch) containing 0.5 cm of a 1:10 (w/w) mixture of estradiol and cholesterol. One week after ovariectomy, 2×10 6 ZR-75-1 (passage 93) cells were inoculated subcutaneously in 0.1 ml of RPMI-1640 medium+30% Matrigel on both flanks of each ovariectomized (OVX) mouse through a 2.5-cm-long 22-gauge needle. After four weeks, the $E_2$ implants were replaced in all animals by estrone-containing implants of the same size (E1:chol, 1:25, w:w). Randomization and treatments were started one week later.

Treatments

One day prior to initiation of treatments, 255 mice bearing ZR-75-1 tumors of an average area of 24.4±0.4 mm2 (range 5.7 to 50.7 mm$^2$) were randomly assigned to 17 groups (with respect to tumor size), each containing 15 mice (total of 29 or 30 tumors). The 17 groups included two control groups (OVX and OVX+Estrone), seven groups supplemented with an estrone implant and treated with an antiestrogen and eight other groups that received an antiestrogen alone. The estrone implants were then removed from the animals in the ovariectomized control group (OVX) and in groups that were to receive the antiestrogen alone. Estrone-containing implants in the nine other groups were changed thereafter every 6 weeks. EM-652.HCl, raloxifene, droloxifene, idoxifene and GW 5638 were synthesized in the medicinal chemistry division of the Oncology and Molecular Endocrinology Research Center. Tamoxifen was purchased from Plantex (Netanya, Israel) while toremifene citrate was purchased from Orion (Espoo, Finland). Under estrone stimulation, the antiestrogens were given at the daily oral dose of 50 μg (2 mg/kg, on average) suspended in 0.2 ml of 0.4% (w/v) methylcellulose. In the absence of estrone stimulation, animals were treated with 200 μg (8 mg/kg on average) of each antiestrogen once daily by the oral route. Animals in both control groups received 0.2 ml of the vehicle alone. The antiestrogen suspensions at the appropriate concentration were prepared each month, stored at 4° C. and used under constant agitation. Powder stock were hermetically stored at 4° C. (idoxifene, raloxifene, toremifene, GW 5638, droloxifene) or at room temperature (tamoxifen, EM-652.HCl).

Tumor Measurements and Necropsy

Two perpendicular diameters were recorded and tumor area (mm2) was calculated using the formula: L/2×W/2×π. The area measured on the first day of treatment was taken as 100%.

After 161 days of treatment, the remaining animals were anesthetized with isoflurane and killed by exsanguination. To further characterize the effect of the estrogen and antiestrogens, estrogen-responsive tissues, such as the uterus and vagina, were immediately removed, freed from connective and adipose tissue and weighed. The uteri were prepared to evaluate endometrial thickness by image analysis performed with Image Pro-Plus (Media Cybernetics, Maryland, USA). In brief, uteri were fixed in 10% formalin and embedded in parafin. Hematoxylin- and eosin-stained sections of mice uteri were analyzed. Four images per uterus (2 per uterine horn) were analyzed. Mean epithelial cell height was measured in all animals of each group.

Response Criteria

Tumor response was assessed at the end of the study or at death of each animal, if it occurred during the course of the experiment. In this case, only data of mice that survived for at least half of the study (84 days) were used in the tumor response analysis. In brief, complete regression identifies those tumors that were undetectable at the end of the experiment; partial regression corresponds to the tumors that regressed ≥50% of their original size; stable response refers to tumors that regressed <50% or progressed 50%; and progression refers to tumors that progressed ≥50% compared with their original size.

Statistical Analyses

The change in total tumors surface areas between day 1 and day 161 were analyzed according to an ANOVA for repeated measurements. The model included the treatment, time, and time-treatment interaction effects plus the term to account for the strata at randomization. The significance of the different treatments effects at 161 days was thus tested by the time-treatment interaction. Analysis of the residuals indicated that the measurements on the original scale were not fitted for analysis by an ANOVA nor any of the transformations that were tried. The ranks were therefore selected for the analyses. The effect of the treatments on the epithelial thickness was assessed by a one-way ANOVA including also the strata at randomization. A posteriori pairwise comparisons were performed using least square means statistics. The overall type 1 error rate (a) was controlled at 5% to declare significance of the differences. All calculations were performed using Proc MIXED on the SAS Software (SAS Institute, Carry, N.C.).

Results

Antagonistic Effects on ZR-75-1 Tumor Growth

Figure 18:
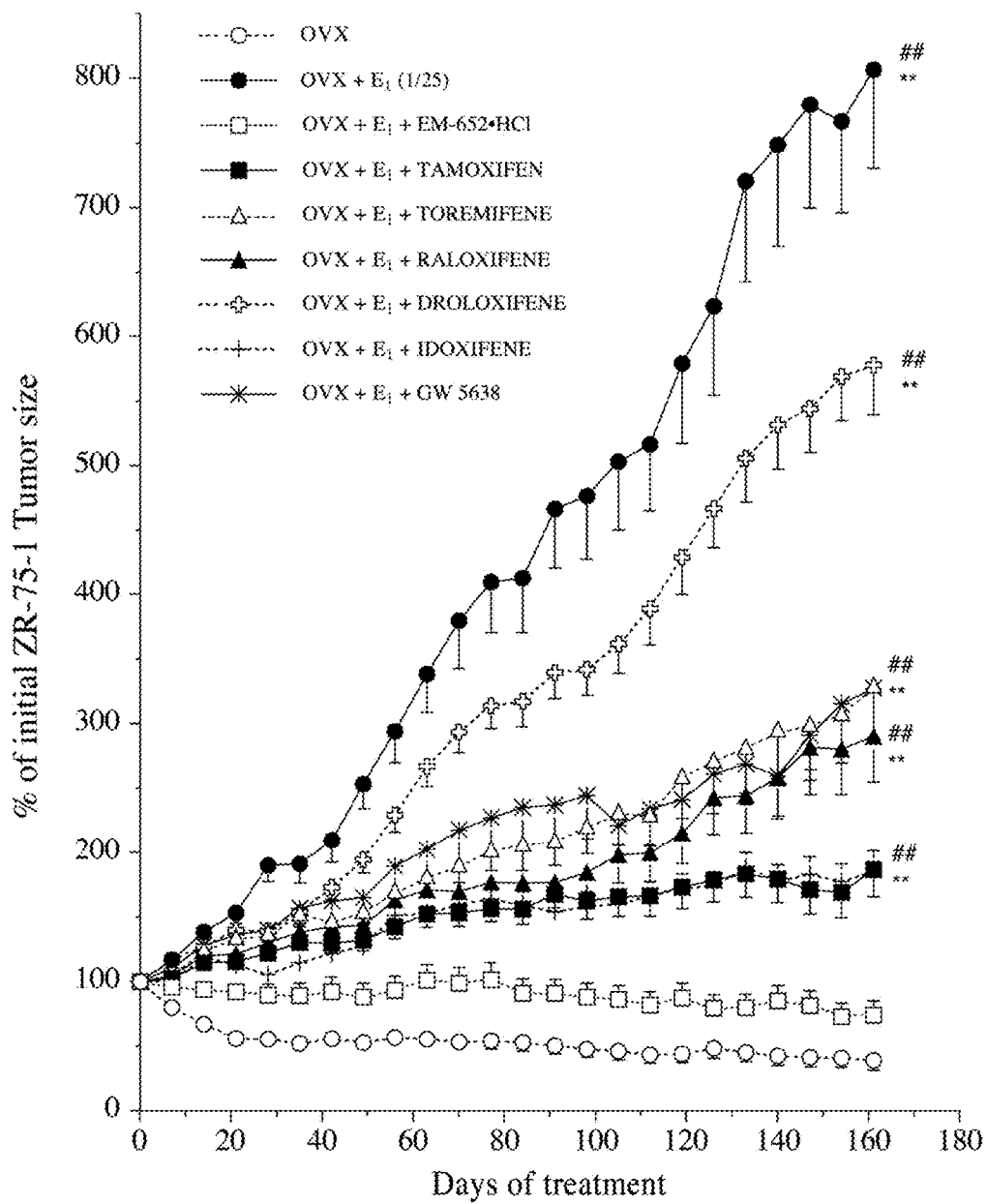
FIG. 18 shows the effects of antiestrogens on ZR-75-1 tumor growth. Effect of treatment with 7 antiestrogens for 161 days, on estrone-induced growth of human ZR-75-1 breast tumors in ovariectomized nude mice. Tumor size is expressed as the percentage of initial tumor area (Day1=100%). Data is expressed as means±SEM (n=18-30 tumors/group); ## p<0.01 vs EM-652.HCl; ** p<0.01 vs OVX. Antiestrogens were administered orally once daily at the dose of 50 μg/mouse under estrone stimulation obtained with subcutaneous 0.5-cm silastic implants containing 1:25 ratio of estrone and cholesterol.

Estrone alone (OVX+$E_1$) caused a 707% increase in ZR-75-1 tumor size during the 23 week-treatment period (FIG. 18). Administration of the pure antiestrogen EM-652.HCl at the daily oral dose of 50 μg to estrone-stimulated mice completely prevented tumor growth. In fact, not only tumor growth was prevented but after 23 weeks of treatment, tumor size was 26% lower than the initial value at start of treatment (p<0.04). This value obtained after treatment with EM-652.HCl was not statistically different from that observed after ovariectomy alone (OVX) where tumor size decreased by 61% below initial tumor size. At the same dose (50 μg) and treatment period, the six other antiestrogens did not decrease initial average tumor size. Tumors in these groups were all significantly higher than the OVX control group and to the EM-652.HCl-treated group (p<0.01). In fact, compared to pretreatment values, 23 weeks of treatment with droloxifene, toremifene, GW 5638, raloxifene, tamoxifen and idoxifene led to average tumor sizes 478%, 230%, 227%, 191%, 87% and 86% above pretreatment values, respectively (FIG. 18).

Agonistic Effects on ZR-75-1 Tumor Growth

Figure 19:
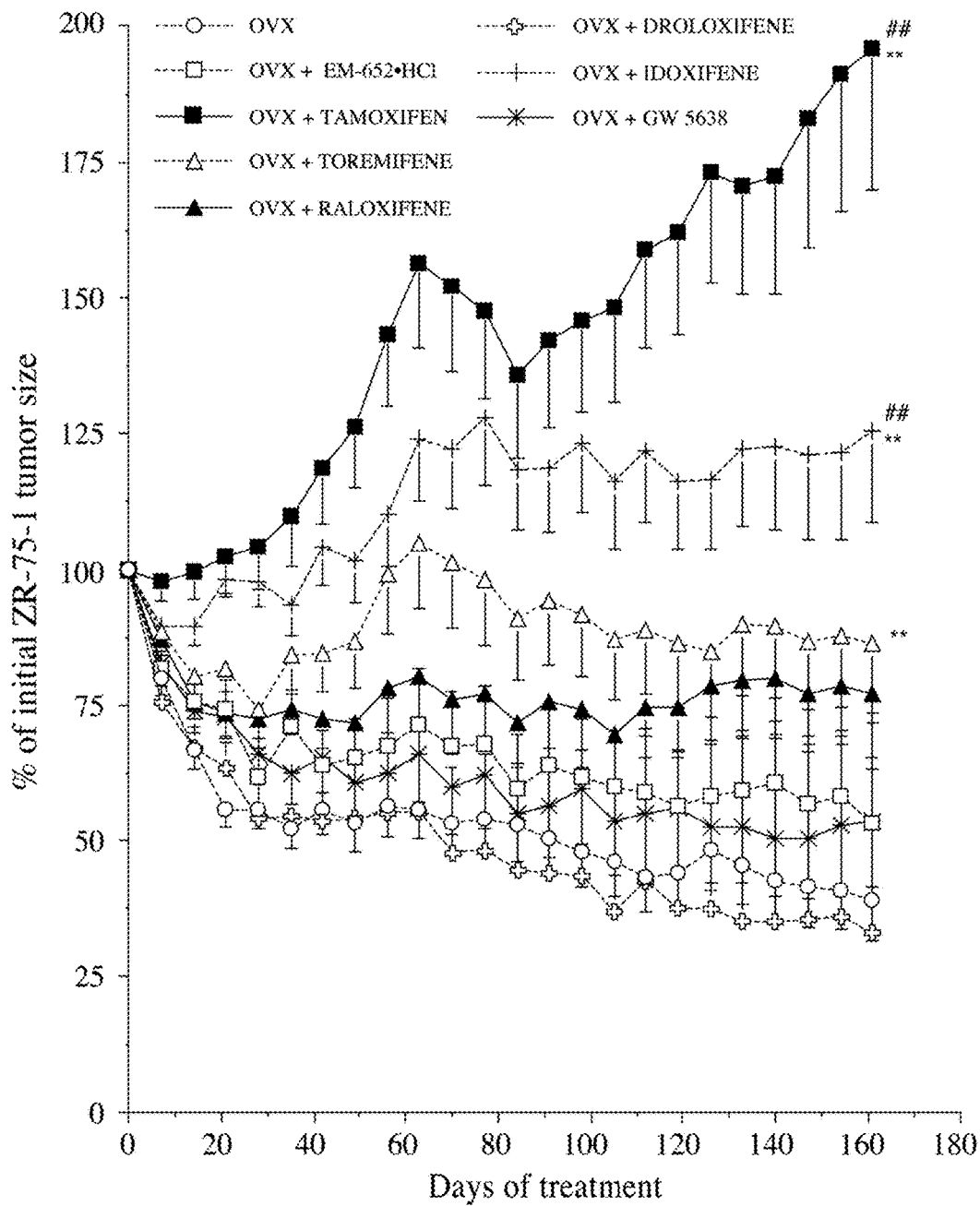
FIG. 19 shows the effects of antiestrogens on ZR-75-1 tumor growth. Effect of treatment with 7 antiestrogens for 161 days, on the growth of human ZR-75-1 breast tumors in ovariectomized nude mice. Tumor size is expressed as the percentage of initial tumor area (Day 1=100%). Date is expressed as means±SEM (n=18-30 tumors/group); ## $p<0.01$ vs EM-652.HCl; ** $p<0.01$ vs OVX. Antiestrogens were administered orally once daily at the dose of 100 µg/mouse in absence of estrogen stimulation.

After 161 days of treatment with a daily dose of 200 μg of tamoxifen, in the absence of estrone supplementation, the average tumor size increased to 196% over baseline (p<0.01 vs OVX) (FIG. 19). On the other hand, the average tumor size of mice treated with Idoxifene increased (125%)

Figure 20:
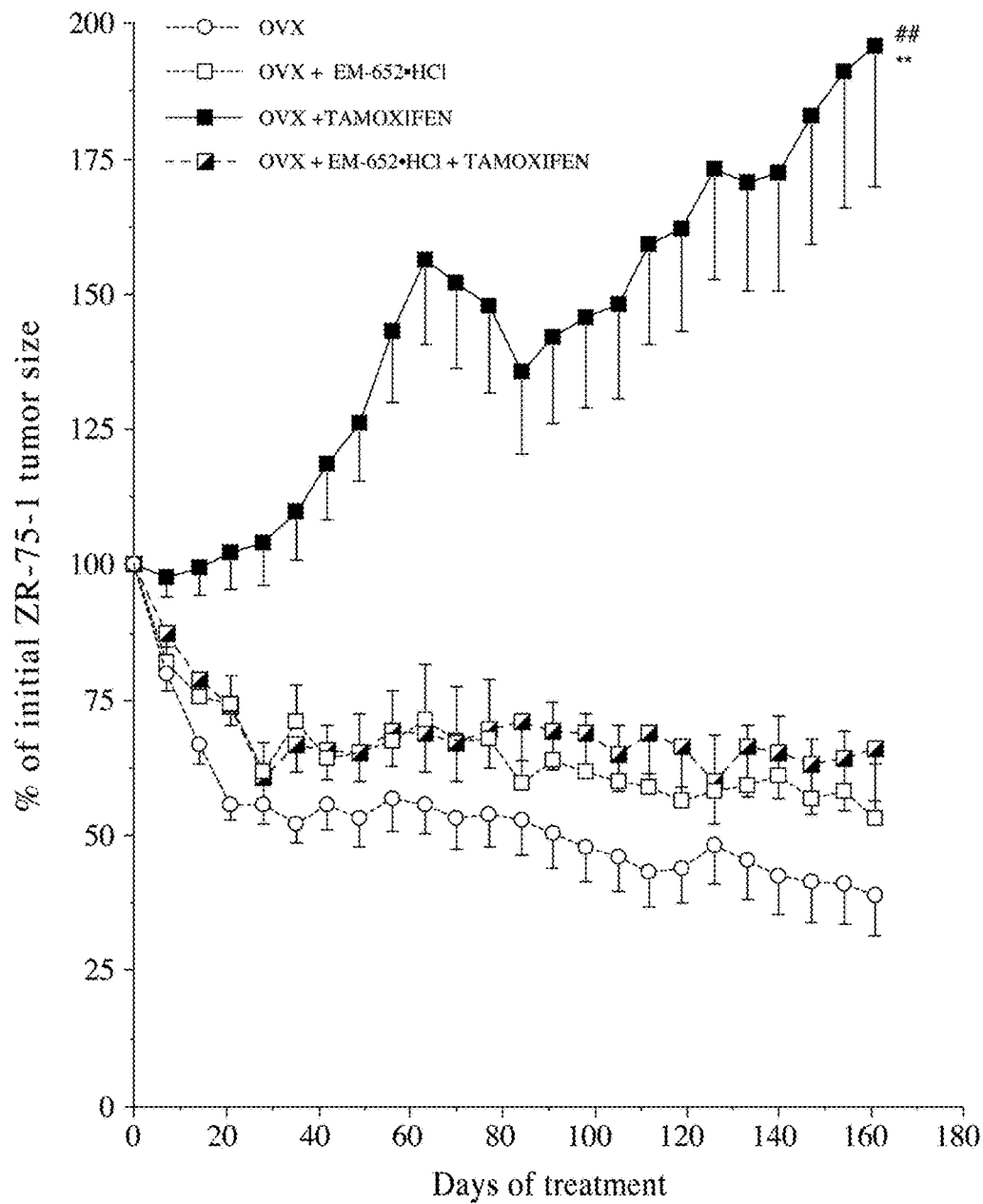
FIG. 20 shows the effects of antiestrogens on ZR-75-1 tumor growth. Effect of treatment with the antiestrogens Tamoxifen, EM-652.HCl (Acolbifene) and the combination of Tamoxifen and EM-652.HCl for 161 days, on the growth of human ZR-75-1 breast tumors in ovariectomized nude mice. Tumor size is expressed as the percentage of initial tumor area (Day 1=100%). Data is expressed as means±SEM (n=18-30 tumors/group); ##$p<0.01$ vs EM-652.HCl; ** $p<0.01$ vs OVX. Antiestrogens were administered orally once daily at the dose of 200 µg/mouse in absence of estrogen stimulation.

(p<0.01) while tumor size in mice treated with toremifene increased by 86% (p<0.01) (FIG. 19). The addition of 200 µg of EM-652.HCl to 200 µg of tamoxifen completely inhibited the proliferation observed with tamoxifen alone (FIG. 20). On the other hand, treatment with EM-652.HCl (p=0.44), raloxifene (p=0.11), droloxifene (p=0.36) or GW 5638 (p=0.17) alone did not significantly change ZR-75-1 tumor size compared to the OVX control group, at the end of the experiment. (FIG. 19).

Effects on Categories Response

Figure 21:
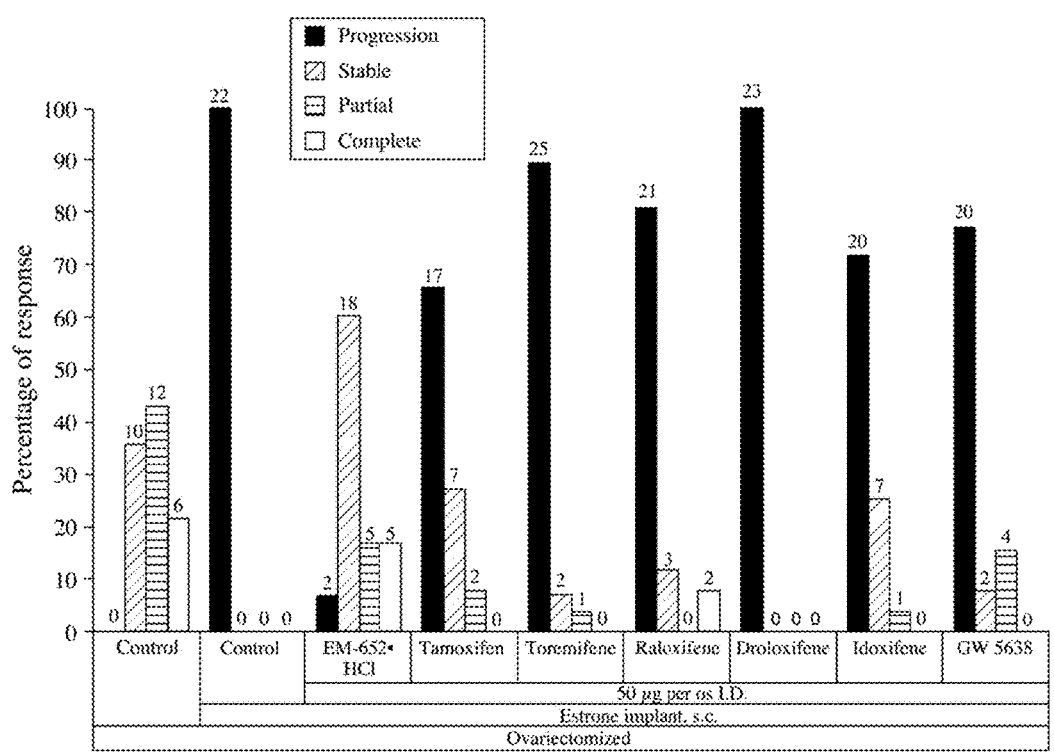
FIG. 21 shows the effects of antiestrogens on categories of response. Effect of a 161-day administration of 7 antiestrogens, on the category of response of human ZR-75-1 breast tumors in ovariectomized nude mice. Complete regression identifies those tumors that were undetectable at the end of treatment; partial regression corresponds to the tumors that regressed ≥50% of their original size; stable response refers to tumors that regressed <50% or progressed 50%; and progression indicates that they progressed more than 50% compared with their original size. Antiestrogens were administered orally once daily at the dose of 50 µg/mouse under estrone stimulation obtained with subcutaneous 0.5-cm silastic implants containing 1:25 ratio of estrone and cholesterol.

Effects of 50 µg of antiestrogen on estrone stimulation. In addition to the effect on tumor size, the category of response achieved by each individual tumor at the end of the experiment is an important parameter of treatment efficacy. In ovariectomized mice, complete, partial, and stable responses were achieved in 21%, 43% and 38% of tumors, respectively, and none of the tumors progressed. On the other hand, in OVX animals supplemented with estrone, 100% of tumors have progressed (FIG. 21). In the EM-652.HCl-treated group of OVX animals supplemented with estrone, complete, partial, and stable responses were seen in 17%, 17%, and 60% of tumors, respectively and only 7% (2 tumors out of 30) have progressed. Under the same conditions of estrone stimulation, treatment with a daily 50 µg dose of any of the other antiestrogens was unable to decrease the percentage of progressing tumors under 60%. In fact, 65% of tumors (17 of 26) progressed in the tamoxifen-treated group, while 89% (25 of 28) progressed with toremifene, 81% progressed (21 of 26) with raloxifene, 100% (23 of 23) progressed with droloxifene, while 71% (20 of 28) progressed with idoxifene and 77% (20 of 26) progressed with GW 5638 (FIG. 21).

Figure 22:
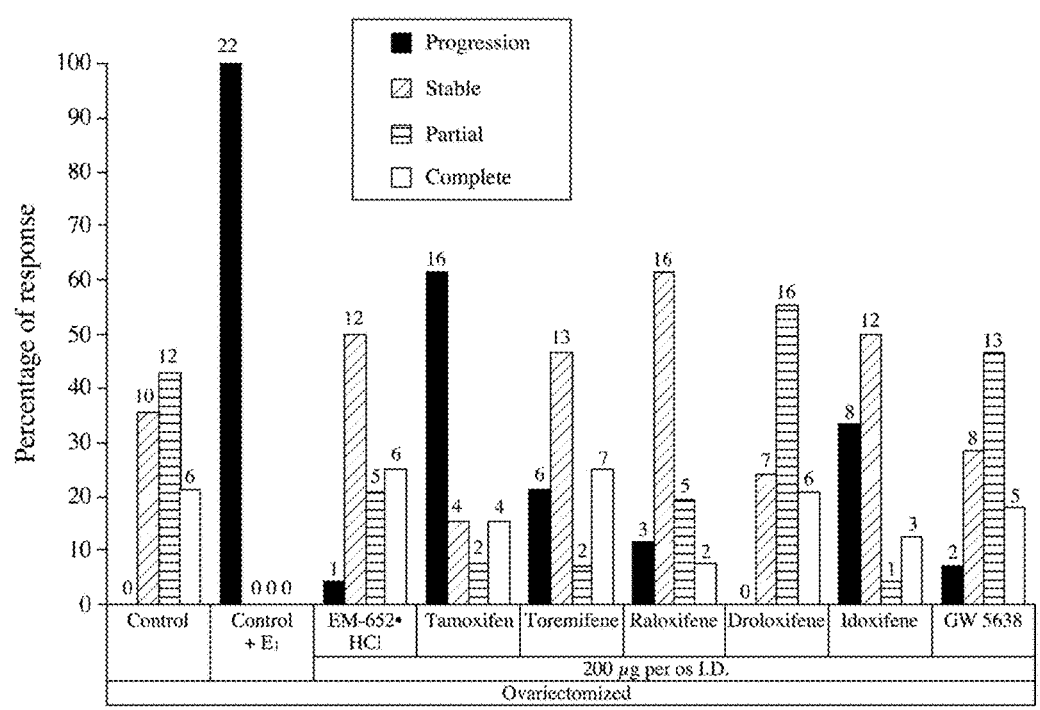
FIG. 22 shows the effects of antiestrogen on categories of response. Effect of a 161-day administration of 7 antiestrogens, on the category of response of human ZR-75-1 breast tumors in ovariectomized nude mice. Complete regression identifies those tumors that were undetectable at the end of treatment; partial regression corresponds to the tumors that regressed ≥50% of their original size; stable response refers to tumors that regressed <50% or progressed 50%; and progression indicates that they progressed more than 50% compared with their original size. Antiestrogens were administered orally once daily at the dose of 200 µg/mouse in absence of estrogen stimulation.
Figure 23:
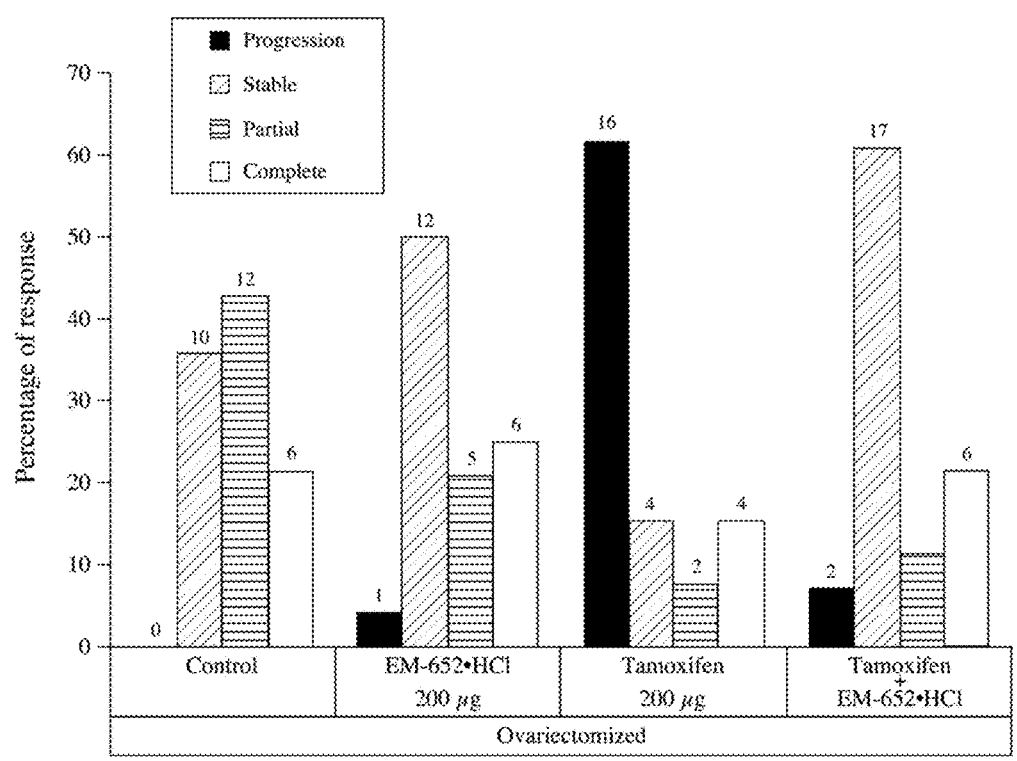
FIG. 23 shows the effects of antiestrogen on categories of response. Effect of a 161-day administration of the antiestrogens Tamoxifen, EM-652.HCl (Acolbifene) and the combination of Tamoxifen and EM-652.HCl, on the category of response of human ZR-75-1 breast tumors in ovariectomized nude mice. Complete regression identifies those tumors that were undetectable at the end of treatment; partial regression corresponds to the tumors that regressed 50% of their original size; stable response refers to tumors that regressed <50% or progressed 50%; and progression indicates that they progressed more than 50% compared with their original size. Antiestrogens were administered orally once daily at the dose of 200 µg/mouse in absence of estrogen stimulation.

Effects of 200 µg of Antiestrogen in the Absence of Estrone Stimulation on Categories Response As illustrated in FIG. 22, tamoxifen, idoxifene and toremifene led to greater proportion of progressing tumors, in the absence of estrone stimulation, than the other antiestrogens. In fact, 62% (16 of 26), 33% (8 of 24) and 21% (6 of 28) of tumors were in the progression category after tamoxifen-, idoxifene- and toremifene treatment at the daily dose of 200 µg, respectively. As can be seen in FIG. 23, the addition of 200 µg of EM-652.HCl to tamoxifen reduced the percentage of progressing tumors with tamoxifen alone from 62% (16 of 26) to 7% when EM-652.HCl was added to tamoxifen (2 of 28).

Effects of Antiestrogens on Thickness of Uterine Epithelial Cells

The height of the endometrial epithelial cells was measured as the most direct parameter of agonistic and antagonistic effect of each compound in the endometrium.

Effect of Daily 50 µg of Antiestrogen in the Presence of Estrone Stimulation on Thickness of Uterine Epithelial Cells At the daily oral dose of 50 µg, EM-652.HCl inhibited the stimulatory effect of estrone on epithelial height by 70%. The efficacy of the six other antiestrogens tested were significantly lower (p<0.01). In fact, droloxifene, GW 5638, raloxifene, tamoxifen, toremifene and idoxifene inhibited estrone stimulation by 17%, 24%, 26%, 32%, 41% and 50%, respectively. (Table 12).

Effect of Daily 200 µg of Antiestrogen in Absence of Estrone Stimulation on Thickness of Uterine Epithelial Cells In the absence of estrone stimulation, EM-652.HCl and droloxifene were the only compounds tested that did not significantly increase the height of epithelial cells (114% and 101% of the OVX control group value, respectively). Tamoxifen (155%), toremifene (135%) and idoxifene (176%) exerted a significant stimulation of uterine epithelial height (p<0.01 vs OVX control group). Raloxifene (122%) and GW 5638 (121%) also exerted a statistically significant stimulation of uterine epithelial height (p<0.05 vs OVX control group (Table 12). The agonistic and antagonistic effects of each antiestrogen measured on uterine and vaginal weight were in accordance with the pattern observed on uterine epithelium thickness (Data not shown).

TABLE 12

| GROUP | n | ENDOMETRIAL EPITHELIUM THICKNESS (µm) ± SEM |
|---|---|---|
| OVX CONTROL | 14 | 18.31 ± 0.04 |
| OVX + $E_1$ CONTROL | 8 | 40.58 $^{b,\,d}$ ± 0.63 |
| OVX + $E_1$ + EM-652•HCl | 14 | 25.06 $^{b}$ ± 0.07 |
| OVX + $E_1$ + TAMOXIFEN | 10 | 33.44 $^{b,\,d}$ ± 0.04 |
| OVX + $E_1$ + TOREMIFENE | 13 | 31.47 $^{b,\,d}$ ± 0.04 |
| OVX + $E_1$ + RALOXIFENE | 12 | 34.72 $^{b,\,d}$ ± 0.06 |
| OVX + $E_1$ + DROLOXIFENE | 12 | 36.71 $^{b,\,d}$ ± 0.12 |
| OVX + $E_1$ + IDOXIFENE | 12 | 29.35 $^{b,\,d}$ ± 0.05 |
| OVX + $E_1$ + GW 5638 | 12 | 35.30 $^{b,\,d}$ ± 0.07 |
| OVX + EM-652•HCl | 12 | 20.79 ± 0.10 |
| OVX + TAMOXIFEN | 11 | 28.47 $^{b,\,d}$ ± 0.05 |
| OVX + EM-652•HCl + TAMOXIFEN | 13 | 27.95 $^{b,\,d}$ ± 0.06 |
| OVX + TOREMIFENE | 13 | 24.75 $^{b,\,c}$ ± 0.04 |
| OVX + RALOXIFENE | 12 | 22.33 $^{a}$ ± 0.05 |
| OVX + DROLOXIFENE | 13 | 18.50 ± 0.07 |
| OVX + IDOXIFENE | 11 | 32.14 $^{b,\,d}$ ± 0.05 |
| OVX + GW 5638 | 13 | 22.22 $^{a}$ ± 0.05 |

$^{a,\,b}$ Experimental versus OVX control mice:
$^{a}$ P < 0.05;
$^{b}$ P < 0.01.
$^{c,\,d}$ Experimental versus EM-652•HCl treated-mice:
$^{c}$ P < 0.05;
$^{d}$ P < 0.01.

Example 9

Radioactivity in the Brain of Female Rats Following a Single Oral Dose of $^{14}$C-EM-800 (20 mg/kg)

Example 8 shows the radioactivity in brain of rats following single oral dose of $^{14}$C-EM-800 (20 mg/kg), a SERM of the present invention. For comparison purposes, values for the blood, plasma, liver (Table 13) and uterus from each of these animals were included. Tissue Distribution and Excretion of Radioactivity Following a Single Oral Dose of $^{14}$C-EM-800 (20 mg/2 ml/kg) to Male and Female Long-Evans Rats. These numbers indicate that the amount of total drug-derived radioactivity in the brain of female Long-Evans rats was very low (ng equiv/g tissue) and was not detected after 12 hr post dose. At 2 hours, radioactivity in the brain was 412 lower than in liver, 21 times lower than in the uterus, 8.4 times lower that in the blood and 13 times lower than in plasma. Since an unknown proportion of total brain radioactivity is due to contamination by blood radioactivity, the values shown in Table X1 for brain radioactivity are an overestimate of the level of $^{14}$C (EM-800)-related radioactivity in the brain tissue itself. Such data suggest that the level of the antiestrogen in the brain tissue is too low, to counteract the effect of exogenous estrogen. It is important to note that some of the radioactivity detected in the brain tissue may be due to residual blood in the tissue (Table 14). Additionally, the radiochemical purity of the $^{14}$C-EM-800 used for this study was minimally 96.25%.

TABLE 13

Mean Concentration of Drug-Derived Radioactivity (ng EM-800 equiv/g tissue) in Selected Tissues of Female Long-Evans Rats Following a Single Oral Dose of $^{14}$C-EM-800 (20 mg/kg) [a]

| Time (hr) | Brain Mean [b] (% CV) | Blood Mean [b] (% CV) | Plasma Mean [b] (% CV) |
|---|---|---|---|
| 2 | 17.6 (29) | 148.7 (22) | 224.6 (20) |
| 4 | 17.1 (29) | 66.9 (45) | 103.2 (39) |
| 6 | 15.6 (8) | 48.3 (29) | 74.1 (31) |
| 8 | 16.8 (31) | 41.1 (12) | 64.1 (14) |
| 12 | 10.0 [c] (87) | 28.7 (54) | 40.7 (55) |
| 24 | 0 (NC) | 4.7 [d] (173) | 10.1 (86) |
| 36 | 0 (NC) | 0 (NC) | 0 (NC) |
| 48 | 0 (NC) | 0 (NC) | 0 (NC) |
| 72 | 0 (NC) | 0 (NC) | 0 (NC) |
| 96 | 0 (NC) | 0 (NC) | 0 (NC) |
| 168 | 0 (NC) | 0 (NC) | 0 (NC) |

[a] Values from report tables for LREM 1129 (EM-800: Tissue Distribution and Excretion of Radioactivity Following a Single Oral Dose of $^{14}$C-EM-800 (20 mg/2 mL/kg) to Male and Female Long-Evans Rats).
[b] Limit of quantification (LOQ) of 1.2 ng EM-800 equivalent.
[c] One sample below the LOQ; 0 used in calculation of mean.
[d] Two samples below the LOQ; 0 used in calculation of mean.
% CV: Coefficient of variation expressed as a percent, where n = 3.
NC: Not calculated.

TABLE 14

Mean Concentration of Drug-Derived Radioactivity (µg EM-800 equiv/g tissue) in Selected Tissues of Female Long-Evans Rats Following a Single Oral Dose of $^{14}$C-EM-800 (20 mg/kg) [a]

| Time (hr) | Brain Mean [b] (% CV) | Liver Mean [b] (% CV) | Uterus Mean [b] (% CV) | Blood Mean [b] (% CV) | Plasma Mean [b] (% CV) |
|---|---|---|---|---|---|
| 2 | 0.0176 (29) | 7.2547 (30) | 0.3675 (36) | 0.1487 (22) | 0.2246 (20) |
| 4 | 0.0171 (29) | 3.2201 (48) | 0.2866 (83) | 0.0669 (45) | 0.1032 (39) |
| 6 | 0.0156 (8) | 2.7462 (8) | 0.2757 (19) | 0.0483 (29) | 0.0741 (31) |
| 8 | 0.0168 (31) | 2.7748 (8) | 0.3332 (46) | 0.0411 (12) | 0.0641 (14) |
| 12 | 0.0100 [c] (87) | 1.8232 (38) | 0.2407 (25) | 0.0287 (54) | 0.0407 (55) |
| 24 | 0 (NC) | 0.6391 (52) | 0.0837 (54) | 0.0047 [d] (173) | 0.0101 (86) |
| 36 | 0 (NC) | 0.4034 (22) | 0.0261 (15) | 0 (NC) | 0 (NC) |
| 48 | 0 (NC) | 0.2196 (37) | 0.0238 (44) | 0 (NC) | 0 (NC) |
| 72 | 0 (NC) | 0.1326 (4) | 0 (NC) | 0 (NC) | 0 (NC) |
| 96 | 0 (NC) | 0.0944 (15) | 0 (NC) | 0 (NC) | 0 (NC) |
| 168 | 0 (NC) | 0.0348 (14) | 0 (NC) | 0 (NC) | 0 (NC) |

[a] Values from report tables for LREM 1129 (EM-800: Tissue Distribution and Excretion of Radioactivity Following a Single Oral Dose of $^{14}$C-EM-800 (20 mg/2 mL/kg) to Male and Female Long-Evans Rats).
[b] Limit of quantification (LOQ) of 1.2 ng EM-800 equivalent.
[c] One sample below the LOQ; 0 used in calculation of mean.
[d] Two samples below the LOQ; 0 used in calculation of mean.
% CV: Coefficient of variation expressed as a percent, where n = 3.
NC: Not calculated.

Example 10

Figure 24:
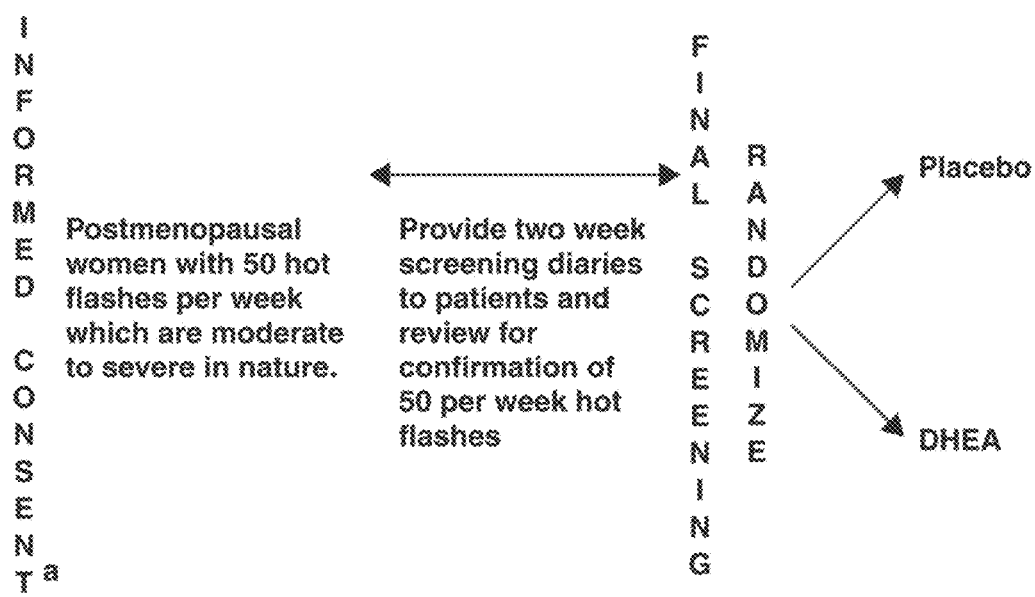
FIG. 24 is a Study Design Diagram of the phase II-III placebo-controlled study to evaluate the effects of DHEA on vasomotor symptoms (hot flushes) in postmenopausal women.

Clinical Trial ERC-205
Étude De Phase II-IIII Randomisée Avec Contrôle Placebo Pour Évaluer Les Effets De La Dhea Sur Les Symptômes Vasomoteurs (Bouffées De Chaleur)—Phase II-III Placebo-Controlled, Study to Evaluate the Effects of Dhea on Vasomotor Symptoms (Hot Flushes) in Postmenopausal Women.
Study Design Summary As illustrated in FIG. 24, this was a randomized, placebo controlled, study to evaluate the effect of DHEA on reducing vasomotor symptoms (hot flushes) compared to placebo administration. Postmenopausal women experiencing ≥50 moderate or severe hot flushes per week (as determined by a two week diary) were randomized to receive a daily dose of either placebo or 50 mg DHEA. Fifty evaluable participants (25 patients per arm) were treated for four months with a daily assessment of hot flushes recorded in a diary completed by each participant.

Postmenopausal women aged 40 to 70 years with ≥50 moderate or severe hot flushes per week, as confirmed by a two-week screening hot flush diary were enrolled after signing informed consent. The protocol was approved by the Institutional Review Board (IRB) of Le Centre Hospitalier de l'Université Laval and by Health Canada.

Women had to satisfy either a or b or c:
a. No menses for at least one year, or;
b. FSH levels ≥40 mIU/mL (within 60 days prior to Day 1) in women with no menses months but <12 months, or hysterectomized women who were premenopausal at the time of hysterectomy, or;
c. Previous bilateral oophorectomy.

A normal PAP smear (which includes inflammatory changes) and a normal bilateral mammogram within 12 months of randomization had to be available.

An endometrial thickness of 4 mm or less at transvaginal ultrasonography was required.

The primary endpoint was the change from Baseline in the weekly frequency of moderate to severe hot flushes at Week 16, after four months of treatment. The objectives also included the change from Baseline in the weekly frequency of all hot flushes and the change from Baseline in the weekly weighted severity score.

The secondary endpoints were the safety evaluation of DHEA as well as quality of life.

The response endpoint is the patient's paper diary which was filled in daily to specify the number and type of hot flushes as follows:
0 None.
1 Mild=sensation of heat without perspiration.
2 Moderate=sensation of heat with perspiration and no cessation of activity necessary.
3 Severe=sensation of heat with perspiration necessitating cessation of activity. This includes night sweats.

The hot flush diary began as a Screening diary for two weeks prior to randomization whereby patients had to complete the diary daily, recording the number and severity of hot flushes. The patients had to record an average of 50 or more moderate or severe hot flushes per week over the two-week period to be eligible (i.e., at least 100 hot flushes documented on the two week Screening diary).

Once randomized, the patient completed eight, two-week hot flush diaries upon beginning study medication. The diaries had to be filled out on a daily basis. The first diary was completed over the first two weeks and be returned on the two week visit. The second two-week diary was completed over the next two weeks of the first four week treatment period and was returned at the four week visit. At 4, 8, 12 and 16 week visits, two two-week diaries for hot flushes were collected.

Diary and blinded medication began on the same day (ie, on day 1. The patient began recording hot flushes when she woke up on the same day she planned to begin taking the study medication).

Results

Figure 25:
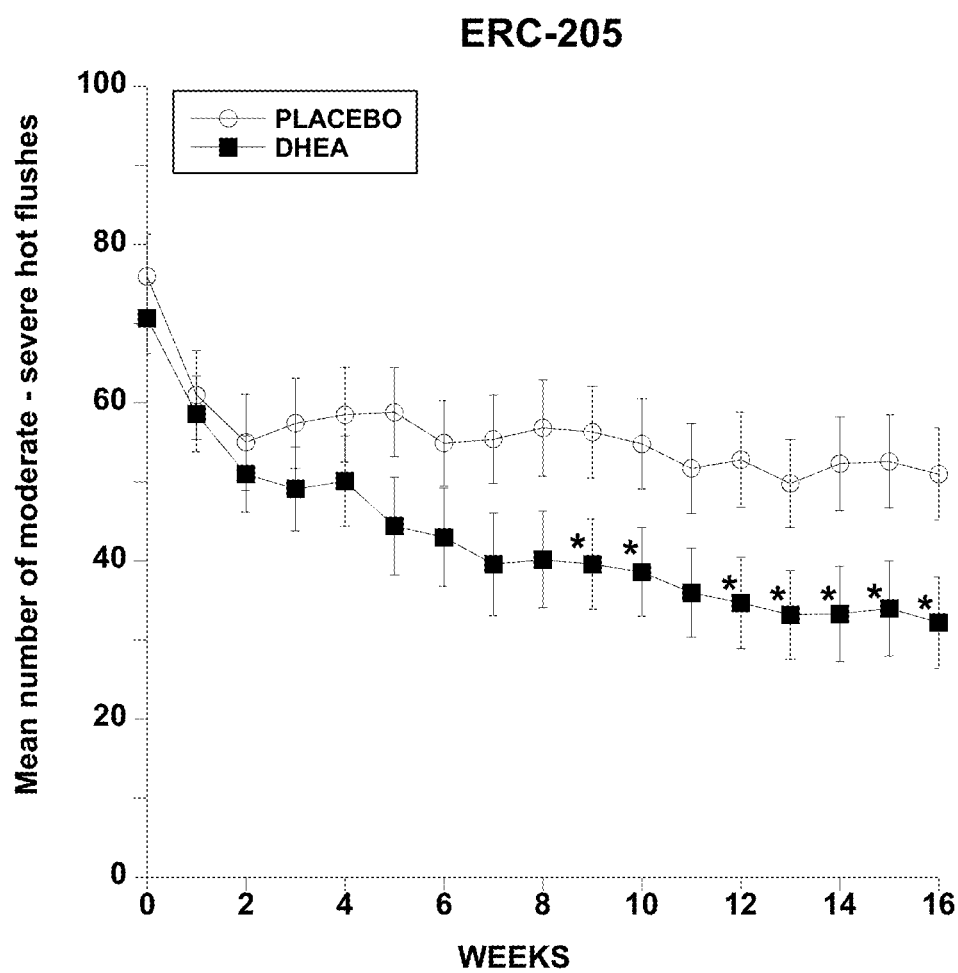
FIG. 25 shows the effect of a daily dose of DHEA or placebo on mean number of moderate to severe hot flushes during 16 weeks of treatment (*, $p<0.05$ DHEA versus placebo).

As illustrated in FIG. 25 and Table 15, the number of moderate to severe hot flushes decreased from 70.7±4.5 per week at screening to 50.1±5.7 at week 4 (N.S. US placebo), 40.2 1 6.1 at week 8, 34.7±5.8 at week 12 (p<0.05 vs. placebo) and 32.2±5.8 at week 16 (p<0.0.5 vs. placebo). Placebo cause a 32.9% decrease compared to 54.5% for DHEA.

Figure 26:
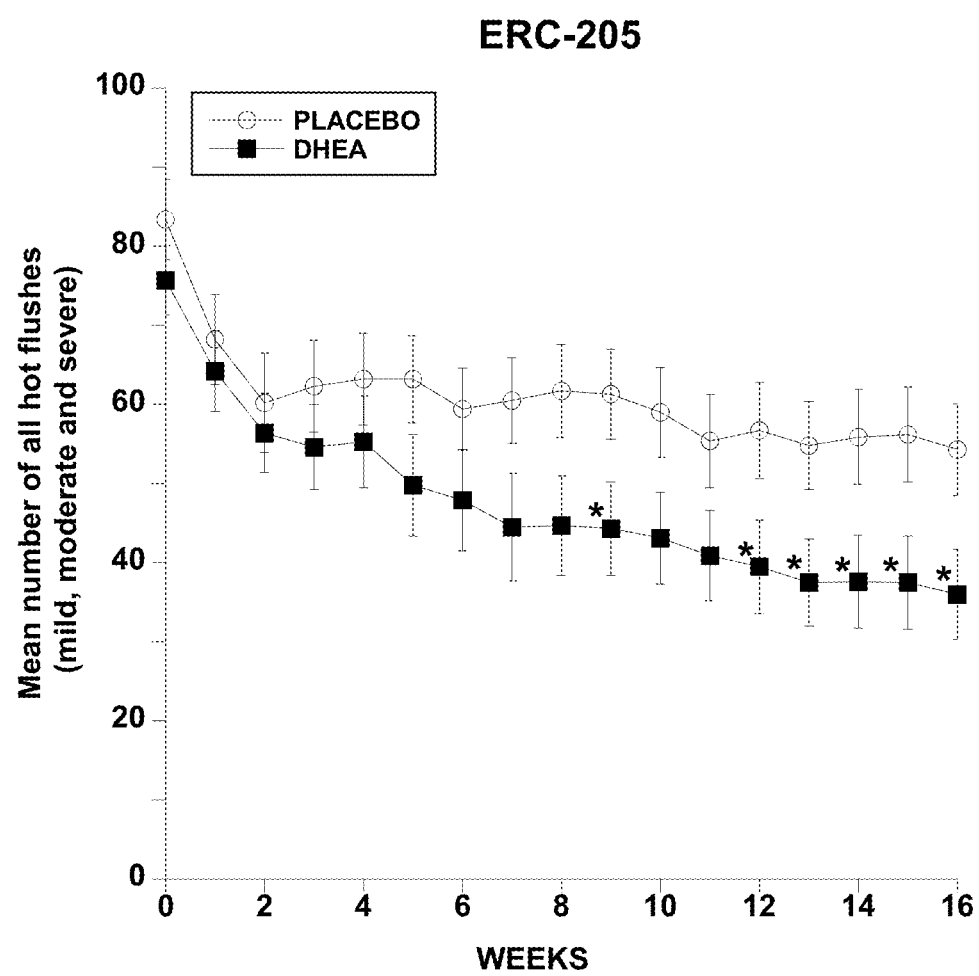
FIG. 26 shows the treatment with a daily 50 mg dose of DHEA or placebo on mean number of all hot flushes (mild, moderate and severe) during 16 weeks of treatment (*, $p<0.05$ DHEA versus placebo).

A similar effect was observed on the frequency of all hot flushes (FIG. 26, Table 16) with a prescreening value of 75.5±4.4 hot flushes per week to 55.3±5.8 at week 4 (N.S. vs. placebo), 44.7±6.3 at week 8, 39.5±5.9 at week 12 (p<0.05 vs. placebo) and 36.0±5.7 at week 16 (p<0.05 vs. placebo). Placebo caused a 34.9% decrease compared to 52.4% for DHEA.

When the hot flushes were attributed a score of 1 for mild, 2 for moderate and 3 for severe, it can be seen that the values went form 187.1±13.9 to 87.2±15.8 in the DHEA groups compared to 196.3±13.6 to 130±14.1 in the placebo groups at 16 weeks (p<0.05). Placebo caused a 18.0% decrease versus 53.4% for DHEA, thus indicating a 3.0-fold higher efficacy of DHEA.

As illustrated in Table 18, the effect of DHEA was exerted at a greater degree on the moderate to severe hot flushes an effect better illustrated on the weighted severity score when the value was reduced by 99.1±15.6 with DHEA and 68.6±15.6 for placebo. This effect is better illustrated in Table 19 where the mean number of hot flushes in the groups of women having 71 or more hot flushes per week at screening went from 94.7±7.9 to 57.8±8.3 in the placebo group went from 88.5±7.1 to 31.6±11.6 in the group of women who received DHEA. Such data show a 65% (64.3% for DHEA versus 39.0% for placebo) greater inhibition by DHEA in the women most affected by vasomotor symptoms. In fact, in women having between 50 and 70 moderate to severe hot flushes per week, the number went from 56.7±1.3 per week at prescreening to 32.7±6.2 at week 6 (43.3% decrease) in women who received DHEA compared to a 24.7% decrease with placebo, thus indicating a 43% inhibition by DHEA over the placebo effect.

Since the number of mild hot flushes is relatively low (comparison of Tables 18 and 19), similar conclusions are found in Table 20. The number of hot flushes in women having more than 70 mild, moderate plus severe hot flushes is decreased from 91.0±7.0 per week at prescreening to 36.3±11.5 at week 16 in women receiving DHEA (60% decrease). In women receiving placebo the number of all hot flushes goes from 100.4±7.9 at screening to 61.3±8.9 at week 16 for a 39.9% decrease. Such data show a 50% greater efficacy of DHEA in the women having the largest number of hot flushes of all degrees of severity.

Analogous conclusions are reached when a weighted severity score is used for calculations (Table 21). When women having more than 70 hot flushes per week are considered, the score goes from 241.6±21.1 at screening to 95.2±34.3 at week 16 in women receiving DHEA (61.6% decrease) while for placebo, the value decreases from 242.0±21.6 to 141.3±20.1 at week 16 (41.6% decrease). In women having between 50 and 70 hot flushes per week at screening, the values go from 144.3±6.7 at screening to 81.6±13.6 at week 16 in women who received DHEA (43.5% decrease) compared to values 154.2±3.7 and 118.8±20.2 for the placebo groups (33.0% decrease).

Conclusion

The present data demonstrated the efficacy of 50 mg DHEA treatment for alleviating vasomotor symptoms as assessed by the significant decrease in the total number of moderate to severe hot flushes or all hot flushes, as well as by the significant reduction of the hot flush weekly severity weighted score.

TABLE 15

NUMBER OF MODERATE TO SEVERE HOT FLUSHES PER WEEK

| GROUP | VALUE | Screening (mean of 2 w) | Week 1 | Week 2 | Week 3 | Week 4 | Week 5 | Week 6 | Week 7 | Week 8 | Week 9 | Week 10 | Week 11 | Week 12 | Week 13 | Week 14 | Week 15 | Week 16 |
|---|---|---|---|---|---|---|---|---|---|---|---|---|---|---|---|---|---|---|
| PLACEBO | n | 25 | 25 | 25 | 25 | 25 | 25 | 25 | 24 | 24 | 24 | 24 | 24 | 24 | 24 | 24 | 24 | 24 |
| | MEAN | 76.0 | 61.0 | 55.0 | 57.4 | 58.5 | 58.8 | 54.9 | 55.4 | 56.8 | 56.3 | 54.8 | 51.7 | 52.8 | 49.8 | 52.3 | 52.6 | 51.0 |
| | SEM | 8.3 | 5.8 | 6.1 | 5.7 | 5.0 | 5.6 | 5.4 | 5.8 | 8.1 | 5.8 | 5.7 | 5.7 | 6.0 | 5.5 | 5.9 | 5.9 | 5.8 |
| | MIN | 52.8 | 8 | 3 | 3 | 4 | 3 | 1 | 0 | 0 | 0 | 0 | 0 | 0 | 0 | 0 | 0 | 1 |
| | MAX | 16.8 | 127 | 116 | 110 | 125 | 111 | 117 | 104 | 118 | 115 | 108 | 106 | 115 | 110 | 112 | 98 | 103 |
| DHEA (50 mg) | n | 25 | 25 | 25 | 25 | 25 | 22 | 22 | 22 | 22 | 22 | 22 | 22 | 22 | 22 | 22 | 22 | 22 |
| | MEAN | 70.7 | 58.6 | 51.0 | 49.1 | 50.1 | 44.4 | 43.0 | 39.6 | 40.2 | 39.6 | 38.6 | 36.0 | 34.7 | 33.2 | 33.3 | 34.0 | 32.2 |
| | SEM | 4.5 | 4.8 | 4.8 | 8.3 | 5.7 | 8.2 | 8.2 | 6.5 | 8.1 | 5.7 | 5.0 | 5.8 | 8.5 | 8.5 | 5.0 | 6.0 | 8.8 |
| | MIN | 50.5 | 25 | 5 | 2 | 7 | 0 | 0 | 0 | 0 | 0 | 0 | 0 | 0 | 0 | 0 | 0 | 0 |
| | MAX | 145.5 | 129 | 121 | 110 | 131 | 121 | 114 | 123 | 103 | 107 | 110 | 107 | 105 | 101 | 102 | 110 | 104 |

TABLE 16

NUMBER OF ALL HOT FLUSHES PER WEEK

| GROUP | VALUE | Screening (mean of 2 w) | Week 1 | Week 2 | Week 3 | Week 4 | Week 5 | Week 6 | Week 7 | Week 8 | Week 9 | Week 10 | Week 11 | Week 12 | Week 13 | Week 14 | Week 15 | Week 16 |
|---|---|---|---|---|---|---|---|---|---|---|---|---|---|---|---|---|---|---|
| PLACEBO | n | 25 | 25 | 25 | 25 | 25 | 25 | 25 | 24 | 24 | 24 | 24 | 24 | 24 | 24 | 24 | 24 | 24 |
| | MEAN | 83.4 | 68.2 | 60.2 | 62.3 | 63.2 | 63.2 | 59.4 | 60.5 | 61.7 | 61.3 | 59.0 | 55.4 | 56.7 | 54.8 | 55.9 | 56.2 | 54.3 |
| | SEM | 5.1 | 5.7 | 6.3 | 5.8 | 5.8 | 5.5 | 5.2 | 5.4 | 5.9 | 5.7 | 5.7 | 5.9 | 8.1 | 5.6 | 6.0 | 6.0 | 5.8 |
| | MIN | 52.5 | 12 | 7 | 8 | 17 | 7 | 6 | 1 | 1 | 0 | 0 | 0 | 0 | 0 | 3 | 6 | 8 |
| | MAX | 168 | 128 | 117 | 114 | 130 | 111 | 118 | 110 | 121 | 118 | 109 | 110 | 121 | 110 | 113 | 107 | 103 |
| DHEA (50 mg) | n | 25 | 25 | 25 | 25 | 25 | 22 | 22 | 22 | 22 | 22 | 22 | 22 | 22 | 22 | 22 | 22 | 22 |
| | MEAN | 75.7 | 64.2 | 56.4 | 54.6 | 55.3 | 49.8 | 47.9 | 44.5 | 44.7 | 44.3 | 43.1 | 40.9 | 39.5 | 37.5 | 37.6 | 37.5 | 36.0 |
| | SEM | 4.4 | 5.1 | 5.0 | 5.4 | 5.8 | 6.4 | 6.4 | 8.8 | 6.3 | 5.9 | 5.8 | 5.7 | 5.9 | 5.5 | 5.9 | 5.9 | 5.7 |
| | MIN | 51 | 26 | 7 | 2 | 7 | 0 | 0 | 0 | 0 | 0 | 0 | 0 | 0 | 0 | 0 | 0 | 0 |
| | MAX | 147 | 129 | 121 | 110 | 131 | 121 | 114 | 123 | 103 | 107 | 110 | 108 | 105 | 101 | 102 | 110 | 104 |

TABLE 17

WEIGHTED SEVERITY SCORE OF HOT FLUSHES PER WEEK

| GROUP | VALUE | Screening (mean of 2 w) | Week 1 | Week 2 | Week 3 | Week 4 | Week 5 | Week 6 | Week 7 | Week 8 | Week 9 | Week 10 | Week 11 | Week 12 | Week 13 | Week 14 | Week 15 | Week 16 |
|---|---|---|---|---|---|---|---|---|---|---|---|---|---|---|---|---|---|---|
| PLACEBO | n | 25 | 25 | 25 | 25 | 25 | 25 | 25 | 24 | 24 | 24 | 24 | 24 | 24 | 24 | 24 | 24 | 24 |
| | MEAN | 196.3 | 158.6 | 140.8 | 147.5 | 148.6 | 148.0 | 139.7 | 142.6 | 145.9 | 143.7 | 139.7 | 131.0 | 133.6 | 127.1 | 132.7 | 133.6 | 130.0 |
| | SEM | 13.6 | 13.8 | 14.8 | 13.7 | 13.9 | 12.8 | 12.6 | 13.1 | 14.4 | 13.7 | 13.4 | 13.8 | 14.4 | 13.4 | 14.4 | 14.2 | 14.1 |
| | MIN | 139.5 | 20 | 13 | 14 | 30 | 13 | 8 | 1 | 1 | 0 | 0 | 0 | 0 | 0 | 3 | 8 | 10 |
| | MAX | 433.5 | 325 | 295 | 279 | 297 | 263 | 275 | 253 | 278 | 278 | 253 | 251 | 273 | 257 | 262 | 232 | 242 |
| DHEA (50 mg) | n | 25 | 25 | 25 | 25 | 25 | 22 | 22 | 22 | 22 | 22 | 22 | 22 | 22 | 22 | 22 | 22 | 22 |
| | MEAN | 187.1 | 156.0 | 137.5 | 132.5 | 135.7 | 120.9 | 115.2 | 108.3 | 109.4 | 106.5 | 104.5 | 98.2 | 92.7 | 90.1 | 90.9 | 91.8 | 87.2 |
| | SEM | 13.9 | 13.6 | 13.6 | 14.4 | 16.1 | 16.5 | 17.3 | 18.5 | 17.1 | 15.7 | 16.7 | 15.5 | 15.2 | 15.0 | 15.8 | 16.4 | 15.8 |
| | MIN | 116 | 86 | 15 | 4 | 20 | 0 | 0 | 0 | 0 | 0 | 0 | 0 | 0 | 0 | 0 | 0 | 0 |
| | MAX | 404 | 353 | 353 | 326 | 386 | 330 | 335 | 357 | 302 | 314 | 327 | 322 | 315 | 301 | 306 | 330 | 311 |

TABLE 18

MEAN CHANGE IN FREQUENCY AND SEVERITY OF HOT FLUSHES (HF) FROM BASELINE

| | | Frequency of moderate-severe HF | | | | Frequency of all HF | | | | Weighted severity score of HF | | | |
|---|---|---|---|---|---|---|---|---|---|---|---|---|---|
| GROUP | VALUE | Week 4 | Week 8 | Week 12 | Week 16 | Week 4 | Week 8 | Week 12 | Week 16 | Week 4 | Week 8 | Week 12 | Week 16 |
| PLACEBO | n | 25 | 24 | 24 | 24 | 25 | 24 | 24 | 24 | 25 | 24 | 24 | 24 |
| | MEAN | -17.4 | -19.8 | -23.8 | -25.7 | -20.1 | -22.1 | -27.1 | -29.5 | -47.7 | -52.7 | -65.0 | -68.6 |
| | SEM | 5.6 | 6.0 | 5.8 | 5.7 | 5.2 | 5.6 | 6.0 | 5.7 | 14.1 | 15.8 | 15.7 | 15.6 |
| | MIN | -70.5 | -78.5 | -81.5 | -80.5 | -86 | -77.5 | -85.5 | -87.5 | -187.5 | -206.5 | -227.5 | -228.5 |
| | MAX | 21 | 18 | 30 | 21 | 15.5 | 9.5 | 24.5 | 15.5 | 51.5 | 61 | 62 | 71 |
| DHEA (50 mg) | n | 25 | 22 | 22 | 22 | 25 | 22 | 22 | 22 | 25 | 22 | 22 | 22 |
| | MEAN | -20.6 | -30.1 | -35.6 | -38.1 | -20.4 | -31.0 | -36.2 | -39.8 | -51.4 | -76.9 | -93.6 | -99.1 |
| | SEM | 5.3 | 6.2 | 6.5 | 5.9 | 5.3 | 6.1 | 6.5 | 5.9 | 14.0 | 16.6 | 17.4 | 15.6 |
| | MIN | -74 | -84 | -82 | -76.5 | -74.5 | -75 | -82 | -77 | -186.5 | -202 | -240.5 | -205 |
| | MAX | 27 | 18.5 | 29.5 | 25.5 | 25.5 | 18.5 | 29 | 25 | 77.5 | 39 | 57.5 | 53.5 |

TABLE 19

NUMBER OF MODERATE TO SEVERE HOT FLUSHES PER WEEK

| GROUP | STRATA | VALUE | Screening (mean of 2 w) | Week 1 | Week 2 | Week 3 | Week 4 | Week 5 | Week 6 | Week 7 | Week 8 | Week 9 |
|---|---|---|---|---|---|---|---|---|---|---|---|---|
| PLACEBO | 50 to 70 hot flushes per week at screening | n | 13 | 13 | 13 | 13 | 13 | 13 | 13 | 12 | 12 | 12 |
| | | MEAN | 58.7 | 46.8 | 40.8 | 49.5 | 48.2 | 48.6 | 47.1 | 46.3 | 48.0 | 50.8 |
| | | SEM | 1.4 | 5.8 | 7.2 | 7.5 | 6.4 | 8.3 | 6.1 | 5.2 | 8.5 | 7.0 |
| | | MIN | 52.5 | 5 | 3 | 3 | 4 | 3 | 1 | 0 | 0 | 0 |
| | | MAX | 58 | 81 | 85 | 101 | 87 | 88 | 88 | 73 | 50 | 90 |
| | ≥71 hot flushes per week at screening | n | 12 | 12 | 12 | 12 | 12 | 12 | 12 | 12 | 12 | 12 |
| | | MEAN | 94.7 | 76.3 | 70.3 | 66.1 | 69.8 | 69.8 | 63.3 | 64.5 | 65.7 | 61.8 |
| | | SEM | 7.9 | 7.9 | 8.0 | 5.1 | 9.6 | 8.5 | 8.8 | 8.9 | 9.7 | 9.2 |
| | | MIN | 71 | 21 | 22 | 18 | 18 | 20 | 13 | 9 | 10 | 7 |
| | | MAX | 165 | 127 | 116 | 110 | 125 | 111 | 117 | 104 | 118 | 116 |

TABLE 19-continued

| | | | | | | | | | | | |
|---|---|---|---|---|---|---|---|---|---|---|---|
| DHEA (50 mg) | 50 to 70 | n | 14 | 14 | 14 | 14 | 14 | 13 | 13 | 13 | 13 | 13 |
| | hot flushes | MEAN | 56.7 | 54.2 | 49.0 | 46.5 | 44.0 | 38.3 | 39.8 | 34.7 | 38.1 | 38.5 |
| | per week | SEM | 1.8 | 4.7 | 4.3 | 8.2 | 5.7 | 8.2 | 6.4 | 5.6 | 5.2 | 6.2 |
| | at screening | MIN | 50.5 | 26 | 5 | 2 | 7 | 0 | 0 | 0 | 0 | 0 |
| | | MAX | 70.5 | 90 | 81 | 90 | 82 | 82 | 72 | 70 | 75 | 73 |
| | ≥71 | n | 11 | 11 | 11 | 11 | 11 | 8 | 9 | 9 | 9 | 9 |
| | hot flushes | MEAN | 88.5 | 64.1 | 53.5 | 52.5 | 57.8 | 53.2 | 47.6 | 46.7 | 43.3 | 41.1 |
| | per week | SEM | 7.1 | 9.0 | 9.3 | 9.2 | 10.7 | 12.0 | 12.5 | 13.9 | 12.5 | 11.2 |
| | at screening | MIN | 72.5 | 25 | 22 | 15 | 10 | 4 | 8 | 6 | 5 | 6 |
| | | MAX | 145.6 | 128 | 121 | 110 | 131 | 121 | 114 | 123 | 103 | 107 |

| | | | NUMBER OF MODERATE TO SEVERE HOT FLUSHES PER WEEK | | | | | | |
|---|---|---|---|---|---|---|---|---|---|
| GROUP | STRATA | VALUE | Week 10 | Week 11 | Week 12 | Week 13 | Week 14 | Week 15 | Week 16 |
| PLACEBO | 50 to 70 | n | 12 | 12 | 12 | 12 | 12 | 12 | 12 |
| | hot flushes | MEAN | 49.2 | 44.1 | 47.9 | 44.9 | 46.3 | 46.8 | 44.2 |
| | per week | SEM | 7.1 | 6.7 | 7.7 | 5.9 | 8.7 | 5.5 | 7.9 |
| | at screening | MIN | 0 | 0 | 0 | 0 | 0 | 0 | 1 |
| | | MAX | 85 | 83 | 96 | 77 | 100 | 95 | 57 |
| | ≥71 | n | 12 | 12 | 12 | 12 | 12 | 12 | 12 |
| | hot flushes | MEAN | 60.4 | 59.3 | 57.8 | 54.7 | 58.2 | 58.4 | 57.8 |
| | per week | SEM | 8.5 | 9.0 | 9.4 | 8.8 | 8.1 | 8.1 | 8.3 |
| | at screening | MIN | 6 | 2 | 7 | 9 | 10 | 8 | 8 |
| | | MAX | 108 | 106 | 115 | 110 | 112 | 58 | 103 |
| DHEA (50 mg) | 50 to 70 | n | 13 | 13 | 13 | 13 | 13 | 13 | 13 |
| | hot flushes | MEAN | 36.6 | 35.6 | 35.8 | 32.8 | 34.2 | 33.7 | 32.7 |
| | per week | SEM | 6.4 | 6.2 | 5.8 | 6.5 | 7.2 | 8.6 | 8.2 |
| | at screening | MIN | 0 | 0 | 0 | 0 | 0 | 0 | 0 |
| | | MAX | 75 | 70 | 80 | 78 | 77 | 74 | 76 |
| | ≥71 | n | 9 | 9 | 8 | 9 | 9 | 9 | 8 |
| | hot flushes | MEAN | 41.6 | 36.4 | 33.1 | 33.9 | 32.0 | 34.4 | 31.6 |
| | per week | SEM | 10.6 | 10.8 | 10.5 | 10.4 | 10.8 | 11.7 | 11.6 |
| | at screening | MIN | 12 | 5 | 1 | 3 | 4 | 5 | 1 |
| | | MAX | 110 | 107 | 105 | 101 | 102 | 110 | 104 |

TABLE 20

| | | | NUMBER OF ALL HOT FLUSHES PER WEEK | | | | | | | | | |
|---|---|---|---|---|---|---|---|---|---|---|---|---|
| GROUP | STRATA | VALUE | Screening (mean of 2 w) | Week 1 | Week 2 | Week 3 | Week 4 | Week 5 | Week 6 | Week 7 | Week 8 | Week 9 |
| PLACEBO | 50 to 70 | n | 13 | 13 | 13 | 13 | 13 | 13 | 13 | 12 | 12 | 12 |
| | hot flushes | MEAN | 67.7 | 54.3 | 45.4 | 53.8 | 53.2 | 52.8 | 51.5 | 50.9 | 53.3 | 55.4 |
| | per week | SEM | 2.2 | 5.2 | 7.5 | 7.8 | 5.8 | 6.0 | 5.5 | 5.4 | 6.3 | 6.4 |
| | at screening | MIN | 52.5 | 12 | 7 | 5 | 17 | 7 | 8 | 1 | 1 | 0 |
| | | MAX | 78.5 | 83 | 92 | 102 | 87 | 91 | 88 | 73 | 81 | 99 |
| | ≥71 | n | 12 | 12 | 12 | 12 | 12 | 12 | 12 | 12 | 12 | 12 |
| | hot flushes | MEAN | 100.4 | 83.3 | 76.2 | 71.5 | 74.2 | 74.4 | 68.0 | 70.2 | 70.1 | 67.2 |
| | per week | SEM | 7.9 | 8.5 | 8.3 | 8.3 | 9.5 | 8.4 | 8.5 | 8.7 | 9.7 | 9.5 |
| | at screening | MIN | 71 | 32 | 34 | 32 | 34 | 35 | 32 | 22 | 23 | 16 |
| | | MAX | 165 | 128 | 117 | 114 | 130 | 111 | 115 | 110 | 121 | 115 |
| DHEA (50 mg) | 50 to 70 | n | 14 | 14 | 14 | 14 | 14 | 13 | 13 | 13 | 13 | 13 |
| | hot flushes | MEAN | 63.7 | 60.8 | 55.3 | 52.3 | 49.4 | 42.7 | 43.7 | 39.2 | 41.8 | 42.4 |
| | per week | SEM | 3.0 | 5.9 | 5.7 | 8.7 | 8.3 | 5.9 | 7.0 | 8.7 | 7.0 | 7.0 |
| | at screening | MIN | 51 | 30 | 7 | 2 | 7 | 0 | 0 | 0 | 0 | 0 |
| | | MAX | 82 | 106 | 84 | 90 | 87 | 82 | 72 | 72 | 85 | 81 |
| | ≥71 | n | 11 | 11 | 11 | 11 | 11 | 9 | 9 | 9 | 9 | 9 |
| | hot flushes | MEAN | 91.0 | 68.6 | 57.9 | 57.5 | 62.7 | 60.0 | 53.9 | 52.2 | 48.9 | 47.0 |
| | per week | SEM | 7.0 | 9.1 | 9.1 | 9.2 | 10.4 | 11.8 | 12.3 | 13.7 | 12.0 | 10.8 |
| | at screening | MIN | 72.5 | 26 | 24 | 15 | 22 | 14 | 13 | 7 | 9 | 14 |
| | | MAX | 147 | 129 | 121 | 110 | 131 | 121 | 114 | 123 | 103 | 107 |

| | | | NUMBER OF ALL HOT FLUSHES PER WEEK | | | | | | |
|---|---|---|---|---|---|---|---|---|---|
| GROUP | STRATA | VALUE | Week 10 | Week 11 | Week 12 | Week 13 | Week 14 | Week 15 | Week 16 |
| PLACEBO | 50 to 70 | n | 12 | 12 | 12 | 12 | 12 | 12 | 12 |
| | hot flushes | MEAN | 53.8 | 48.1 | 51.4 | 49.1 | 49.8 | 49.8 | 47.3 |
| | per week | SEM | 5.7 | 6.6 | 7.2 | 6.7 | 8.3 | 7.8 | 7.2 |
| | at screening | MIN | 0 | 0 | 0 | 0 | 3 | 6 | 8 |
| | | MAX | 85 | 83 | 95 | 85 | 100 | 98 | 87 |
| | ≥71 | n | 12 | 12 | 12 | 12 | 12 | 12 | 12 |
| | hot flushes | MEAN | 64.3 | 62.7 | 61.9 | 60.4 | 62.0 | 62.6 | 61.3 |
| | per week | SEM | 9.2 | 9.6 | 10.0 | 8.9 | 8.6 | 8.9 | 8.9 |

TABLE 20-continued

| | | | | | | | | | | |
|---|---|---|---|---|---|---|---|---|---|---|
| | | at screening | MIN | 11 | 4 | 11 | 12 | 14 | 13 | 9 |
| | | | MAX | 109 | 110 | 121 | 110 | 113 | 107 | 103 |
| DHEA (50 mg) | 50 to 70 | n | | 13 | 13 | 13 | 13 | 13 | 13 | 13 |
| | | hot flushes | MEAN | 40.5 | 39.5 | 39.7 | 36.2 | 37.8 | 36.5 | 35.7 |
| | | per week | SEM | 6.8 | 6.5 | 7.1 | 6.5 | 7.3 | 6.5 | 5.8 |
| | | at screening | MIN | 0 | 0 | 0 | 0 | 0 | 0 | 0 |
| | | | MAX | 75 | 70 | 80 | 78 | 77 | 74 | 78 |
| | ≥71 | n | | 9 | 9 | 9 | 9 | 9 | 9 | 9 |
| | | hot flushes | MEAN | 46.9 | 42.8 | 39.3 | 39.3 | 37.3 | 38.8 | 36.3 |
| | | per week | SEM | 10.8 | 10.7 | 10.8 | 9.5 | 10.5 | 11.4 | 11.5 |
| | | at screening | MIN | 12 | 10 | 2 | 5 | 4 | 5 | 1 |
| | | | MAX | 110 | 108 | 105 | 101 | 102 | 110 | 104 |

TABLE 21

WEIGHTED SEVERITY SCORE OF HOT FLUSHES PER WEEK

| GROUP | STRATA | VALUE | Screening (mean of 2 w) | Week 1 | Week 2 | Week 3 | Week 4 | Week 5 | Week 6 | Week 7 | Week 8 | Week 9 |
|---|---|---|---|---|---|---|---|---|---|---|---|---|
| PLACEBO | 50 to 70 | n | 13 | 13 | 13 | 13 | 13 | 13 | 13 | 12 | 12 | 12 |
| | | hot flushes MEAN | 154.2 | 127.2 | 107.7 | 129.9 | 128.1 | 127.6 | 125.0 | 125.7 | 131.1 | 136.8 |
| | | per week SEM | 3.7 | 14.3 | 17.8 | 18.2 | 14.5 | 15.0 | 14.4 | 15.0 | 17.1 | 15.8 |
| | | at screening MIN | 139.5 | 25 | 13 | 14 | 30 | 13 | 8 | 1 | 1 | 0 |
| | | MAX | 178.5 | 228 | 205 | 242 | 210 | 211 | 207 | 184 | 214 | 215 |
| | ≥71 | n | 12 | 12 | 12 | 12 | 12 | 12 | 12 | 12 | 12 | 12 |
| | | hot flushes MEAN | 242.0 | 192.8 | 176.6 | 166.6 | 170.9 | 170.0 | 155.7 | 159.5 | 160.7 | 150.6 |
| | | per week SEM | 21.5 | 20.7 | 20.2 | 20.0 | 23.1 | 20.0 | 29.6 | 21.0 | 23.0 | 22.1 |
| | | at screening MIN | 164 | 63 | 67 | 62 | 53 | 65 | 58 | 48 | 44 | 28 |
| | | MAX | 433.5 | 325 | 295 | 279 | 297 | 283 | 275 | 253 | 278 | 270 |
| DHEA (50 mg) | 50 to 70 | n | 14 | 14 | 14 | 14 | 14 | 13 | 13 | 13 | 13 | 13 |
| | | hot flushes MEAN | 144.3 | 141.0 | 127.1 | 118.9 | 111.6 | 97.8 | 99.0 | 88.3 | 95.8 | 96.0 |
| | | per week SEM | 8.7 | 13.1 | 12.5 | 15.4 | 12.8 | 15.2 | 15.0 | 13.9 | 14.6 | 14.8 |
| | | at screening MIN | 116 | 73 | 15 | 4 | 20 | 0 | 0 | 0 | 0 | 0 |
| | | MAX | 208.5 | 288 | 211 | 234 | 182 | 171 | 163 | 147 | 152 | 174 |
| | ≥71 | n | 11 | 11 | 11 | 11 | 11 | 9 | 9 | 9 | 9 | 9 |
| | | hot flushes MEAN | 241.6 | 175.2 | 150.8 | 149.8 | 166.5 | 154.1 | 138.7 | 137.2 | 129.0 | 121.8 |
| | | per week SEM | 21.1 | 25.8 | 26.7 | 26.3 | 31.2 | 32.7 | 36.1 | 40.2 | 36.4 | 32.6 |
| | | at screening MIN | 176 | 66 | 57 | 35 | 38 | 27 | 31 | 16 | 10 | 38 |
| | | MAX | 404 | 353 | 353 | 326 | 385 | 330 | 335 | 357 | 302 | 314 |

WEIGHTED SEVERITY SCORE OF HOT FLUSHES PER WEEK

| GROUP | STRATA | VALUE | Week 10 | Week 11 | Week 12 | Week 13 | Week 14 | Week 15 | Week 16 |
|---|---|---|---|---|---|---|---|---|---|
| PLACEBO | 50 to 70 | n | 12 | 12 | 12 | 12 | 12 | 12 | 12 |
| | | hot flushes MEAN | 131.3 | 118.0 | 127.5 | 119.3 | 122.4 | 124.0 | 118.8 |
| | | per week SEM | 15.8 | 16.5 | 18.9 | 17.2 | 21.6 | 20.7 | 20.2 |
| | | at screening MIN | 0 | 0 | 0 | 0 | 3 | 5 | 10 |
| | | MAX | 203 | 196 | 219 | 195 | 234 | 219 | 224 |
| | ≥71 | n | 12 | 12 | 12 | 12 | 12 | 12 | 12 |
| | | hot flushes MEAN | 148.1 | 144.1 | 139.7 | 135.0 | 142.9 | 143.2 | 141.3 |
| | | per week SEM | 21.5 | 22.1 | 22.5 | 21.0 | 19.5 | 20.0 | 20.3 |
| | | at screening MIN | 22 | 8 | 23 | 26 | 30 | 26 | 22 |
| | | MAX | 253 | 251 | 273 | 257 | 262 | 232 | 242 |
| DHEA (50 mg) | 50 to 70 | n | 13 | 13 | 13 | 13 | 13 | 13 | 13 |
| | | hot flushes MEAN | 92.7 | 89.8 | 88.5 | 81.4 | 87.0 | 83.7 | 81.6 |
| | | per week SEM | 15.1 | 14.4 | 15.5 | 14.5 | 16.5 | 14.8 | 13.6 |
| | | at screening MIN | 0 | 0 | 0 | 0 | 0 | 5 | 0 |
| | | MAX | 155 | 168 | 193 | 190 | 192 | 180 | 189 |
| | ≥71 | n | 9 | 9 | 9 | 9 | 9 | 9 | 9 |
| | | hot flushes MEAN | 121.6 | 110.2 | 98.7 | 102.8 | 96.6 | 103.5 | 95.2 |
| | | per week SEM | 32.1 | 32.8 | 31.0 | 30.6 | 31.5 | 34.0 | 34.4 |
| | | at screening MIN | 31 | 22 | 4 | 9 | 10 | 11 | 3 |
| | | MAX | 327 | 322 | 315 | 301 | 308 | 330 | 311 |

Example 11

Clinical Trial ERC-213
DHEA Bioavailability Following Administration of Vaginal Suppositories in Post-Menopausal Women with Vaginal Atrophy
Study Design Summary The primary objective of that study was measurement of the maturation value of the vaginal epithelial cells following daily intravaginal application of DHEA. Forty postmenopausal women were randomized to receive a daily dose of one ovule of the following DHEA concentrations: 0.0%, 0.5% (6.5 mg of DHEA/ovule), 1.0% (13 mg of DHEA/ovule) or 1.8% (23.4 mg of DHEA/ovule) for 7 days. The systemic bioavailability of DHEA and its metabolites were also measured.

Results

Figure 27:
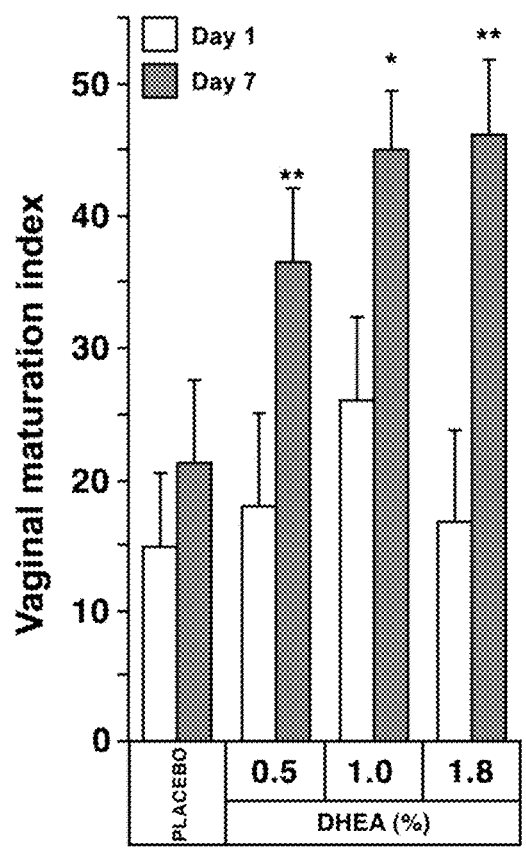
FIG. 27 shows the maturation index measured on Day 1 and Day 7 in 40-75 year-old postmenopausal women following daily administration of vaginal suppositories containing 0%, 0.5%, 1.0% or 1.8% of DHEA. Data are expressed as means±SEM (n=9 or 10). *, $p<0.05$, **, $p<0.01$, Data on Day 7 versus Data on Day 1.
Figure 28:
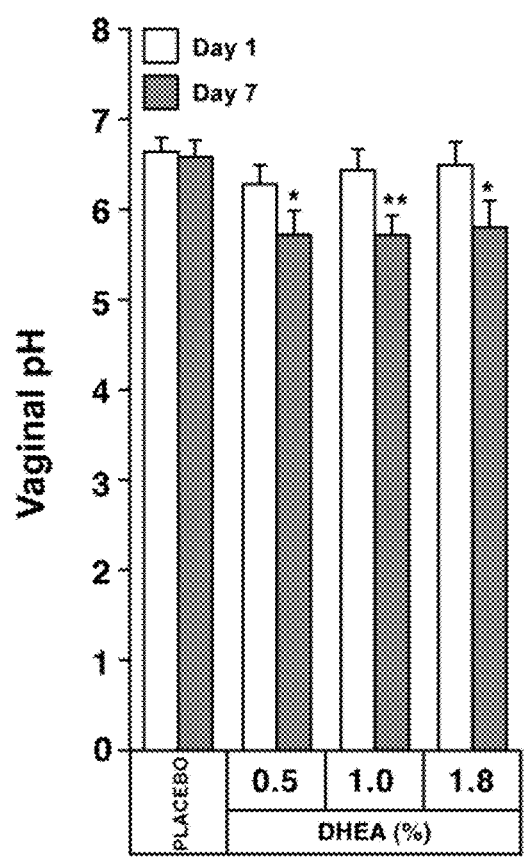
FIG. 28 shows vaginal pH measured on day 1 and Day 7 in 40-75 year old postmenopausal women following daily administration of vaginal suppositories containing 0%, 0.5%, 1.0% or 1.8% of DHEA. Data are expressed as means±SEM (n=9 or 10). *, $p<0.05$, **, $p<0.01$, Data on Day 7 versus Data on Day 1.

After only one week of daily administration of the DHEA suppositories, the maturation index increased by 107% ($p<0.01$), 75% ($p<0.05$) and 150% ($p<0.01$) in the 0.5%, 1.0% and 1.8% DHEA groups, respectively (FIG. 27). No change was observed in the placebo group between day 1 and day 7. Vaginal pH, on the other hand, decreased from 6.29±0.21 to 5.75±0.27 ($p<0.05$), 6.47±0.23 to 5.76±0.22 ($p<0.01$) and 6.53±0.25 to 5.86 ±0.28 ($p<0.05$), respectively in the 0.5%, 1.0% and 1.8% DHEA groups (FIG. 27 28). No change of vaginal pH was observed in the placebo group.

Conclusion

The present data show that the intravaginal administration of DHEA permits to rapidly achieve the beneficial effects against vaginal atrophy without significant changes of serum estrogens, thus avoiding the increased risk of breast cancer associated with the current intravaginal or systemic estrogenic formulations and adding the local benefits on all the layers of the vagina of the recently recognized androgenic component of DHEA action in this tissue.

Pharmaceutical Composition Examples

Set forth below, by way of example and not of limitation, are several pharmaceutical compositions utilizing preferred active SERM Acolbifene (EM-652.HCl; EM-1538) and preferred active sex steroid precursor dehydroepiandrosterone (DHEA, Prasterone). Other compounds of the invention or combination thereof, may be used in place of (or in addition to) Acolbifene or dehydroepiandrosterone. The concentration of active ingredient may be varied over a wide range as discussed herein. The amounts and types of other ingredients that may be included are well known in the art.

Example A

Pharmaceutical Composition for Orally Administration (Capsules)

| Ingredient | Weight % (by weight of total composition) |
|---|---|
| Acolbifene | 5.0 |
| DHEA | 10.0 |
| Lactose hydrous | 70.0 |
| Starch | 4.8 |
| Cellulose microcrystalline | 9.8 |
| Magnesium stearate | 0.4 |

Example B

Pharmaceutical Composition for Orally Administration (Tablets)

| Ingredient | Weight % (by weight of total composition) |
|---|---|
| Acolbifene | 5.0 |
| DHEA | 15.0 |
| Gelatin | 5.0 |
| Lactose | 58.5 |
| Starch | 16.5 |

Example C

Topical Administration (Cream)

| Ingredient | Weight % (by weight of total composition) |
|---|---|
| DHEA | 1.0 |
| Acolbifene | 0.2 |
| Emulsifying Wax, NF | 18.0 |
| Light mineral oil, NF | 12.0 |
| Benzyl alcohol | 1.0 |
| Ethanol 95% USP | 33.8 |
| Purifed water, USP | 34.0 |

Example D

Vaginal Administration

Vaginal Suppository or Ovule

| Ingredient | Weight % (by weight of total composition) |
|---|---|
| DHEA | 0.25 to 2.0 |
| Acolbifene | 0.25 to 3.0 |
| Witepsol H-15 base | 95.0 to 99.5 |

DHEA suppositories were prepared using Witepsol H-15 base (Medisca, Montreal, Canada). Any other lipophilic base such as Hard Fat, Fattibase, Wecobee, cocoa butter, theobroma oil or other combinations of Witepsol bases could used. Preferred SERMs are EM-800, and Acolbifene Kit Examples Set forth below, by way of example and not of limitation, are several kits utilizing preferred active SREM Acolbifene, preferred antiestrogen Faslodex and preferred active a sex steroid precursor DHEA. The concentration of active ingredient may be varied over a wide range as discussed herein. The amounts and types of other ingredients that may be included are well known in the art.

Example D

Kit

The SERM and Sex Steroid Precursor are Orally Administered

Non-Steroidal Antiestrogen Composition for Oral Administration (Capsules)

| Ingredient | Weight % (by weight of total composition) |
|---|---|
| Acolbifene | 5.0 |
| Lactose hydrous | 80.0 |
| Starch | 4.8 |
| Cellulose microcrystalline | 9.8 |
| Magnesium stearate | 0.4 |

+
DHEA Composition for Oral Administration
(Gelatin Capsule)

| Ingredient | Weight % (by weight of total composition) |
|---|---|
| DHEA | 25.0 |
| Lactose hydrous | 27.2 |
| Sodium Starch Glycolate | 20.0 |
| Microcrystalline Cellulose, Colloidal Silicon Dioxide, Silica Colloidal Anhydrous and Light Anhydrous Silicic Acid | 27.2 |
| Colloidal Silicon Dioxide | 0.1 |
| Magnesium stearate | 0.5 |

Other SERMs may be substituted for Acolbifene in the above formulations, as well as other sex steroid precursors may be substituted for DHEA. More than one SERM or more than one sex steroid precursor may be included in which case the combined weight percentage is preferably that of the weight percentage for the single sex steroid precursor or single SERM given in the examples above.

Example E

Kit
The SERM is Orally Administered and the Sex Steroid Precursor is Intra Vaginally Administered SERM Composition for Oral Administration (Capsules)

| Ingredient | Weight % (by weight of total composition) |
|---|---|
| Acolbifene | 5.0 |
| Lactose hydrous | 80.0 |
| Starch | 4.8 |
| Cellulose microcrystalline | 9.8 |
| Magnesium stearate | 0.4 |

+
Vaginal Suppository

| Ingredient | Weight % (by weight of total composition) |
|---|---|
| DHEA | 0.25 to 2.0 |
| Witepsol H-15 base | 98 to 99.75 |

DHEA suppositories were prepared using Witepsol H-15 base (Medisca, Montreal, Canada). Any other lipophilic base such as Hard Fat, Fattibase, Wecobee, cocoa butter, theobroma oil or other combinations of Witepsol bases could used.

Example F

Kit
The SERM and the Sex Steroid Precursor are Intra Vaginally Administered Vaginal Suppository

| Ingredient | Weight % (by weight of total composition) |
|---|---|
| DHEA | 0.25 to 2.0 |
| Witepsol H-15 base | 98 to 99.75 |

+
Vaginal Suppository

| Ingredient | Weight % (by weight of total composition) |
|---|---|
| Acolbifene | 0.3 to 3.0 |
| Hard Fat | 97.0 to 99.7 |

Acolbifene suppositories were prepared using Hard Fat (Witepsol). Any other bases such as Fattibase, Wecobee, cocoa butter, theobroma oil or other combinations of Hard Fat could be used.

Example G

The SERM is Orally Administered and the Sex Steroid Precursor is Percutaneously Administered
SERM Composition for Oral Administration (Capsules)

| Ingredient | Weight % (by weight of total composition) |
|---|---|
| Acolbifene | 5.0 |
| Lactose hydrous | 80.0 |
| Starch | 4.8 |
| Cellulose microcrystalline | 9.8 |
| Magnesium stearate | 0.4 |

+
Sex Steroid Precursor Composition
For Oral Administration (Gel)

| Ingredient | Weight % (by weight of total composition) |
|---|---|
| DHEA | 2.0 |
| Caprylic-capric Triglyceride (Neobee M-5) | 5.0 |
| Hexylene Glycol | 15.0 |
| Transcutol (diethyleneglycol monomethyl ether) | 5.0 |
| Benzyl alcohol | 2.0 |
| Cyclomethicone (Dow corning 345) | 5.0 |
| Ethanol (absolute) | 64.0 |
| Hydroxypropylcellulose (1500 cps) (KLUCEL) | 2.0 | or
Sex Steroid Precursor Composition
for Oral Administration (Cream)

| Ingredient | Weight % (by weight of total composition) Formulation EM-760-48-1.0% |
|---|---|
| Cyclometicone | 5.0% |
| Light mineral oil | 3.0% |
| 2-ethylhexyl stearate | 10.0% |
| Cutina E24 | 1.0% |
| DC emulsifier 10 | 3.0% |
| BHT | 0.09% |
| Propyleneglycol | 46.01% |
| Ethanol 95 | 10.0% |
| DHEA | 1.0% |
| Eau purifiée | 15.0% |
| MgSO4 | 0.65% |
| Ethanol 95 | 5.25% |
| Total | 100.0% |

Example H

Kit

The Antiestrogen is Intramuscularly Administered and Sex Steroid Precursor is Orally Administered Commercially Available Steroidal Antiestrogen Faslodex

+

DHEA Composition for Oral Administration
(Gelatin Capsule)

| Ingredient | Weight % (by weight of total composition) |
|---|---|
| DHEA | 25.0 |
| Lactose hydrous | 27.2 |
| Sodium Starch Glycolate | 20.0 |
| Microcrystalline Cellulose, Colloidal Silicon Dioxide, Silica Colloidal Anhydrous and Light Anhydrous Silicic Acid | 27.2 |
| Colloidal Silicon Dioxide | 0.1 |
| Magnesium stearate | 0.5 |

Other SERMs (Toremifene, Ospemifene, Raloxifene, Arzoxifene, Lasofoxifene, TSE-424, ERA-923, EM-800, SERM 3339, GW-5638) may be substituted for Acolbifene in the above formulations, as well as other sex steroid inhibitors may be substituted for DHEA. More than one SERM or more than one precursor may be included in which case the combined weight percentage is preferably that of the weight percentage for the single precursor or single SERM given in the examples above.

The invention has been described in terms of preferred embodiments and examples, but is not limited thereby. Those of skill in the art will readily recognize the broader applicability and scope of the invention which is limited only by the patent claims herein.

What is claimed is:

1. A method of treating Alzheimer's disease said method comprising administering to a postmenopausal woman in need of said treatment, (i) an amount of a sex steroid precursor selected from the group consisting of dehydroepiandrosterone, dehydroepiandrosterone-sulfate, androst-5-ene-3β,17β-diol, 4-androstene-3,17-dione, in combination with (ii) an amount of a selective estrogen receptor modulator, wherein the modulator is EM-652 or a pharmaceutically acceptable salt thereof,

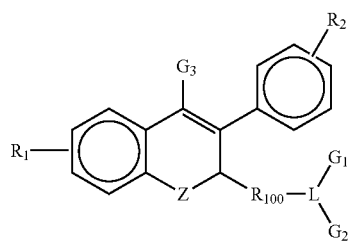

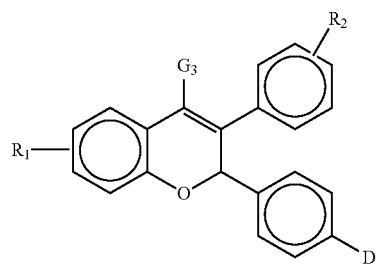

wherein said amounts are sufficient to achieve said treatment.

2. The method of claim 1 where said selective estrogen receptor modulator is:

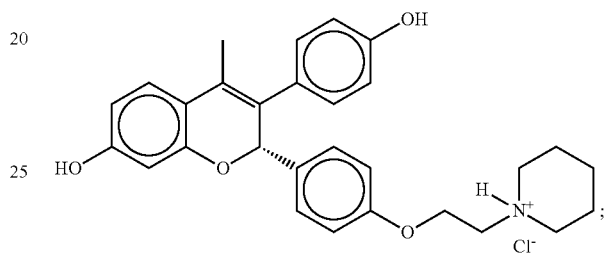

and wherein the selective estrogen receptor modulator is an optically active compound.

3. The method of claim 1 wherein the selective estrogen receptor modulator is a EM-652 salt of an acid selected from the group consisting of acetic acid, adipic acid, benzenesulfonic acid, benzoic acid, camphorsulfonic acid, citric acid, fumaric acid, hydroiodic acid, hydrobromic acid, hydrochloric acid, hydrochlorothiazide acid, hydroxy-naphthoic acid, lactic acid, maleic acid, methanesulfonic acid, methylsulfuric acid, 1,5-naphthalenedisulfonic acid, nitric acid, palmitic acid, pivalic acid, phosphoric acid, propionic acid, succinic acid, sulfuric acid, tartaric acid, terephthalic acid, p-toluenesulfonic acid, and valeric acid.

4. The method of claim 1 wherein said selective estrogen receptor modulator is:

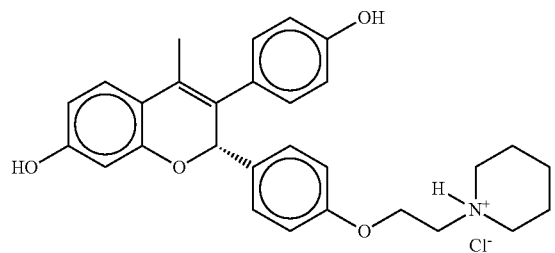

wherein the selective estrogen receptor modulator is an optically active compound; and wherein the sex steroid precursor is dehydroepiandrosterone.

5. The method of claim 1 wherein said selective estrogen receptor modulator is intravaginally administered.

6. The method of claim 2 wherein the selective estrogen receptor modulator is intravaginally administered.

7. The method of claim 1 wherein the selective estrogen receptor modulator is orally administered.

8. The method of claim 1 wherein the selective estrogen receptor modulator is percutaneously administered.

9. The method of claim 1, wherein the amount of selective estrogen receptor modulator decreases the risk of breast, uterine and endometrial cancer normally occurring in said postmenopausal women and to prevent bone loss, osteoporosis, hypertension, insulin resistance, diabetes, obesity and atherosclerosis.

* * * * *

UNITED STATES PATENT AND TRADEMARK OFFICE
CERTIFICATE OF CORRECTION

PATENT NO. : 10,342,805 B2
APPLICATION NO. : 13/875027
DATED : July 9, 2019
INVENTOR(S) : Fernand Labrie Page 1 of 1

It is certified that error appears in the above-identified patent and that said Letters Patent is hereby corrected as shown below:

In the Claims

In Claim 1, Column 71, Lines 56-66, delete the molecular structure.

In Claim 1, Column 72, Lines 1-11, delete the molecular structure.

Signed and Sealed this
Twenty-second Day of October, 2019

Andrei Iancu
*Director of the United States Patent and Trademark Office*